US008158355B2

(12) United States Patent
Ruan et al.

(10) Patent No.: US 8,158,355 B2
(45) Date of Patent: Apr. 17, 2012

(54) METHOD TO GENERATE OR DETERMINE NUCLEIC ACID TAGS CORRESPONDING TO THE TERMINAL ENDS OF DNA MOLECULES USING SEQUENCES ANALYSIS OF GENE EXPRESSION (TERMINAL SAGE)

(75) Inventors: Yijun Ruan, Singapore (SG); Chialin Wei, Singapore (SG)

(73) Assignee: The Agency For Science, Technology and Research, Singapore (SG)

( * ) Notice: Subject to any disclaimer, the term of this patent is extended or adjusted under 35 U.S.C. 154(b) by 0 days.

(21) Appl. No.: 11/145,005

(22) Filed: Jun. 3, 2005

(65) Prior Publication Data

US 2006/0084083 A1    Apr. 20, 2006

Related U.S. Application Data

(63) Continuation-in-part of application No. PCT/SG03/00255, filed on Dec. 4, 2003.

(30) Foreign Application Priority Data

Dec. 4, 2002 (GB) .................................... 0228289.5

(51) Int. Cl.
*C12Q 1/68* (2006.01)
(52) U.S. Cl. ...................................................... 435/6.12
(58) Field of Classification Search .................... None
See application file for complete search history.

(56) References Cited

U.S. PATENT DOCUMENTS

| 5,710,000 | A | 1/1998 | Gingeras et al. |
| 5,981,190 | A | 11/1999 | Israel |
| 6,136,537 | A | 10/2000 | Macevicz |
| 6,383,743 | B1 | 5/2002 | Kinzler et al. |

FOREIGN PATENT DOCUMENTS

| EP | 0 761 822 A | 3/1997 |
| JP | 2005-535311 | 11/2005 |
| WO | WO 01/48247 | 7/2001 |
| WO | WO 02/10438 | 2/2002 |
| WO | 02074951 | 9/2002 |
| WO | 02086163 | 10/2002 |
| WO | WO 03-106672 | 12/2003 |

OTHER PUBLICATIONS

Yamamoto et al. (2001) J of Immunological methods 250:45-66.*
New England Biolabs Jul. 3, 2007 printout Recognition sites of Type IIS restriction sites.*
Boyd et al. (1986) Nucleic acids research vol. 14 No. 13 pp. 5255-5273.*
Szybalski et al. (1991) Gene 100 pp. 13-26.*
Tucholski et al. (1995) Gene 157 00:87-92.*
New England Biolabs Catalog 1995 pp. 2 and 21.*
NEB Fsel 8 base recognition site.*
Chen J.-J. et al. "Generation of longer cDNA fragments from serial analysis of gene expression tags from serial analysis of gene expression tags for gene identification" Proceedings of the National Academy of Sciences of USA, National Academy of Science, Washington, US, vol. 97, No. 1, Jan. 4, 2000, pp. 349-353.
Ryo A. et al. "A modified serial analysis of gene expression that generates longer sequence tags by nonpalindromic cohesive linker ligation" Analytical Biochemistry vol. 277, No. 1, Jan. 1, 2000, pp. 160-162.
Yamamoto M. et al. "Use of serial analysis of gene expression (SAGE) technology" Journal of Immunological Methods, vol. 250, No. 1-2, Apr. 1, 2001, pp. 45-66.
Vesculescu V.E. et al. "Characterization of the Yeast Transcriptome" Cell, Cell Press, Cambridge, MA, US, vol. 88, Jan. 24, 1997, pp. 243-251.
Velculescu V.C. et al. "Serial analysis of Gene Expression" Science, American Association for the Advancement of Science, US, vol. 270, No. 5235, Oct. 20, 1995, pp. 484-487.
Schmidt, W.M., et. al. (1999) CapSelect: A highly sensitive method for 5' CAP-dependent enrichment of full-length cDNA in PCR-mediated analysis of mRNAs. Nucleic Acids Research, vol. 27 No. 21 p. i-iv.

* cited by examiner

*Primary Examiner* — Samuel Woolwine
*Assistant Examiner* — Suchira Pande
(74) *Attorney, Agent, or Firm* — Mark J. FitzGerald; Nixon Peabody LLP

(57) ABSTRACT

A method of providing an indication of an instance of expression of a gene is described herein, the method which may comprise the steps of: (a) providing a complementary deoxyribonucleic acid (cDNA) having a terminus comprising a terminal transcribed sequence of a gene; (b) linking the cDNA to an linker sequence thereby forming a linked nucleic acid, in which the linker sequence comprises a first recognition site for a first nucleic acid cleavage enzyme, preferably a restriction endonuclease, that allows nucleic acid cleavage at a site distant from the first recognition site; and (c) cleaving the linked nucleic acid with the first nucleic acid cleavage enzyme to provide a linked tag, in which the linked tag comprises a nucleotide sequence tag representative of a terminal transcribed sequence of the gene; and (d) detecting the presence or identity of the linked tag or the nucleotide sequence tag to provide an indication of an instance of gene expression.

10 Claims, 7 Drawing Sheets

The second round of adding the MmeI-BsmBI linkers, releasing the tags,
Ligating and PCR the ditags, removing the arms, purifying ditags,
Concatenating and cloning → SAGE Walking Library.

SEQUENCE LISTING

```
<160> NUMBER OF SEQ ID NOS: 165

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (7)..(12)
<223> OTHER INFORMATION: a, c, g, t, unknown or other

<400> SEQUENCE: 1
gaggagnnnn nntccgac                                                      18

<210> SEQ ID NO 2
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 2
gaggagcgtc tctccgac                                                   18

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(29)
<223> OTHER INFORMATION: a, c, g, t, unknown or other

<400> SEQUENCE: 3 gtcccnnnn nnnnnnnnnn nnnnnnnnn                                        29

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: a, c, g, t, unknown or other

<400> SEQUENCE: 4
nvtttttttt tttttccggc cgg                                             23

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(26)
<223> OTHER INFORMATION: a, c, g, t, unknown or other

<400> SEQUENCE: 5
tccracnnnn nnnnnnnnnn nnnnnn                                          26

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(15)
<223> OTHER INFORMATION: a, c, g, t, unknown or other

<400> SEQUENCE: 6
cacctgcnnn nnnnn                                                      15
```

```
<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 7
cagctcnnnn nnnnnnn                                                    17

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, g, t, unknown or other
<220> FEATURE:
<221> NAME/KEY: modified_base
<222> LOCATION: (17)..(22)
<223> OTHER INFORMATION: a, c, g, t, unknown or other
<220> FEATURE:
<221> NAME/KEY: modified_base
<222> LOCATION: (26)..(37)
<223> OTHER INFORMATION: a, c, g, t, unknown or other

<400> SEQUENCE: 8
nnnnnnnnnn nngaacnnnn nntccnnnnn nnnnnnn                              37

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, g, t, unknown or other
<220> FEATURE:
<221> NAME/KEY: modified_base
<222> LOCATION: (18)..(21)
<223> OTHER INFORMATION: a, c, g, t, unknown or other
<220> FEATURE:
<221> NAME/KEY: modified_base
<222> LOCATION: (27)..(38)
<223> OTHER INFORMATION: a, c, g, t, unknown or other

<400> SEQUENCE: 9
nnnnnnnnnn nnnnnacnnn ngtaycnnnn nnnnnnnn                             38

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 10
```

```
gaagacnnnn nnnnnnn                                                  17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(17)
<223> OTHER INFORMATION: a, c, g, t, unknown or other

<400> SEQUENCE: 11 gcagcnnnn nnnnnnn                                                   17

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, g, t, unknown or other

<400> SEQUENCE: 12
gaagacnnnn nn                                                       12

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, g, t, unknown or other

<400> SEQUENCE: 13 ccatcnnnnn                                                          10

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, c, g, t, unknown or other

<400> SEQUENCE: 14
cttgagnnnn nnnnnnnnnn nn                                            22

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (6)..(19)
<223> OTHER INFORMATION: a, c, g, t, unknown or other

<400> SEQUENCE: 15 acggcnnnn nnnnnnnnn                                                    19

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(18)
<223> OTHER INFORMATION: a, c, g, t, unknown or other

<400> SEQUENCE: 16
acggcnnnnn nnnnnnnn                                                    18

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, g, t, unknown or other
<220> FEATURE:
<221> NAME/KEY: modified_base
<222> LOCATION: (16)..(21)
<223> OTHER INFORMATION: a, c, g, t, unknown or other
<220> FEATURE:
<221> NAME/KEY: modified_base
<222> LOCATION: (25)..(36)
<223> OTHER INFORMATION: a, c, g, t, unknown or other

<400> SEQUENCE: 17
nnnnnnnnnn nncgannnnn ntgcnnnnnn nnnnnn                                36

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, g, t, unknown or other

<400> SEQUENCE: 18
gtatccnnnn nn                                                          12

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, g, t, unknown or other
```

```
<400> SEQUENCE: 19
actgggnnnn n                                                              11

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, g, t, unknown or other

<400> SEQUENCE: 20 ggatcnnnnn                                                                10

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(13)
<223> OTHER INFORMATION: a, c, g, t, unknown or other
<220> FEATURE:
<221> NAME/KEY: modified_base
<222> LOCATION: (17)..(21)
<223> OTHER INFORMATION: a, c, g, t, unknown or other
<220> FEATURE:
<221> NAME/KEY: modified_base
<222> LOCATION: (25)..(37)
<223> OTHER INFORMATION: a, c, g, t, unknown or other

<400> SEQUENCE: 21
nnnnnnnnnn nnngagnnnn nctcnnnnnn nnnnnnn                                  37

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, g, t, unknown or other
<220> FEATURE:
<221> NAME/KEY: modified_base
<222> LOCATION: (15)..(19)
<223> OTHER INFORMATION: a, c, g, t, unknown or other
<220> FEATURE:
<221> NAME/KEY: modified_base
<222> LOCATION: (24)..(33)
<223> OTHER INFORMATION: a, c, g, t, unknown or other

<400> SEQUENCE: 22
nnnnnnnnnn nnacnnnnnc tccnnnnnnn nnn                                      33

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (6)..(11)
<223> OTHER INFORMATION: a, c, g, t, unknown or other

<400> SEQUENCE: 23
gcatcnnnnn n                                                              11

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(15)
<223> OTHER INFORMATION: a, c, g, t, unknown or other

<400> SEQUENCE: 24
ctcagnnnnn nnnnn                                                          15

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, c, g, t, unknown or other

<400> SEQUENCE: 25
gaggagnnnn nnnnnn                                                         16

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, c, g, t, unknown or other

<400> SEQUENCE: 26
gtgcagnnnn nnnnnnnnnn nn                                                  22

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, g, t, unknown or other

<400> SEQUENCE: 27 gtctcnnnnn                                                                10

<210> SEQ ID NO 28
<211> LENGTH: 19
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, c, g, t, unknown or other

<400> SEQUENCE: 28
gggacnnnnn nnnnnnnnn                                                          19

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(13)
<223> OTHER INFORMATION: a, c, g, t, unknown or other
<220> FEATURE:
<221> NAME/KEY: modified_base
<222> LOCATION: (17)..(22)
<223> OTHER INFORMATION: a, c, g, t, unknown or other
<220> FEATURE:
<221> NAME/KEY: modified_base
<222> LOCATION: (26)..(37)
<223> OTHER INFORMATION: a, c, g, t, unknown or other

<400> SEQUENCE: 29
nnnnnnnnnn nnngacnnnn nntggnnnnn nnnnnnn                                      37

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(14)
<223> OTHER INFORMATION: a, c, g, t, unknown or other

<400> SEQUENCE: 30
ctcagnnnnn nnnn                                                               14

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(14)
<223> OTHER INFORMATION: a, c, g, t, unknown or other

<400> SEQUENCE: 31
acctgcnnnn nnnn                                                               14

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(14)
<223> OTHER INFORMATION: a, c, g, t, unknown or other
<220> FEATURE:
<221> NAME/KEY: modified_base
<222> LOCATION: (18)..(23)
<223> OTHER INFORMATION: a, c, g, t, unknown or other
<220> FEATURE:
<221> NAME/KEY: modified_base
<222> LOCATION: (26)..(40)
<223> OTHER INFORMATION: a, c, g, t, unknown or other

<400> SEQUENCE: 32
nnnnnnnnnn nnnnccannn nnngtnnnnn nnnnnnnnnn                               40

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(13)
<223> OTHER INFORMATION: a, c, g, t, unknown or other
<220> FEATURE:
<221> NAME/KEY: modified_base
<222> LOCATION: (17)..(23)
<223> OTHER INFORMATION: a, c, g, t, unknown or other
<220> FEATURE:
<221> NAME/KEY: modified_base
<222> LOCATION: (26)..(39)
<223> OTHER INFORMATION: a, c, g, t, unknown or other

<400> SEQUENCE: 33
nnnnnnnnnn nnnccannnn nnntcnnnnn nnnnnnnn                                 39

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 34
ggcggannnn nnnnnnn                                                        17

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, g, t, unknown or other

<400> SEQUENCE: 35
ggtctcnnnn n                                                              11

<210> SEQ ID NO 36
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, c, g, t, unknown or other

<400> SEQUENCE: 36
ctgaagnnnn nnnnnnnnnn nn                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, c, g, t, unknown or other

<400> SEQUENCE: 37
ctgragnnnn nnnnnnnnnn nn                                              22

<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, g, t, unknown or other

<400> SEQUENCE: 38
cgtctcnnnn n                                                          11

<210> SEQ ID NO 39
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(13)
<223> OTHER INFORMATION: a, c, g, t, unknown or other
<220> FEATURE:
<221> NAME/KEY: modified_base
<222> LOCATION: (17)..(21)
<223> OTHER INFORMATION: a, c, g, t, unknown or other
<220> FEATURE:
<221> NAME/KEY: modified_base
<222> LOCATION: (25)..(37)
<223> OTHER INFORMATION: a, c, g, t, unknown or other

<400> SEQUENCE: 39
nnnnnnnnnn nnnaagnnnn ncttnnnnnn nnnnnnn                              37

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (6)..(11)
<223> OTHER INFORMATION: a, c, g, t, unknown or other

<400> SEQUENCE: 40
cccgcnnnnn n                                                                        11

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(18)
<223> OTHER INFORMATION: a, c, g, t, unknown or other

<400> SEQUENCE: 41
ggatgnnnnn nnnnnnnn                                                                 18

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, c, g, t, unknown or other

<400> SEQUENCE: 42
ctggagnnnn nnnnnnnnnn nn                                                            22

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(13)
<223> OTHER INFORMATION: a, c, g, t, unknown or other
<220> FEATURE:
<221> NAME/KEY: modified_base
<222> LOCATION: (17)..(21)
<223> OTHER INFORMATION: a, c, g, t, unknown or other
<220> FEATURE:
<221> NAME/KEY: modified_base
<222> LOCATION: (25)..(38)
<223> OTHER INFORMATION: a, c, g, t, unknown or other

<400> SEQUENCE: 43
nnnnnnnnnn nnngaynnnn nrtcnnnnnn nnnnnnnn                                           38

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(15)
<223> OTHER INFORMATION: a, c, g, t, unknown or other
```

<400> SEQUENCE: 44
gacgcnnnnn nnnnn                                                           15

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(13)
<223> OTHER INFORMATION: a, c, g, t, unknown or other
<220> FEATURE:
<221> NAME/KEY: modified_base
<222> LOCATION: (17)..(21)
<223> OTHER INFORMATION: a, c, g, t, unknown or other
<220> FEATURE:
<221> NAME/KEY: modified_base
<222> LOCATION: (25)..(37)
<223> OTHER INFORMATION: a, c, g, t, unknown or other

<400> SEQUENCE: 45
nnnnnnnnnn nnngaynnnn nvtcnnnnnn nnnnnnn                                    37

<210> SEQ ID NO 46
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, c, g, t, unknown or other

<400> SEQUENCE: 46
ggtgannnnn nnn                                                              13

<210> SEQ ID NO 47
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, c, g, t, unknown or other

<400> SEQUENCE: 47
ccttcnnnnn n                                                                11

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(10)
<223> OTHER INFORMATION: a, c, g, t, unknown or other

<400> SEQUENCE: 48 ctcttcnnnn                                                                  10

<210> SEQ ID NO 49
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, c, g, t, unknown or other

<400> SEQUENCE: 49
gaagannnnn nnn                                                          13

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, g, t, unknown or other

<400> SEQUENCE: 50 gagtcnnnnn                                                              10

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(26)
<223> OTHER INFORMATION: a, c, g, t, unknown or other

<400> SEQUENCE: 51
tccracnnnn nnnnnnnnnn nnnnnn                                            26

<210> SEQ ID NO 52
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(11)
<223> OTHER INFORMATION: a, c, g, t, unknown or other

<400> SEQUENCE: 52
cctcnnnnnn n                                                            11

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)

<223> OTHER INFORMATION: a, c, g, t, unknown or other

<400> SEQUENCE: 53 gagtcnnnnn                                                                10

<210> SEQ ID NO 54
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, g, t, unknown or other
<220> FEATURE:
<221> NAME/KEY: modified_base
<222> LOCATION: (17)..(21)
<223> OTHER INFORMATION: a, c, g, t, unknown or other
<220> FEATURE:
<221> NAME/KEY: modified_base
<222> LOCATION: (25)..(37)
<223> OTHER INFORMATION: a, c, g, t, unknown or other

<400> SEQUENCE: 54
nnnnnnnnnn nngaacnnnn nctcnnnnnn nnnnnnn                                  37

<210> SEQ ID NO 55
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, g, t, unknown or other
<220> FEATURE:
<221> NAME/KEY: modified_base
<222> LOCATION: (17)..(22)
<223> OTHER INFORMATION: a, c, g, t, unknown or other
<220> FEATURE:
<221> NAME/KEY: modified_base
<222> LOCATION: (26)..(37)
<223> OTHER INFORMATION: a, c, g, t, unknown or other

<400> SEQUENCE: 55
nnnnnnnnnn nngaacnnnn nntacnnnnn nnnnnnn                                  37

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(18)
<223> OTHER INFORMATION: a, c, g, t, unknown or other

<400> SEQUENCE: 56
cccacannnn nnnnnnnn                                                       18

<210> SEQ ID NO 57
<211> LENGTH: 11
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<221> NAME/KEY: modified_base
<222> LOCATION: (8)..(11)
<223> OTHER INFORMATION: a, c, g, t, unknown or other

<400> SEQUENCE: 57
gctcttcnnn n                                                          11

<210> SEQ ID NO 58
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(14)
<223> OTHER INFORMATION: a, c, g, t, unknown or other

<400> SEQUENCE: 58
gcatcnnnnn nnnn                                                       14

<210> SEQ ID NO 59
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, c, g, t, unknown or other

<400> SEQUENCE: 59
ggtgannnnn nnn                                                        13

<210> SEQ ID NO 60
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(12)
<223> OTHER INFORMATION: a, c, g, t, unknown or other

<400> SEQUENCE: 60
cccgnnnnnn nn                                                         12

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, c, g, t, unknown or other

<400> SEQUENCE: 61
ggatgnnnnn nnnnnnnn                                                   19

<210> SEQ ID NO 62
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 62
gaccgannnn nnnnnnn                                                      17

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 63
cacccannnn nnnnnnn                                                      17

<210> SEQ ID NO 64
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(16)
<223> OTHER INFORMATION: a, c, g, t, unknown or other

<400> SEQUENCE: 64
atgaannnnn nnnnnn                                                       16

<210> SEQ ID NO 65
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(16)
<223> OTHER INFORMATION: a, c, g, t, unknown or other

<400> SEQUENCE: 65
acggannnnn nnnnnn                                                       16

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 66
```

-continued caarcannnn nnnnnnn                                                  17

<210> SEQ ID NO 67
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (46)..(46)
<223> OTHER INFORMATION: a, c, g, t, unknown or other

<400> SEQUENCE: 67
gactagttct agatcgcgag cggccgccct tttttttttt ttttvn                  46

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 68
gactagttct agatcgcgag c                                             21

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 69
ggccgctcgc gatctagaac tagtc                                         25

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 70
tttggatttg ctggtgcagt acaactaggc gaggagcgtc tctccgac                48

<210> SEQ ID NO 71
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 71
gtcggagaga cgctcctcgc ctagttgtac tgcaccagca aatcc                   45

<210> SEQ ID NO 72
<211> LENGTH: 48
<212> TYPE: DNA
<213> ORGANISM: Artificial Sequence
<220> FEATURE:
<223> OTHER INFORMATION: Description of Artificial Sequence: Synthetic
      linker sequence

```
<400> SEQUENCE: 72
tttctgctcg aattcaagct tctaacgtac gaggagcgtc tctccgac                48

<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 73
gtcggagaga cgctcctcgt acgttagaag cttgaattcg agcag                   45

<210> SEQ ID NO 74
<211> LENGTH: 50
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (49)..(50)
<223> OTHER INFORMATION: a, c, g, t, unknown or other

<400> SEQUENCE: 74
tttggatttg ctggtgcagt acaactaggc gaggagcgtc tctccgacnn              50

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 75
gtcggagaga cgctcctcgc ctagttgtac tgcaccagca aatcc                   45

<210> SEQ ID NO 76
<211> LENGTH: 50
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (49)..(50)
<223> OTHER INFORMATION: a, c, g, t, unknown or other

<400> SEQUENCE: 76
tttctgctcg aattcaagct tctaacgtac gaggagcgtc tctccgacnn              50

<210> SEQ ID NO 77
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 77
gtcggagaga cgctcctcgt acgttagaag cttgaattcg agcag                   45

<210> SEQ ID NO 78
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gtgctcgtgg gatttgctgg tgcagtaca                                         29

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gagctcgtgc tgctcgaatt caagcttct                                         29

<210> SEQ ID NO 80
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (42)..(42)
<223> OTHER INFORMATION: a, c, g, t, unknown or other

<400> SEQUENCE: 80
gactagttct agatcgcgag gccggccttt ttttttttt vn                           42

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 81
gtgctcgtgg gatttgctgg tgcagtaca                                         29

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 82
tgtactgcac cacgaaatcc cacgagcac                                         29

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 83
tcggatcgcg atctagaact agtc                                              24
```

<210> SEQ ID NO 84
<211> LENGTH: 31
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 84
tttgactagt tctagatcgc gatccgaccg g                              31

<210> SEQ ID NO 85
<211> LENGTH: 50
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (49)..(50)
<223> OTHER INFORMATION: a, c, g, t, unknown or other

<400> SEQUENCE: 85
tttggatttg ctggtgcagt acaactaggc gaggagcgtc tctccgacnn           50

<210> SEQ ID NO 86
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 86
gtcggagaga cgctcctcgc ctagttgtac tgcaccagca aatcc                45

<210> SEQ ID NO 87
<211> LENGTH: 50
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (49)..(50)
<223> OTHER INFORMATION: a, c, g, t, unknown or other

<400> SEQUENCE: 87
tttctgctcg aattcaagct tctaacgtac gaggagcgtc tctccgacnn           50

<210> SEQ ID NO 88
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 88
gtcggagaga cgctcctcgt acgttagaag cttgaattcg agcag                45

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence: Synthetic

```
                         primer

<400> SEQUENCE: 89
gtgctcgtgg gatttgctgg tgcagtaca                                      29

<210> SEQ ID NO 90
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gagctcgtgc tgctcgaatt caagcttct                                      29

<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (40)..(40)
<223> OTHER INFORMATION: a, c, g, t, unknown or other

<400> SEQUENCE: 91
gagagagaga gcggccgctt tttttttttt ttttttttvn                          40

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 92
ggccgctcgc gatctagaac tagtc                                          25

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 93
gactagttct agatcgcgag c                                              21

<210> SEQ ID NO 94
<211> LENGTH: 54
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (50)..(54)
<223> OTHER INFORMATION: a, c, g, t, unknown or other

<400> SEQUENCE: 94
tttggatttg ctggtgcagt acaactaggc gaggagcgtc tctccgacgn nnnn           54
```

```
<210> SEQ ID NO 95
<211> LENGTH: 54
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (49)..(54)
<223> OTHER INFORMATION: a, c, g, t, unknown or other

<400> SEQUENCE: 95
tttggatttg ctggtgcagt acaactaggc gaggagcgtc tctccgacnn nnnn          54

<210> SEQ ID NO 96
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 96
gtcggagaga cgctcctcgc ctagttgtac tgcaccagca aatcc                    45

<210> SEQ ID NO 97
<211> LENGTH: 54
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (50)..(54)
<223> OTHER INFORMATION: a, c, g, t, unknown or other

<400> SEQUENCE: 97
tttctgctcg aattcaagct tctaacgtac gaggagcgtc tctccgacgn nnnn          54

<210> SEQ ID NO 98
<211> LENGTH: 54
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (49)..(54)
<223> OTHER INFORMATION: a, c, g, t, unknown or other

<400> SEQUENCE: 98
tttctgctcg aattcaagct tctaacgtac gaggagcgtc tctccgacnn nnnn          54

<210> SEQ ID NO 99
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 99
gtcggagaga cgctcctcgt acgttagaag cttgaattcg agcag                    45

<210> SEQ ID NO 100
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 100
gtgctcgtgg gatttgctgg tgcagtaca                                       29

<210> SEQ ID NO 101
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gagctcgtgc tgctcgaatt caagcttct                                       29

<210> SEQ ID NO 102
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(34)
<223> OTHER INFORMATION: a, c, g, t, unknown or other

<400> SEQUENCE: 102
gagagagaga ctggagtttt tttttttttt ttvn                                 34

<210> SEQ ID NO 103
<211> LENGTH: 50
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 103
tttggatttg ctggtgcagt acaactaggc gaggagcgtc tctccgactt                50

<210> SEQ ID NO 104
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 104
gtcggagaga cgctcctcgc ctagttgtac tgcaccagca aatcc                     45

<210> SEQ ID NO 105
<211> LENGTH: 50
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 105
tttctgctcg aattcaagct tctaacgtac gaggagcgtc tctccgactt                50

<210> SEQ ID NO 106
```

<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 106
gtcggagaga cgctcctcgt acgttagaag cttgaattcg agcag             45

<210> SEQ ID NO 107
<211> LENGTH: 16
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 107
tcgacccacg cgtccg             16

<210> SEQ ID NO 108
<211> LENGTH: 16
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 108
cggacgcgtg ggtcga             16

<210> SEQ ID NO 109
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gtgctcgtgg gatttgctgg tgcagtaca             29

<210> SEQ ID NO 110
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gagctcgtgc tgctcgaatt caagcttct             29

<210> SEQ ID NO 111
<211> LENGTH: 50
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (49)..(50)
<223> OTHER INFORMATION: a, c, g, t, unknown or other

<400> SEQUENCE: 111
tttggatttg ctggtgcagt acaactaggc gaggagcgtc tctccgacnn             50

```
<210> SEQ ID NO 112
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 112
gtcggagaga cgctcctcgc ctagttgtac tgcaccagca aatcc              45

<210> SEQ ID NO 113
<211> LENGTH: 50
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (49)..(50)
<223> OTHER INFORMATION: a, c, g, t, unknown or other

<400> SEQUENCE: 113
tttctgctcg aattcaagct tctaacgtac gaggagcgtc tctccgacnn         50

<210> SEQ ID NO 114
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 114
gtcggagaga cgctcctcgt acgttagaag cttgaattcg agcag              45

<210> SEQ ID NO 115
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gtgctcgtgg gatttgctgg tgcagtaca                                29

<210> SEQ ID NO 116
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gagctcgtgc tgctcgaatt caagcttct                                29

<210> SEQ ID NO 117
<211> LENGTH: 50
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (49)..(50)
```

<223> OTHER INFORMATION: a, c, g, t, unknown or other

<400> SEQUENCE: 117
tttggatttg ctggtgcagt acaactaggc gaggagcgtc tctccgacnn    50

<210> SEQ ID NO 118
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 118
gtcggagaga cgctcctcgc ctagttgtac tgcaccagca aatcc    45

<210> SEQ ID NO 119
<211> LENGTH: 50
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: modified_base
<222> LOCATION: (49)..(50)
<223> OTHER INFORMATION: a, c, g, t, unknown or other

<400> SEQUENCE: 119
tttctgctcg aattcaagct tctaacgtac gaggagcgtc tctccgacnn    50

<210> SEQ ID NO 120
<211> LENGTH: 45
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 120
gtcggagaga cgctcctcgt acgttagaag cttgaattcg agcag    45

<210> SEQ ID NO 121
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gtgctcgtgg gatttgctgg tgcagtaca    29

<210> SEQ ID NO 122
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gagctcgtgc tgctcgaatt caagcttct    29

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(19)
<223> OTHER INFORMATION: a, c, g, t, unknown or other

<400> SEQUENCE: 123
ggatgcatgn nnnnnnnnn                                                      19

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, g, t, unknown or other

<400> SEQUENCE: 124
nnnnnnnnnn catgcatcc                                                      19

<210> SEQ ID NO 125
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(29)
<223> OTHER INFORMATION: a, c, g, t, unknown or other

<400> SEQUENCE: 125
ggatgcatgn nnnnnnnnn nnnnnnnnnc atgcatcc                                  38

<210> SEQ ID NO 126
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(29)
<223> OTHER INFORMATION: a, c, g, t, unknown or other

<400> SEQUENCE: 126
ggatgcatgn nnnnnnnnn nnnnnnnnnc atgcatcc                                  38

<210> SEQ ID NO 127
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(24)
<223> OTHER INFORMATION: a, c, g, t, unknown or other
<220> FEATURE:
<221> NAME/KEY: modified_base
<222> LOCATION: (29)..(38)
<223> OTHER INFORMATION: a, c, g, t, unknown or other

<400> SEQUENCE: 127
catgnnnnnn nnnnnnnnnn nnnncatgnn nnnnnnnnca tg                             42

<210> SEQ ID NO 128
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(14)
<223> OTHER INFORMATION: a, c, g, t, unknown or other
<220> FEATURE:
<221> NAME/KEY: modified_base
<222> LOCATION: (19)..(38)
<223> OTHER INFORMATION: a, c, g, t, unknown or other

<400> SEQUENCE: 128
catgnnnnnn nnnncatgnn nnnnnnnnnn nnnnnnnnca tg                             42

<210> SEQ ID NO 129
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
aaaaaaaaaa aaaa                                                            14

<210> SEQ ID NO 130
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
aaaaaaaaaa aaaaaa                                                          16

<210> SEQ ID NO 131
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gcggccgctt tttttt                                                          17

<210> SEQ ID NO 132
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
cgccggcgtt tttttt                                                          17

<210> SEQ ID NO 133
<211> LENGTH: 17

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aaaaaaaaag cggccgc                                                      17

<210> SEQ ID NO 134
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
aaaaaaaaag c                                                            11

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(20)
<223> OTHER INFORMATION: a, c, g, t, unknown or other

<400> SEQUENCE: 135
aaaaaaaaag cggccgcnnn                                                   20

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, g, t, unknown or other

<400> SEQUENCE: 136
nnngcggccg cttttttttt t                                                 21

<210> SEQ ID NO 137
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(38)
<223> OTHER INFORMATION: a, c, g, t, unknown or other

<400> SEQUENCE: 137
gaggagcgtc tctccgacnn nnnnnnnnnn nnnnnnn                                38

<210> SEQ ID NO 138
<211> LENGTH: 36
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(18)
<223> OTHER INFORMATION: a, c, g, t, unknown or other

<400> SEQUENCE: 138
nnnnnnnnnn nnnnnnnngt cggagagacg ctcctc                                   36

<210> SEQ ID NO 139
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(38)
<223> OTHER INFORMATION: a, c, g, t, unknown or other

<400> SEQUENCE: 139
gaggagcgtc tctccgacnn nnnnnnnnnn nnnnnnnn                                 38

<210> SEQ ID NO 140
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(18)
<223> OTHER INFORMATION: a, c, g, t, unknown or other

<400> SEQUENCE: 140
nnnnnnnnnn nnnnnnnngt cggagagacg ctcctc                                   36

<210> SEQ ID NO 141
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(56)
<223> OTHER INFORMATION: a, c, g, t, unknown or other

<400> SEQUENCE: 141
gaggagcgtc tctccgacnn nnnnnnnnnn nnnnnnnnnn nnnnnnnnnn nnnnnngtcg         60
gagagacgct cctc                                                           74

<210> SEQ ID NO 142
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(56)
<223> OTHER INFORMATION: a, c, g, t, unknown or other

<400> SEQUENCE: 142
gaggagcgtc tctccgacnn nnnnnnnnnn nnnnnnnnnn nnnnnnnnnn nnnnnngtcg         60
```

```
gagagacgct cctc                                                       74

<210> SEQ ID NO 143
<211> LENGTH: 420
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(42)
<223> OTHER INFORMATION: a, c, g, t, unknown or other
<220> FEATURE:
<221> NAME/KEY: modified_base
<222> LOCATION: (47)..(84)
<223> OTHER INFORMATION: a, c, g, t, unknown or other
<220> FEATURE:
<221> NAME/KEY: modified_base
<222> LOCATION: (89)..(126)
<223> OTHER INFORMATION: a, c, g, t, unknown or other
<220> FEATURE:
<221> NAME/KEY: modified_base
<222> LOCATION: (131)..(168)
<223> OTHER INFORMATION: a, c, g, t, unknown or other
<220> FEATURE:
<221> NAME/KEY: modified_base
<222> LOCATION: (173)..(210)
<223> OTHER INFORMATION: a, c, g, t, unknown or other
<220> FEATURE:
<221> NAME/KEY: modified_base
<222> LOCATION: (215)..(252)
<223> OTHER INFORMATION: a, c, g, t, unknown or other
<220> FEATURE:
<221> NAME/KEY: modified_base
<222> LOCATION: (257)..(294)
<223> OTHER INFORMATION: a, c, g, t, unknown or other
<220> FEATURE:
<221> NAME/KEY: modified_base
<222> LOCATION: (299)..(336)
<223> OTHER INFORMATION: a, c, g, t, unknown or other
<220> FEATURE:
<221> NAME/KEY: modified_base
<222> LOCATION: (341)..(378)
<223> OTHER INFORMATION: a, c, g, t, unknown or other
<220> FEATURE:
<221> NAME/KEY: modified_base
<222> LOCATION: (383)..(420)
<223> OTHER INFORMATION: a, c, g, t, unknown or other

<400> SEQUENCE: 143 cgacnnnnn nnnnnnnnnn nnnnnnnnnn nnnnnnnnnn nncgacnnnn nnnnnnnnnn        60
nnnnnnnnnn nnnnnnnnnn nnnncgacnn nnnnnnnnnn nnnnnnnnnn nnnnnnnnnn       120 nnnnncgac nnnnnnnnnn nnnnnnnnnn nnnnnnnnnn nnnnnnnncg acnnnnnnnn        180
nnnnnnnnnn nnnnnnnnnn nnnnnnnnnn cgacnnnnnn nnnnnnnnnn nnnnnnnnnn       240
nnnnnnnnnn nncgacnnnn nnnnnnnnnn nnnnnnnnnn nnnnnnnnnn nnnncgacnn       300
nnnnnnnnnn nnnnnnnnnn nnnnnnnnnn nnnnncgac nnnnnnnnnn nnnnnnnnnn        360
nnnnnnnnnn nnnnnnnncg acnnnnnnnn nnnnnnnnnn nnnnnnnnnn nnnnnnnnnn       420

<210> SEQ ID NO 144
<211> LENGTH: 420
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(38)
<223> OTHER INFORMATION: a, c, g, t, unknown or other
```

```
<220> FEATURE:
<221> NAME/KEY: modified_base
<222> LOCATION: (43)..(80)
<223> OTHER INFORMATION: a, c, g, t, unknown or other
<220> FEATURE:
<221> NAME/KEY: modified_base
<222> LOCATION: (85)..(122)
<223> OTHER INFORMATION: a, c, g, t, unknown or other
<220> FEATURE:
<221> NAME/KEY: modified_base
<222> LOCATION: (127)..(164)
<223> OTHER INFORMATION: a, c, g, t, unknown or other
<220> FEATURE:
<221> NAME/KEY: modified_base
<222> LOCATION: (169)..(206)
<223> OTHER INFORMATION: a, c, g, t, unknown or other
<220> FEATURE:
<221> NAME/KEY: modified_base
<222> LOCATION: (211)..(248)
<223> OTHER INFORMATION: a, c, g, t, unknown or other
<220> FEATURE:
<221> NAME/KEY: modified_base
<222> LOCATION: (253)..(290)
<223> OTHER INFORMATION: a, c, g, t, unknown or other
<220> FEATURE:
<221> NAME/KEY: modified_base
<222> LOCATION: (295)..(332)
<223> OTHER INFORMATION: a, c, g, t, unknown or other
<220> FEATURE:
<221> NAME/KEY: modified_base
<222> LOCATION: (337)..(374)
<223> OTHER INFORMATION: a, c, g, t, unknown or other
<220> FEATURE:
<221> NAME/KEY: modified_base
<222> LOCATION: (379)..(416)
<223> OTHER INFORMATION: a, c, g, t, unknown or other

<400> SEQUENCE: 144
nnnnnnnnnn nnnnnnnnnn nnnnnnnnnn nnnnnnnngt cgnnnnnnnn nnnnnnnnnn      60
nnnnnnnnnn nnnnnnnnnn gtcgnnnnnn nnnnnnnnnn nnnnnnnnnn nnnnnnnnnn     120
nngtcgnnnn nnnnnnnnnn nnnnnnnnnn nnnnnnnnnn nnnngtcgnn nnnnnnnnnn     180
nnnnnnnnnn nnnnnnnnnn nnnnnngtcg nnnnnnnnnn nnnnnnnnnn nnnnnnnnnn     240
nnnnnnnngt cgnnnnnnnn nnnnnnnnnn nnnnnnnnnn nnnnnnnnnn gtcgnnnnnn     300
nnnnnnnnnn nnnnnnnnnn nnnnnnnnnn nngtcgnnnn nnnnnnnnnn nnnnnnnnnn     360
nnnnnnnnnn nnngtcgnn nnnnnnnnnn nnnnnnnnnn nnnnnnnnnn nnnnnngtcg     420

<210> SEQ ID NO 145
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (42)..(42)
<223> OTHER INFORMATION: a, c, g, t, unknown or other

<400> SEQUENCE: 145
gactagttct agatcgcgag gccggccttt tttttttttt vn                          42

<210> SEQ ID NO 146
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
```
aaaaaaaaaa aaaggccggc ctcgcgatct agaactagtc                                    40

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tcggatcgcg atctagaact agtc                                                     24

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gactagttct agatcgcgat ccgaccgg                                                 28

<210> SEQ ID NO 149
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
aaaaaaaaaa aaaggccggt cggatcgcga tctagaacta gtc                                43

<210> SEQ ID NO 150
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gactagttct agatcgcgat ccgaccggcc ttttttttt ttt                                 43

<210> SEQ ID NO 151
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(18)
<223> OTHER INFORMATION: a, c, g, t, unknown or other

<400> SEQUENCE: 151
nnnnnnnnnn nnnnnnnngt cggagagacg ctcctc                                        36

<210> SEQ ID NO 152
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (19)..(38)
<223> OTHER INFORMATION: a, c, g, t, unknown or other

<400> SEQUENCE: 152
gaggagcgtc tctccgacnn nnnnnnnnnn nnnnnnnn                                    38

<210> SEQ ID NO 153
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(18)
<223> OTHER INFORMATION: a, c, g, t, unknown or other

<400> SEQUENCE: 153
nnnnnnnnnn nnnnnnnngt cggagagacg ctcctc                                      36

<210> SEQ ID NO 154
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(38)
<223> OTHER INFORMATION: a, c, g, t, unknown or other

<400> SEQUENCE: 154
gaggagcgtc tctccgacnn nnnnnnnnnn nnnnnnnn                                    38

<210> SEQ ID NO 155
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (19)..(56)
<223> OTHER INFORMATION: n is a, c, g, or t

<400> SEQUENCE: 155
gaggagcgtc tctccgacnn nnnnnnnnnn nnnnnnnnnn nnnnnnnnnn nnnnnngtcg            60
gagagacgct cctc                                                              74

<210> SEQ ID NO 156
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (19)..(56)
<223> OTHER INFORMATION: n is a, c, g, or t

<400> SEQUENCE: 156
gaggagcgtc tctccgacnn nnnnnnnnnn nnnnnnnnnn nnnnnnnnnn nnnnnngtcg            60
gagagacgct cctc                                                              74
```

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gcggccgctt tttttttt                                                       18

<210> SEQ ID NO 158
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ggccgctttt tttttt                                                         16

<210> SEQ ID NO 159
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gactagttct agatcgcgag gccggccttt tttttttttt                               40

<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
aaaaaaaaaa aaaggccgg                                                      19

<210> SEQ ID NO 161
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161 ccttttttttt ttttt                                                         15

<210> SEQ ID NO 162
<211> LENGTH: 126
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(122)
<223> OTHER INFORMATION: a, c, g, t, unknown or other and this region
      may encompass 12-120 bases, preferably between 18-46
      bases, preferably 40 bases

```
<400> SEQUENCE: 162
acnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120 nngtcg                                                                126

<210> SEQ ID NO 163
<211> LENGTH: 126
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(122)
<223> OTHER INFORMATION: a, c, g, t, unknown or other and this region
      may encompass 12-120 bases, preferable between 18-46
      bases, preferably 40 bases

<400> SEQUENCE: 163
acnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120 nngtcg                                                                126

<210> SEQ ID NO 164
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(44)
<223> OTHER INFORMATION: a, c, g, t, unknown or other

<400> SEQUENCE: 164
tccgacnnnn nnnnnnnnnn nnnnnnnnnn nnnnnnnnnn nnnn                       44

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(24)
<223> OTHER INFORMATION: a, c, g, t, unknown or other

<400> SEQUENCE: 165
gaggagnnnn nnnnnnnnnn nnnn                                             24
```

METHOD TO GENERATE OR DETERMINE NUCLEIC ACID TAGS CORRESPONDING TO THE TERMINAL ENDS OF DNA MOLECULES USING SEQUENCES ANALYSIS OF GENE EXPRESSION (TERMINAL SAGE)

INCORPORATION BY REFERENCE

This application is a continuation-in-part application of international patent application Serial No. PCT/SG2003/000255 filed Dec. 4, 2003, which published as International Publication Number WO 2004/050918 on Jun. 17, 2004, which claims benefit of GB application Serial No. GB0228289.5 filed Dec. 4, 2002.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the field of biology, in particular, the fields of molecular biology, genomics, genome annotation, gene expression, transcriptome analysis and diagnostics. In particular, the present invention relates to a method of Serial Analysis of Gene Expression (SAGE).

BACKGROUND OF THE INVENTION

One the most burdensome tasks in the post genome-sequencing era is the accurate and complete annotation of all genes and their products, primarily mRNA transcripts of a sequenced genome. Bioinformatics analyses of fragmentary experimental data have led to widely varying estimates of the number of human genes. Human EST assembly resulted in 89,000 Unigene clusters; ab initio genome annotation identified approximately 30,000 genes by two independent studies; and the manually curated RefSeq database has only 17,000 genes identified with stringent evidences. It is apparent that current technologies applied for genome annotation including computational gene prediction, cDNA cloning and sequencing, and other new technologies are inefficient, incomplete, and unconvincing.

Computational methods including homology studies, domain searches, and ab initio gene predictions have great limitation and fallibility. Current prediction programs may be fine for many 'internal' exons, but perform particularly poorly on border exons in UTR regions. They need to be trained by more experimental data. The precise annotation of every gene in complex genomes by computation methods alone is still a distant goal.

Although cDNA cloning and sequencing, including EST, full-length, and OFESTES, have generated immense data in EST and full-length cDNA sequences, low abundance and large size transcripts are discriminated against during cloning steps. Library-based cDNA approaches are incomplete for identifying all transcripts due to high redundancy of abundant transcripts and high percentage of truncated clones. A comprehensive cDNA library approach may be efficient for capturing the first 50-70% of all expressed transcripts, but it soon becomes prohibitively expensive and inefficient for getting the rest, in particular the rare transcripts.

Genome-wide scans by oligonucleotide microarrays provide another strategy that has the potential to help annotate complex genomes. In this approach, oligo probes representing predicted exons are synthesized, micro-arrayed, and subsequently hybridised to mRNA samples. Experimental data generated would provide validations to true exons. This approach is expected to be efficient to examine many different biological stages and environmental conditions for expressed transcripts. However, a major limitation of this method is its ability to convincingly determine the existence of rare genes because the signal detection sensitivity of probe hybridization is limited.

Serial Analysis of Gene Expression (SAGE) represents a unique strategy to identify the existence of transcripts and quantify them by counting a small tag for each transcript molecule in a complex transcriptome. Three principles underlie the SAGE methodology: (1) A short sequence tag (10-14 bp) contains sufficient information to uniquely identify a transcript provided that that the tag is obtained from a unique position within each transcript; (2) Sequence tags can be linked together to from long serial molecules that can be cloned and sequenced; and (3) Quantitation of the number of times a particular tag is observed provides the expression level of the corresponding transcript. The unique feature of SAGE is that a 14-bp sequence is enough to be transcript specific and small tags from each transcript can be extracted and concatenated into larger pieces for efficient sequencing analysis. Because of all transcripts are represented by small tags in same size, there is no discrimination in SAGE tag cloning. Essentially all transcripts should be represented in SAGE tags.

SAGE is described in U.S. Pat. Nos. 5,695,937, 5,866,330 and 6,383,743, and is illustrated in FIGS. 1A and 1B, and also in Velculescu, V. E., Zhang, L., Vogelstein, B., and Kinzler, K. W. (1995). Serial Analysis Of Gene Expression. Science 270, 484-487, as well as Velculescu, V. E., Zhang, L., Zhou, W., Vogelstein, J., Basrai, M. A., Bassett, D. E., Hieter, P., Vogelstein, B., and Kinzler, K. W. (1997). Characterization of the yeast transcriptome. Cell 88. A number of websites devoted to SAGE may also be consulted for teachings on this technique, including the Sagenet website and Sagemap on the National Center for Biotechnology Information's website (a public gene expression data repository and online data access and analysis site, see Lash A E, Tolstoshev C M, Wagner L, Schuler G D, Strausberg R L, Riggins G J, Altschul S F. (2000) SAGEmap: a public gene expression resource. Genome Res 2000 July; 10(7):1051-60). Other websites describing SAGE and its uses may be found by conducting an internet search for Serial Analysis of Gene Expression.
http://www.google.com/
search?sourceid=navclient&ie=UTF-8&oe=UTF-8&q=Serial+Analysis+of+Gene+Expression In brief, mRNA is obtained from a cell or tissue, and reverse transcribed to obtain cDNA (see FIG. 1). The cDNA is then cleaved by a first restriction enzyme (the "Anchoring Enzyme", typically a 4-base cutter), and the 3' end of the cDNA is anchored to a bead. The beads are optionally divided into two pools, and the cDNA attached to the beads is ligated to two sets of adaptors or linkers. Each of these adaptors comprises a defined nucleotide sequence for PCR priming and amplification at its 5' end, as well as a recognition site for a type IIS enzyme (the "Tagging Enzyme", for example BsmFI and FokI), which directs cleavage by the enzyme at a position 3' downstream of the recognition site. The tags are released by cleavage with the relevant Tagging Enzyme, and ligated together end to end to form ditags. The ditags are then amplified using PCR, digested with the Anchoring Enzyme, and ligated together to form concatamers. Sequencing of the concatamers reveals the identity and frequency of the tags, and provides expression data for the various genes which are transcribed in the cell or tissue. Due to the efficiency of sequencing small tags, SAGE has the potential to capture all expressed transcripts.

Despite these promises however, the original SAGE tags are too short for direct mapping to complex genomes. The 14-bp tags are only reliable for mapping onto existing EST or cDNA sequences in databases, or small genomes such as yeast. This shortcoming limits the application of SAGE to use only as an expression profiling tool, not for genome annotation. To overcome this problem, the developers of the original method managed to make the SAGE tags longer, simply by taking the advantage of a new IIS enzyme MmeI that cleaves DNA 20 base pairs away from its recognition site. The modified method is known as LongSAGE, and is described in WO 02/10438. This modification makes the LongSAGE tags specific enough to be directly mapped onto human chromosome sequences (Table 1 in Appendix B). This function is an important addition because new SAGE tags now can be directly marked onto specific chromosome locations for potential new genes or exons identifications, therefore, facilitating genome annotations.

However, despite its advantages, LongSAGE still has limitations to its effective use. Like the original SAGE, LongSAGE tags are extracted randomly depending on where the NlaIII sites are in a transcript sequence, so providing only 'internal' sequence clues for new transcripts. Furthermore, the new SAGE tags identified have to go through very tedious and long process such as 5' and 3' RACE to extend the information about the existence and characteristics of new genes. Finally, only one tag is generated for each expressed sequence, and it is not possible with the prior art methods to obtain further sequence information for the expressed gene readily.

The present invention seeks to solve these and other problems in the prior art techniques for expression analysis.

Citation or identification of any document in this application is not an admission that such document is available as prior art to the present invention.

SUMMARY OF THE INVENTION

Previously described SAGE and LongSAGE techniques have disadvantages. In particular, particular disadvantages arise from the fact that the tags obtained in the prior art techniques reflect internal sequences of the expressed genes.

The usefulness of obtaining sequence tags from the 5' and 3' termini of transcripts has not previously been recognized. On the other hand, such terminal tags have advantages in that they can be used to define the boundary regions of genes. In addition, the full-length coding sequence of unknown genes may easily be obtained by PCR, once the sequence tags from the 5' and 3' termini of the transcribed region are known. Furthermore, obtaining a 5' terminal transcribed sequence in a tag can provide a handle for promoter identification, as described below.

The present invention therefore provide methods and compositions for obtaining tags corresponding to 5' and 3' terminal transcribed sequences of expressed genes, i.e., tags corresponding to the 5' and 3' termini of transcripts. The present invention also provide methods of obtaining further sequence information in the form of further sequence tags from expressed genes, which may be conduced in a repetitive or iterative manner.

According to a first aspect of the present invention, a method of providing an indication of an instance of expression of a gene is provided, wherein the method may comprise the steps of: (a) providing a complementary deoxyribonucleic acid (cDNA); (b) linking the cDNA to an linker sequence thereby forming a linked nucleic acid, in which the linker sequence may comprise a first recognition site for a first nucleic acid cleavage enzyme, preferably a restriction endonuclease, that allows nucleic acid cleavage at a site distant from the first recognition site; and (c) cleaving the linked nucleic acid with the first nucleic acid cleavage enzyme to provide a linked tag, in which the linked tag comprises a nucleotide sequence tag representative of a terminal transcribed sequence of the gene; and (d) detecting the presence or identity of the linked tag or the nucleotide sequence tag to provide an indication of an instance of gene expression.

In a preferred embodiment, the 5' end of the cDNA may comprise a sequence corresponding to the 5' terminal transcribed sequence of the gene, and the linker sequence is linked to the 5' end of the cDNA. Preferably, the nucleotide sequence tag may comprise a 5' terminal transcribed sequence of the gene, preferably at least the first 16 bases of the transcribed portion, more preferably the first 20 bases of the transcribed portion of the gene.

In a further preferred embodiment, the 3' end of the cDNA may comprise a sequence corresponding to the 3' terminal transcribed sequence of the gene, and the linker sequence may be linked to the 3' end of the cDNA. Preferably, the nucleotide sequence tag may comprise a 3' terminal transcribed sequence of the gene, preferably at least the last 16 bases of the transcribed portion, more preferably the last 20 bases of the transcribed portion of the gene.

Preferably, step (a) may comprise: (i) deriving a cDNA from an mRNA by reverse transcription with an primer comprising a sequence 5'-NV(T)$^{13}$CCGGCCGG-3' (SEQ ID NO: 4), in which N=A, C, G or T and V=A, C or G; (ii) producing a double stranded cDNA therefrom and digesting the double stranded cDNA with FseI to produce a cleaved cDNA which may comprise a

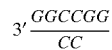

overhang; (iii) linking the cleaved cDNA to a linker which may comprise

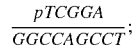

and (iv) cleaving the resulting molecule with MmeI to produce a cDNA lacking a polyA/T tail.

In highly preferred embodiments, the cDNA may comprise the 5' terminal transcribed sequence of the gene, or the 3' terminal transcribed sequence of the gene, or both. Preferably, the cDNA is full length cDNA, which preferably may comprise substantially all the coding sequence of the gene. The cDNA may in some embodiments be processed such that it does not comprise any untranslated regions, such as 5' UTR and/or 3' UTR. Specifically, in preferred embodiments, the cDNA does not comprise a portion of, preferably does not comprise the whole of, the polyA/T tail.

There is provided, according to a second aspect of the present invention, a method of obtaining sequential sequence information from a gene, the method which may comprise steps (a) to (c) of a method according to the first aspect of the invention, or any preferred embodiments, the method which may further comprise: (d) providing a second nucleic acid from step (c) comprising 3' remaining sequences of the cDNA; (e) linking the second nucleic acid to an linker sequence, thereby forming a linked nucleic acid, in which the linker sequence comprises a recognition site for a nucleic acid cleavage enzyme, preferably a restriction endonuclease, that allows nucleic acid cleavage at a site distant from the recognition site; (f) cleaving the linked nucleic acid with the nucleic acid cleavage enzyme to provide: (i) a linked tag comprising the linker sequence linked to a nucleotide sequence tag comprising a 5' portion of the second nucleic acid; and (ii) a fourth nucleic acid sequence comprising a 3' remainder portion of third nucleic acid; (g) repeating steps (d) to (f) at least once, in which the second nucleic acid sequence of step (d) is provided by the fourth nucleic acid sequence of step (f)(ii); and (h) detecting the presence, identity or sequence of at least one linked tag or a nucleotide sequence tag comprised therein.

This aspect of the invention enables "walking" along the cDNA, i.e., the ability to obtain a further nucleotide sequence tag comprising further sequence internal to the terminus, which is offset from the first nucleotide sequence tag initially obtained. Further rounds may be carried out to sequentially obtain further nucleotide sequence tags.

In preferred embodiments, the linker sequence further may comprise a second recognition site for a second nucleic acid cleavage enzyme, preferably a second restriction endonuclease, that allows nucleic acid cleavage at a site distant from the second recognition site, and in which the second recognition site is located 5' of the first recognition site in the linker sequence.

In such embodiments, the location of the second recognition site with respect to the first recognition site may be such that, when the linked tag is exposed to the second nucleic acid cleavage enzyme, cleavage of the nucleic acid occurs at a position within or about the first recognition site.

Preferably, the first recognition site or the second recognition site, or both, may comprise a Type IIS restriction enzyme recognition site.

Preferably, the first recognition site may comprise a MmeI recognition site 5'-TCC RAC-3', preferably 5'-TCC GAC-3'. Preferably, the second recognition site may comprise a BseRI recognition site 5'-GAGGAG-3'.

Preferably, the linker sequence may comprise the sequence 5'-GAGGAGNNNNNNTC.CG˙AC-3' (SEQ ID NO: 1), preferably 5'-GAGGAGCGTCTCTCCGAC-3' (SEQ ID NO: 2).

A third aspect of the present invention provides for a method of detecting expression of a gene, wherein the method may comprise: (a) providing a first linked tag and a second linked tag, each independently produced by a method according to the first or second aspect of the invention, including preferred embodiments; (b) linking the first linked tag and the second linked tag such that the nucleotide sequence tag portion of one linked tag is linked to the nucleotide sequence tag of the other linked tag to form a ditag, the ditag comprising terminal transcribed sequences from first and second genes; and (c) detecting the presence or identity of the ditag, or at least one nucleotide sequence tag comprised therein, to detect gene expression.

Preferably, each of the first linker sequence of the first linked tag and the second linker sequence of the second linked tag may comprise an amplification primer hybridisation sequence. Accordingly, in preferred embodiments, the method further may comprise a step of amplifying the ditag, preferably by means of the polymerase chain reaction (PCR).

Preferably, the method further may comprise the step of cleaving the ditag with the or each second nucleic acid cleavage enzyme to provide a trimmed ditag.

The trimmed ditag may comprise between 12 to 120 base pairs, preferably between 18 to 46 base pairs, preferably 40 base pairs.

Preferably, a plurality of ditags or trimmed ditags are linked to form a concatamer. The concatamer may comprise between 2 to 200 ditags or trimmed ditags, preferably between 8 to 20 ditags or trimmed ditags.

The method may further comprise the step of determining the sequence of a or each linked tag, nucleotide sequence tag, ditag, trimmed ditag or concatamer. A further step of determining the identity of the expressed gene by the comparing the sequence to a nucleotide sequence comprised in a database of nucleotide sequences may also be included. The sequence may be compared to a database of known genes, such that if the database does not comprise the sequence, the sequence comprises a new gene.

As a fourth aspect of the present invention, there is provided a method of providing an indication useful in the diagnosis of a disease in an individual, wherein the method may comprise: (a) providing a cell known to be affected by the disease; (b) determining if a gene is expressed in the cell of (b) by a method according to any preceding aspect of the invention; (c) providing a cell of an individual suspected of suffering from the disease; and (d) determining whether the same gene is expressed in the cell of (c) by a method according to any preceding aspect of the invention; and (e) comparing the expression, or lack thereof, of the gene between the cell of (b) and the cell of (c).

The present invention, in a sixth aspect, provides a method of producing determining the transcriptome of a cell, or obtaining a gene expression profile of a cell, wherein the method may comprise providing cDNA from the cell, subjecting said cDNA to a method according to any preceding aspect of the invention, and determining whether a particular gene, or a particular set of genes, is expressed by the cell.

A seventh aspect of the present invention relates to a method of providing an indication useful in the diagnosis of a disease in an individual, wherein the method may comprise comparing the gene expression profile of a cell known to be affected by the disease, with a cell of an individual suspected of suffering from the disease, in which either or both of the gene expression profiles are produced by a method according to sixth aspect of the invention.

An eighth aspect of the present invention provides a method of determining the sequence of a control sequence of a gene, preferably a promoter or enhancer sequence, wherein the method may comprise: (a) obtaining a nucleotide sequence tag representative of the 5' terminal transcribed sequence of the gene by a method according to the first aspect of the invention, or any preferred embodiments; and (b) obtaining a sequence of the gene 5' to the terminal transcribed sequence of (a) comprising a promoter or enhancer consensus sequence.

In a preferred embodiment, the sequence of the gene 5' to the terminal transcribed sequence of (a) may be obtained by means of (a) chromosome walking, (b) SAGE walking, (c) nucleic acid hybridisation of a genomic library; or (d) querying a database of genomic sequences.

A ninth aspect of the invention provides for a database comprising a plurality of records, each record comprising an indication whether a gene is expressed by a particular cell, which indication is provided by a method according to any preceding aspect of the invention.

There is provided, in accordance with a tenth aspect of the present invention, a computer readable medium comprising a database according to the ninth aspect of the invention.

As an eleventh aspect of the invention, a nucleic acid sequence which may comprise a tag produced by a method according to any preceding aspect of the invention is provided.

According to a twelfth aspect of the invention, there is provided a nucleic acid sequence comprising a ditag produced by a method according to any preceding aspect of the invention.

According to a thirteenth aspect of the present invention, a nucleic acid sequence which may comprise a concatamer which may comprise a plurality of such tags or such ditags is provided.

There is provided, according to a fourteenth aspect of the present invention, a gene identified by a method according to any preceding aspect of the invention, or a protein encoded by the gene.

A control sequence, preferably a promoter sequence, identified by a method according to any preceding aspect of the invention.

According to a thirteenth aspect of the present invention, a nucleic acid sequence which may comprise: (a) a recognition site for a nucleic acid cleavage enzyme, preferably a restriction endonuclease, that allows nucleic acid cleavage at a site distant from the first recognition site, and (b) a nucleotide sequence tag representative of a terminal transcribed sequence of a gene is provided.

The nucleic acid sequence may further comprise: (c) a second recognition site in which the second recognition site is for a second nucleic acid cleavage enzyme, preferably a second restriction endonuclease, that allows nucleic acid cleavage at a site distant from the second recognition site, and in which the cleavage site for the second nucleic acid cleavage enzyme is located within or about the first recognition site.

Alternatively, or in addition, the nucleic acid sequence may further comprise: (c) a second recognition site 5' of the first recognition site, in which the second recognition site is for a second nucleic acid cleavage enzyme, preferably a second restriction endonuclease, that allows nucleic acid cleavage at a site distant from the second recognition site, and in which the first recognition site and the second recognition site are spaced such that when the nucleic acid is exposed to the second nucleic acid cleavage enzyme, cleavage of the nucleic acid occurs at a position within or about the first recognition site.

A linker sequence which may comprise: (a) a first recognition site for a nucleic acid cleavage enzyme, preferably a restriction endonuclease, that allows nucleic acid cleavage at a site distant from the first recognition site; (c) a second recognition site for a second nucleic acid cleavage enzyme, preferably a second restriction endonuclease, that allows nucleic acid cleavage at a site distant from the second recognition site; in which in which the cleavage site for the second nucleic acid cleavage enzyme is located within or about the first recognition site is provided.

Preferably, the nucleic acid sequence comprises the sequence 5'-GAGGAGNNNNNNTC.CG'AC-3' (SEQ ID NO: 1), preferably 5'-GAGGAGCGTCTCTCCGAC-3' (SEQ ID NO: 2).

According to a fourteenth aspect of the present invention, a method for detecting expression of a gene is provided, wherein the method may comprise the steps of: (a) providing a first complementary deoxyribonucleic acid (cDNA); (b) providing a second complementary deoxyribonucleic acid (cDNA); (c) linking the first cDNA so produced to a first linker sequence thereby forming a first linked nucleic acid, in which the first linker sequence comprises a first recognition site for a first nucleic acid cleavage enzyme, preferably a first restriction endonuclease, that allows nucleic acid cleavage at a site distant from the first recognition site; (d) linking the second cDNA so produced to a second linker sequence thereby forming a second linked nucleic acid, in which the second linker sequence comprises a second recognition site for a second nucleic acid cleavage enzyme, preferably a second restriction endonuclease, that allows nucleic acid cleavage at a site distant from the second recognition site; (e) cleaving the first linked nucleic acid with the first nucleic acid cleavage enzyme to provide a first linked tag, in which the first linked tag comprises a first nucleotide sequence tag representative of a terminal transcribed sequence of the first cDNA. (f) cleaving the second linked nucleic acid with the second nucleic acid cleavage enzyme to provide a second linked tag, in which the second linked tag comprises a second nucleotide sequence tag representative of a terminal transcribed sequence of the second cDNA. (g) ligating the first and second tags to form a ditag; and (h) determining the nucleotide sequence of at least one tag of the ditag to detect gene expression.

According to a fifteenth aspect of the present invention, a method of sequentially generating subsequences from a nucleic acid sequence is provided, the method which may comprise the steps of: (a) providing a first nucleic acid sequence; (b) linking the first nucleic acid sequence to an second nucleic acid sequence to form a linked nucleic acid, in which the second nucleic acid sequence comprises a recognition site for a nucleic acid cleavage enzyme that allows cleavage of the first nucleic acid sequence at a site distant from the recognition site; and (c) cleaving the linked nucleic acid with the nucleic acid cleavage enzyme to provide: (i) a third nucleic acid sequence comprising the second nucleic acid linked to a subsequence of the first nucleic acid sequence, which subsequence comprises a 5' portion of the first nucleic acid sequence; and (ii) a fourth nucleic acid sequence comprising a 3' remainder portion of the first nucleic acid sequence; (d) repeating steps (a) to (c) at least once, in which the first nucleic acid sequence of step (a) is provided by the fourth nucleic acid sequence of step (c)(ii); and (e) detecting the presence, identity or sequence of at least one third nucleic acid sequence or a 5' portion of a first nucleic acid sequence comprised therein.

According to a sixteenth aspect of the present invention, a method of obtaining a nucleotide sequence tag from a terminus of a nucleic acid is provided, wherein the method may comprise the steps of: (a) providing a first nucleic acid sequence; (b) linking the first nucleic acid sequence to an linker sequence to form a linked nucleic acid, in which the linker sequence comprises: (i) a first recognition site for a first nucleic acid cleavage enzyme that allows cleavage of the first nucleic acid sequence at a site distant from the first recognition site, and (ii) a second recognition site for a second nucleic acid cleavage enzyme that allows nucleic acid cleavage at a site distant from the second recognition site, said cleavage site located at a position within or about the first recognition site; in which the linked nucleic acid has the structure: 5'—second recognition site-first recognition site-first nucleic acid-3' (c) cleaving the linked nucleic acid with the first nucleic acid cleavage enzyme to provide: (i) a linked tag comprising the linker sequence linked to a nucleotide sequence tag representative of the first nucleic acid sequence and comprising a terminal portion thereof; and (ii) a second nucleic acid sequence comprising a remainder portion of the first nucleic acid;

Preferably, the first nucleic acid may comprise a complementary deoxyribonucleic acid (cDNA) having a terminus comprising a 5' terminal transcribed sequence of a gene, and in which the linker sequence may be linked to said terminus.

Preferably, the first nucleic acid may comprise a complementary deoxyribonucleic acid (cDNA) having a terminus which may comprise a 3' terminal transcribed sequence of a gene, and in which the linker sequence is linked to said terminus.

Preferably, the second nucleic acid cleavage enzyme may comprise a restriction endonuclease, preferably a Type IIS restriction endonuclease, whose recognition site is 6 bases or greater, preferably MmeI.

Preferably, the first nucleic acid cleavage enzyme may comprise a restriction endonuclease, preferably a Type IIS restriction endonuclease, preferably BseRI.

There is provided, according to a seventeenth aspect of the present invention, a method of sequentially generating a plurality of nucleic acid sequences each of which may comprise a nucleotide sequence tag from a nucleic acid, the method comprising repeating steps (a) to (c) of any of the sixteenth aspects of the invention at least once, in which the first nucleic acid sequence of step (a) is provided by the second nucleic acid sequence of step (c)(ii).

According to a eighteenth aspect of the present invention, a method of providing an indication of an instance of expression of a gene is provided, wherein the method may comprise a method according to any preceding aspect of the invention, and may further comprise the step of detecting the presence, sequence or identity of the linked tag or the nucleotide sequence tag to provide an indication of an instance of gene expression.

According to a nineteenth aspect of the invention, a method of detecting gene expression is provided, wherein the method may comprise the steps of: (a) providing a first linked tag and a second linked tag, each independently produced by a method according to any preceding aspect of the invention; (b) linking the first linked tag and the second linked tag such that the nucleotide sequence tag portion of one linked tag is linked to the nucleotide sequence tag of the other linked tag to form a ditag, the ditag comprising terminal transcribed sequences from first and second genes; and (c) detecting the presence or identity of the ditag, or at least one nucleotide sequence tag comprised therein, to detect gene expression.

Preferably, each of the first and second linker sequences comprised in the first and second linked tags may comprise an amplification primer sequence, and in which the method further may comprise a step of amplifying the ditag, preferably by means of the polymerase chain reaction (PCR).

Preferably, the method further may comprise the steps of: (d) cleaving the ditag with the or each second nucleic acid cleavage enzyme; (e) linking a plurality of the resultant trimmed ditags to form a concatamer; and (f) obtaining the nucleic acid sequence of at least a portion of the concatamer.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

SEQUENCE LISTING

Figure 1A:
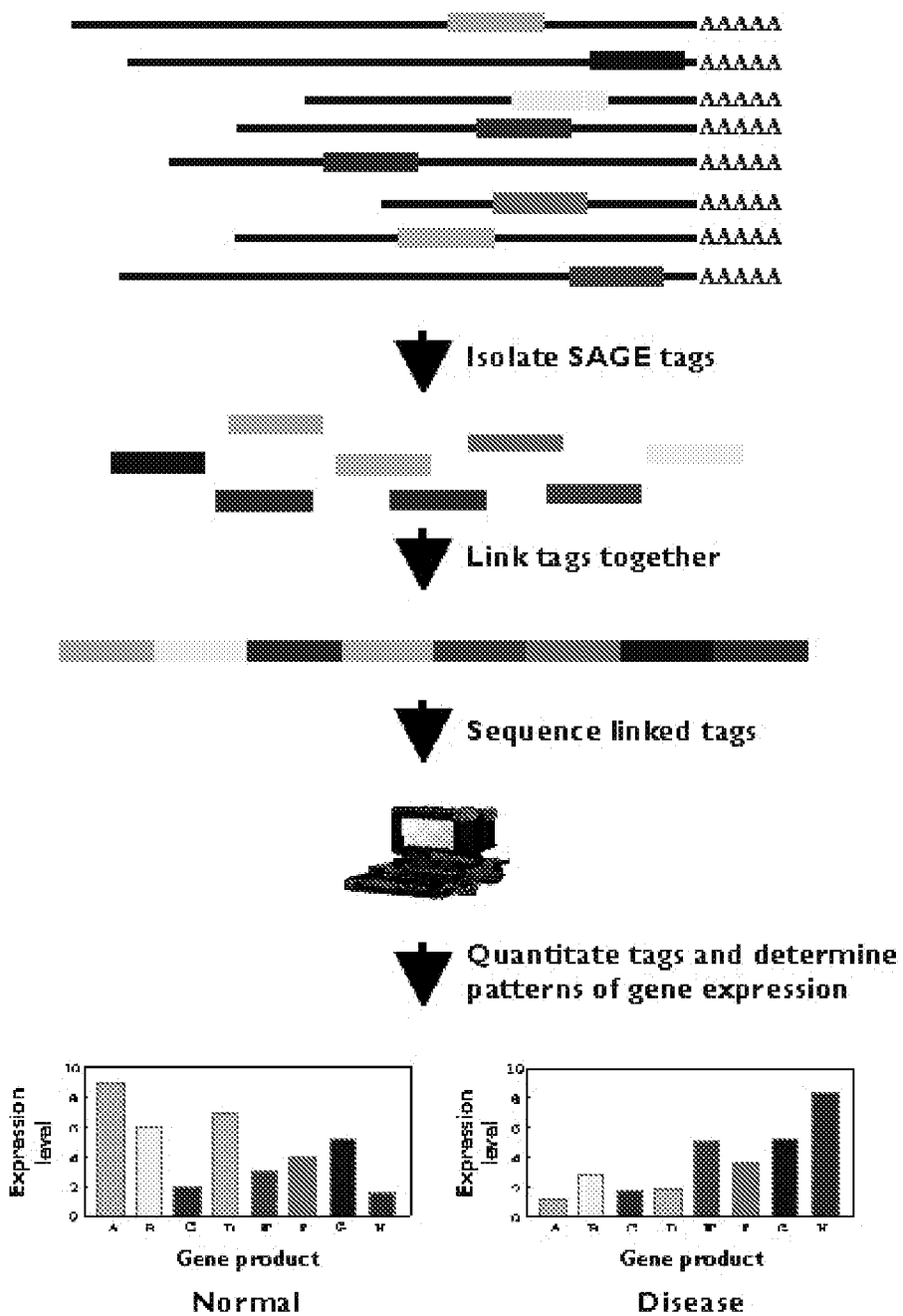
FIG. 1A shows an overview of a known SAGE technique. Immobilized cDNA fragments at 3'end on magnetic beads are digested by a 4-bp restriction enzyme NlaIII. On average, NlaIII cleaves along cDNA in every 250 base pairs. Linkers with a recognition site for BsmFI, a Type IIS type restriction enzyme, are ligated to the NlaIII cleaved end of cDNA fragments on the bead. BsmFI cuts the DNA asymmetrically [GTCCCN(14/10)] (SEQ ID NO: 3) resulting in the release of a 14 base pair tag representing the corresponding transcript. The extracted tags are then ligated into ditags for PCR amplification followed by removing the linker arms with NlaIII digestion. Ditags with 4-bp anchor sequence are concatenated, cloned, and sequenced.
Figure 1B:
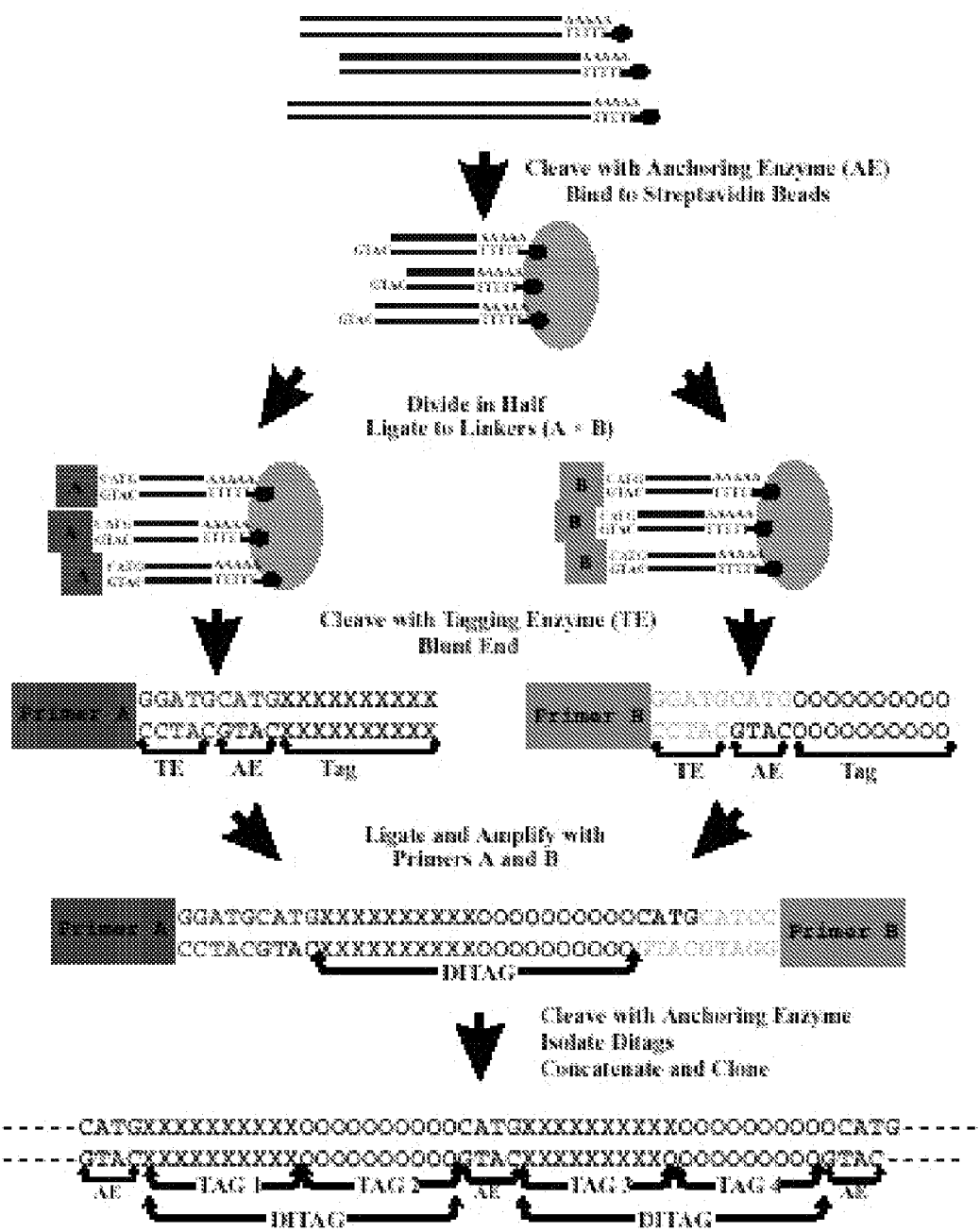
FIG. 1B is a schematic diagram of SAGE tag concatenate library construction. Figures discloses SEQ ID NOS: 123-128.

Appendix A shows the sequences of the various linkers and primers used in the methods and compositions described here, in particular in the Examples. The sequences shown are:

NotI-dT15 primer used for cDNA synthesis; Biotin-NotI linker; MmeI-BseRI Linker A (48 nt); MmeI-BseRI Linker B (48 nt); second round MmeI-BseRI Linker A (50 nt); second round MmeI-BseRI Linker B (50 nt); PCR primer A (29 nt, 20 nt); PCR primer B (29 nt, 20 nt); FseI-dT15 primer (for cDNA synthesis); 5' biotin linker (The biotin oligo is same as the PCR primer A); 1/2FseI-MmeI linker (to introduce MmeI site and remove polyA); Second round MmeI-BseRI Linker A (50 nt); Second round MmeI-BseRI Linker B (50 nt); PCR primer A (29 nt, 20 nt); PCR primer B (29 nt, 20 nt); NotI-dT20 primer; NotI Linker top; NotI Linker bottom; Linker A top (N5); Linker A top (N6); Linker A bottom; Linker B top (N5); Linker B top (N6); Linker B bottomx; PCR primer A; PCR primer B; GsuI-dT16 primer; MmeI-BseRI Linker A top; MmeI-BseRI Linker A bottom; MmeI-BseRI Linker B top;

MmeI-BseRI Linker B bottom; SalI adaptor top; SalI adaptor bottom; PCR primer A; PCR primer B. The methods and compositions described here may suitably employ any one or more of the sequences shown in the Sequence Listing.

DETAILED DESCRIPTION

The methods and compositions described here enable the isolation of defined nucleotide sequence tags from termini of nucleic acids. Methods for the detection of gene expression in a particular cell or tissue, or cell extract are provided, for example, including at a particular developmental stage or in a particular disease state. Nucleotide sequence tags derived from cDNA can provide information on the gene, allele, or isoform which is expressed, and their incidence in a sample reflects the level of expression of the gene. The methods described herein therefore enable quantitative and qualitative analysis of gene expression.

In particular, the herein-described methods are useful for isolating nucleotide sequence tags which reflect the 5' and/or 3' sequences of transcripts corresponding to expressed genes. Such nucleotide sequence tags are therefore representative of a terminal transcribed sequence of a gene. In general, they comprise a terminal transcribed sequence of a gene.

Such tags are referred to for convenience as "Terminal Tags", and the techniques for obtaining such terminal tags will be referred to, again for convenience only, as "Terminal SAGE".

As explained above, the prior art SAGE and LongSAGE techniques have disadvantages associated with the fact that the tags produced using these techniques are essentially "internal" in origin (i.e., they correspond to internal sequences of the expressed genes). This is because, in the prior art SAGE techniques, the "start" of the tag is defined by the 5' most (or 3' most) terminal Anchoring Enzyme site on the gene, while its "end" position is defined by the offset between the Tagging Enzyme recognition site and its cutting site. While either the 5' end or the 3' end of the cDNA can be anchored in the known SAGE and LongSAGE techniques, this anchoring, and the fact that the cDNA is treated with the Anchoring Enzyme prior to ligation to the adaptors or linkers, means that the tags generated by the SAGE methods of the prior art essentially correspond to "internal" sequences.

Accordingly, pre-digestion of the cDNA with Anchoring Enzyme means that the position of the tags in relation to the entire sequence is essentially determined by the position of the most terminal Anchoring Enzyme site in the transcribed sequence. The prior art SAGE methods therefore invariably result in "internal" nucleotide sequence tags.

In contrast, the Terminal SAGE techniques described in this document enable the isolation of nucleotide sequence tags which are "terminal" in origin. In other words, the tags obtained using the techniques described herein may comprise the 5' or 3' sequences of the processed nucleic acids and hence the transcribed sequences of the expressed genes. For convenience, the method for obtaining a 5' terminal transcribed sequence of a gene may be described as "5' Terminal SAGE", and the method for obtaining a 3' terminal transcribed sequence of a gene may be described as "3' Terminal SAGE".

Similarly, the nucleotide sequence tag comprising a 5' terminal transcribed sequence of a gene may conveniently be referred to as a "5' terminal tag", and the nucleotide sequence tag comprising a 3' terminal transcribed sequence of a gene may be conveniently referred to as a "3' terminal tag". However, it will be appreciated that where a nucleic acid which is not part of a gene is being processed using the methods described here, these terms may equally have more general meanings (i.e, as referring to the 5' terminal sequence or 3' terminal sequence, as the case may be, of the nucleic acid in question).

In the methods of Terminal SAGE as described here, a "first nucleic acid sequence" is first provided. This is lined with a "linker sequence" to form a "linked nucleic acid". The linker sequence comprises a "first recognition site" for a "first nucleic acid cleavage enzyme". The first recognition site is such that that allows cleavage of the first nucleic acid sequence at a site distant from the first recognition site. The linker sequence also comprises a "second recognition site" for a "second nucleic acid cleavage enzyme", that allows nucleic acid cleavage at a site distant from the second recognition site. The cleavage site for the second nucleic acid cleavage enzyme is located at a position within or about the first recognition site. The linked nucleic acid preferably has the structure: 5'—second recognition site-first recognition site-first nucleic acid-3'

The linked nucleic acid is then cleaved with the first nucleic acid cleavage enzyme. The products of this cleavage reaction include a linked tag comprising the linker sequence linked to a nucleotide sequence tag representative of the first nucleic acid sequence and comprising a terminal portion thereof; and a second nucleic acid sequence comprising a remainder portion of the first nucleic acid.

In highly preferred embodiments, the methods described here involve anchoring an entire full-length cDNA and ligating an adaptor/linker to the free end. The adaptor/linker comprises a PCR primer site, as well as two Type IIS restriction enzyme recognition sites. The first site may be referred to as the Tagging Enzyme site (here MmeI). In addition, a site which may be referred to as the "Anchor Enzyme" site (e.g., BseRI) is also provided for removal of the primer sequence following ligation and amplification of the ditags. The amplified ditags are then concatamerised, sequenced, and analysed, as described in further detail below.

It will be appreciated that where the first nucleic acid sequence comprises a cDNA, the nucleotide sequence tag which is produced from the method comprises a terminal transcribed sequence of the relevant gene. Preferably, the cDNA is first processed to remove at least a portion of the 5' untranslated region (UTR) or the 3' UTR as the case may be. Thus, for example, where a tag comprising a 3' terminal transcribed sequence is desired, the cDNA may be processed to remove at least a portion of the polyA/T tail. However, it will be appreciated that removal of the entirety of the 3' UTR such as the polyA/T tail is not strictly necessary, provided the tag is long enough to capture sequence information upstream of the polyA/T tail.

The nucleotide sequence tag which is produced may be detected to determine the identity of the first nucleic acid. Its sequence may also be determined for this. In preferred embodiments, the nucleotide sequence tag which is produced is linked "tail to tail" with another nucleotide sequence tag to produce a "ditag", which is then analysed (for details see below). The ditag may be amplified, for example, by PCR, by introducing appropriate sequences in the linker sequence. Two or more ditags may be joined together to form concatermers, and the sequence of the concatamers determined for high throughput genomic screening.

The terms "tag" and "nucleotide sequence tag" as used in this document should be taken as synonymous with each other, and to mean a short nucleotide sequence which is diagnostic of a longer one. The presence of the larger sequence may be detected by detecting the presence of the tag. Preferably, identification of the tag sequence, or at least a part of it, is sufficient to identify the longer sequence. In highly preferred embodiments, the sequence of the nucleotide sequence tag uniquely identifies a gene.

The tag sequence is typically derived from the longer sequence, and may be a fragment of it. Preferably, the length of the tag is less than 15%, preferably less than 10%, most preferably less than 5% or less of the length of the gene. The tag may be of any length, but typically, the length of the tag is between 5-40 bases, preferably between 10-30 bases, more preferably between 15-20 bases in length.

Although longer sequence tags are preferred, the methods and compositions described here may suitably be used with shorter tags, for example, tags of 5, 6, 7, 8, 9, 10, 11, 12, 13, 14 or 15 bases. However, preferably, the tags have a minimum length of 16 bases, and are preferably 17 bases, 18 bases, 19 bases, or preferably 20 bases or more.

In preferred embodiments, where the nucleotide sequence tag is of a gene, the length of the tag (i.e., the amount of sequence derived from the longer sequence) is sufficient to provide at least a preliminary indication of the identity of the gene. Preferably, the length of the tag is sufficient to provide a unique indication of the identity of a gene, i.e., it is long enough to identify the gene.

As will be apparent from the description below, the length of the tag may be varied by choice of the first nucleic acid cleavage enzyme (i.e., the first Type IIS restriction endonuclease in preferred embodiments), in particular, the "offset" by which the first nucleic acid cleavage enzyme cuts from its recognition sequence.

Preferably, the tag is diagnostic of a gene, or a transcription or translation product thereof. The gene, etc corresponding to the tag may be easily identified by hybridisation or library screening, or by database comparison. The nucleotide sequence tag may be indicate the presence of a gene in a cell (or organ, tissue or individual) or the expression of the gene. Where a gene is highly expressed gene by a cell, the number of copies of the nucleotide sequence tag corresponding to the gene would be expected to be higher than for a gene whose expression is relatively low. Therefore, the number of copies of the nucleotide sequence tag in any particular sample may be determined to establish the degree or amount of expression of a gene. The sequence of the tag may be derived from a portion of the sequence of the gene, which may be from a non-coding portion of the gene (e.g., an intron, an untranslated region such as a 5' UTR or a 3' UTR) or a coding portion (e.g., an exon), or a combination of the two (e.g., a junction). The sequence of the tag may correspond to a sequence of the coding strand of the gene or mRNA or cDNA, or its complement or opposite strand.

The nucleotide sequence tag may be derived from any part of the longer sequence. Where the longer sequence comprises a gene, the nucleotide sequence tag in preferred embodiments comprises a terminal transcribed sequence (the meaning of this term is explained below). In highly preferred embodiments, the nucleotide sequence tag is derived from a 5' terminal sequence, preferably a 5' terminal transcribed sequence. Alternatively, or in addition, the nucleotide sequence tag is derived from a 3' terminal sequence, preferably a 3' terminal transcribed sequence.

The nucleotide sequence tag may indicate the presence of an expression product of a gene, such as a messenger RNA. The presence or identity of the tag may be determined to establish whether a protein product is present in a cell, etc. Thus, where the "longer sequence" comprises a gene, the nucleotide sequence tag may be used for establishing or quantitating gene expression.

It will be appreciated that the gene which corresponds toe the nucleotide sequence tag may be one which is known to be expressed, whether in the particular cell, tissue or organism, or known to be expressed in general in other types of cells, tissues or organisms. Alternatively, it may be a completely unknown or new gene, or a new transcript corresponding to a known gene, whether previously known to be expressed in the particular cell, etc or not.

The methods described herein may therefore be used to provide sequence "signatures" corresponding to terminal portions of nucleic acids, as opposed to internal portions. Such terminal sequence information, including terminal transcribed sequence information, is useful for various purposes, as described in detail below.

The "terminal portion" relates to the sequence of a nucleic acid at or about the 5' or 3' terminus of the nucleic acid. The "terminal portion" may comprise any number of bases. It may comprise the extreme terminal base, or it may comprise sequence just within the terminus (i.e., lacking the extreme terminal base). The "terminal portion" may lack 1, 2, 3, 4 or 5 bases of the extreme terminus. However, in preferred embodiments the terminal portion includes residues at the extreme terminus of the nucleic acid. Thus, in such preferred embodiments, the "terminal portion" comprises, preferably consists of, the first N residues, or the last N residues, of the nucleic acid, where N=1, 2, 3, 4, 5, 6, 7, 8, 9, 10, 11, 12, 13, 14, 15 . . . 29, 30, 31, 32, 33, 34 or 35 or more. In preferred embodiments, terminal portions include the extreme end, i.e., the extreme terminal base, the first or last nucleotide, residue, base or base pair in the particular nucleic acid sequence.

In relation to a coding sequence such as a gene or mRNA, the terminal portion or "terminal transcribed sequence" (and the terms "5' terminal transcribed sequence" and "3' terminal transcribed sequence") should be understood to be defined in relation to the sequence of the gene as expressed in mRNA.

That is to say, the terminal transcribed sequence should preferably include sequences at the beginning or end, as the case may be, of the transcribed portion of a relevant nucleic acid sequence (i.e., a gene, an mRNA, a cDNA or a genomic sequence). A 5' terminal transcribed sequence will therefore typically comprise a portion corresponding to the 5' untranslated region (5' UTR) of a transcript. Similarly, a 3' terminal transcribed sequence will therefore typically comprise a portion corresponding to the 3' untranslated region (3' UTR) of a transcript. Preferably, however, at least a portion of the polyA/T tail is removed from the cDNA prior to it being processed, preferably the entirety of the polyA/T tail is removed from the cDNA. Where this occurs, the 3' terminal transcribed sequence will correspond to the 3' sequence of the mRNA as it is transcribed, before addition of the polyA/T tail.

A full length cDNA comprises four sections: 5' untranslated region, coding sequences (the sequences which translated into protein), 3' untranslated region and poly A tail. Poly A sequences do not exist in the genomic DNA but are added after the mRNA was processed to remove introns. So, by removing the poly A region from the cDNA and obtaining the terminal region of 3' end, it is possible using the techniques described herein to identify the exact 3' border of the transcripts and map back to the corresponding chromosomes.

It will be appreciated that the cDNA may be further manipulated before being processed in the Terminal SAGE methods described here. For example, one or more residues may be removed from the relevant terminus. This embodiment may be useful to remove untranslated sequences, so that the nucleotide sequence tag comprises fewer residues of untranslated sequence. The untranslated sequence may be removed entirely from the relevant terminus, to leave only coding sequence (so that the nucleotide sequence tags generated correspond to 5' or 3' terminal coding sequences).

Accordingly, the "terminal transcribed sequence" preferably includes at least an extreme upstream portion, or at least an extreme downstream portion, of the sequence of an mRNA, cDNA, etc, as the case may be. However, as with the terminal portions discussed above, the "terminal transcribed sequence" may comprise the extreme terminal base, or it may comprise sequence just within that base (i.e., lacking the extreme terminal base). The "terminal transcribed sequence" may lack 1, 2, 3, 4 or 5 bases of the extreme terminal base. In preferred embodiments, however, the "terminal transcribed sequence" includes the first base, or the last base, as the case may be.

In such preferred embodiments, the 5' terminal transcribed sequence includes the first 5, 6, 7, 8, 9, 10, 11, 12, 13, 14, 15, 16, 17, 18, 19, 20, 21, 22, 23, 24, 25, 26, 27, 28, 29 or 30 nucleotides or bases of the transcribed portion of the gene. The 3' terminal transcribed sequence may include such numbers of nucleotides or bases of the transcribed portion of the gene, preferably not counting the polyA/T tail. In highly preferred embodiments, the terminal transcribed sequence includes sequence corresponding to at least the first or last 16 bases, preferably at least the first or last 20 bases of the transcript.

However, as noted above, the 5' terminal transcribed sequences (for example, a 5' terminal transcribed sequence of a cDNA) may comprise a sequence corresponding to a location at or about the 5' terminus of the transcribed portion, but it preferably includes the first base in the transcript. Similarly, a 3' terminal transcribed sequence, for example of a cDNA, may comprise a sequence corresponding to a location at or about the 3' terminus of the transcribed portion, but it preferably includes the last base, i.e., the last base which was transcribed from the gene.

It is apparent from the above that using the herein-described methods it is possible to determine the identities of genes which are expressed by a particular cell type, tissue, organ or individual. This enables a gene expression profile to be compiled for the relevant cell, etc. Transcriptome analysis may also be readily carried out using the methods described herein.

The methods described herein therefore enable both 5' and 3' terminal transcribed sequences to be obtained with ease.

Furthermore, is will be apparent that the presence of a particular nucleotide sequence tag as a product of the reactions indicates an instance of expression of the corresponding gene. Therefore, the level of expression of a particular gene by a particular cell, tissue, organ or individual may be established. It is also possible to determine which genes are expressed, and which genes are not expressed, in such cells, etc. Relative levels of gene expression may be compared between genes, and between cells, etc. It will be apparent that the herein-described methods may also be used to determine differences in gene expression between different states of a cell, for example, a healthy state and a diseased state. Comparison of gene expression profiles of a cell (or tissue, etc) known to be diseased and a candidate cell may be used to diagnose particular diseases, or susceptibility to such diseases. Differences in gene expression profiles between different developmental states of a cell, between pluripotent and differentiated cells, or between cells in different parts of the cell cycle may also be determined with ease.

Knowledge of 5' and/or 3' terminal sequences of a nucleic acid such as a gene provides many advantages, which have been mentioned in passing, and will be explained in greater detail below.

Other uses of the methods and compositions described here will be apparent to the skilled reader.

The practice of the present invention will employ, unless otherwise indicated, conventional techniques of chemistry, molecular biology, microbiology, recombinant DNA or immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press (this reference is informally known as "Maniatis"); Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

In a general aspect, the methods and compositions described here enable the production of a nucleotide sequence tag, or a number of nucleotide sequence tags, from the terminus of a nucleic acid such as a transcribed gene. In particular, the herein-described methods are useful for isolating nucleotide sequence tags which reflect the 5' and/or 3' termini of the transcribed sequences of expressed genes.

The herein-described methods generally involve providing a first nucleic acid sequence of interest. The methods of the present invention are suitable for use on any nucleic acid sequence, but are most useful for DNA sequences, such as complementary deoxyribonucleic acid (cDNA) sequences. Use of cDNA sequences, typically generated for example by reverse transcription from an mRNA extracted from a cell, or derived from a library, is preferred for the gene expression aspects of the methods and compositions described here.

In such embodiments, the cDNA preferably comprises a terminal transcribed sequence of the relevant gene, that is, either a 5' terminal transcribed sequence, or a 3' terminal transcribed sequence, or both. A number of methods are known for obtaining such cDNA, and are also disclosed in detail below. Where a tag with 5' sequence is desired, "full length" cDNA with 5' terminal transcribed sequence may be provided. To obtain a tag with 3' terminal transcribed sequence, techniques may be employed to remove at least some or all of the polyT tail or optionally some non-coding sequence; alternatively, the length of the tag may be chosen so that it is long enough to span the polyA/T tail and capture at least some 3' terminal transcribed sequence of the cDNA in the tag.

The first nucleic acid is then linked to a linker sequence without any prior processing, in particular without any prior cleavage step. Accordingly, in contrast to the prior art methods, the first nucleic acid sequence (in preferred embodiments, a cDNA) is not digested by restriction endonucleases prior to linking to the linker sequence. Thus, in the herein-described Terminal SAGE methods, no pre-digestion with a 4-base cutter (i.e., NlaIII) is carried out before ligation to the adaptor. It is this difference that enables the herein-described Terminal SAGE technique to generate sequence tags corresponding to the extreme ends of the DNA, instead of internal sequence tags.

In preferred embodiments of the methods described here, therefore, the cDNA may be attached to the linker as soon as it is made, so long as the terminal transcribed portions are present in the cDNA. This enables sequence information from terminal transcribed portions of the gene or cDNA to be present in the nucleotide sequence tags which are produced by the herein-described methods.

The linker sequence is linked to the 5' terminus or the 3' terminus of the first nucleic acid, depending on whether sequence information is to be obtained from the 5' or 3' end. Thus, in preferred embodiments where it is desired to obtain 5' terminal transcribed sequence from a cDNA (i.e., in the method referred to as "5' Terminal SAGE"), the linker is linked to the 5' terminus of the cDNA. Likewise, to obtain nucleic acid sequence information from the 3' terminal transcribed sequence of a cDNA in preferred embodiments ("3' Terminal SAGE"), the linker is linked to the 3' terminus of the cDNA.

Linkage of the first nucleic acid to the linker sequence produces a construct referred to as a "linked nucleic acid".

The linkage of the first nucleic acid to the linker sequence to produce the linked nucleic acid may be by any means, but is preferably by ligation (for example, by use of ligases). The first nucleic acid may be immobilised during linkage, for example, on a microbead. Immobilisation eases the purification of products, but is not strictly necessary. Where immobilisation is carried out, the first nucleic acid is immobilised at the terminus which is not being linked. That is to say, if it is desired to obtain a nucleotide sequence tag from one end of the nucleic acid, the nucleic acid may be immobilised on a bead at the other end. For example, the 5' cap of a transcript (the cDNA) can also be utilized for labeling or binding a capture means for isolation of a nucleotide sequence tag corresponding to the 3' terminal transcribed sequence.

The first nucleic acid may be provided with a capture means for this purpose. The capture means may comprise a binding element, as known in the art, such as biotin, strepavidin, digoxigenin, etc. Any suitable binding element or capture means may be employed. The microbead may be magnetic.

The linker sequence at least comprises a first recognition site for a first nucleic acid cleavage enzyme. The first nucleic acid cleavage enzyme is such that it is capable of cleaving nucleic acid at a site remote and preferably downstream from its recognition sequence. For example, where 5' sequence information is desired from a cDNA sequence, the cleavage site of the first nucleic acid cleavage enzyme is preferably 3' of the recognition sequence, relative to the coding strand of the cDNA.

Linker sequences may be constructed using means known in the art, for example, known oligonucleotide synthesis techniques.

The location of the first recognition site for the first nucleic acid is such that the cleavage site is preferably present in the first nucleic acid sequence. For example, the cleavage site may be located in the sequence of the cDNA which is linked to the linker sequence. Such an arrangement enables the capture of some or more sequence information from the cDNA by cleavage of the nucleic acid by the first nucleic acid cleavage enzyme, as described later. Needless to say, the offset between the recognition site and the cleavage site of the first nucleic acid cleavage enzyme may be manipulated to obtain more or less sequence information, again as described below.

The first nucleic acid cleavage enzyme preferably comprises a restriction enzyme or restriction endonuclease, preferably a Type IIS restriction endonuclease. However, the use of artificial or modified enzymes is envisaged, as described in detail below. The first nucleic acid cleavage enzyme (such as a restriction endonuclease) may sometimes be referred to as a "Tagging Enzyme". The distance (i.e., the number of bases) between the recognition site of the nucleic acid cleavage enzyme and its cleavage site may be varied, but will typically be between 5 and 15 or more (for example 20, 25, 30 etc). The larger this "offset", the more sequence information is captured in the tag (as will be explained below).

In highly preferred embodiments, the first nucleic acid cleavage enzyme comprises a restriction endonuclease, preferably a Type IIS restriction endonuclease, preferably BseRI.

The linker sequence may further comprise a second recognition site for a second nucleic acid cleavage enzyme. The second nucleic acid cleavage enzyme may sometimes be referred to as an "Anchoring Enzyme". The second recognition site enables the second nucleic acid cleavage enzyme to cleave at a site distant from the second recognition site. Such an embodiment is useful where high throughput analysis by means of ditags is desired (see later). The second recognition site where present is located on the linker sequence such that the second nucleic acid cleavage enzyme cleavage site is at a position within or about the first recognition site. Preferably, the cleavage site of the second nucleic acid cleavage enzyme is located within the first recognition site.

Preferably, the second nucleic acid cleavage enzyme comprises a restriction endonuclease, preferably a Type IIS restriction endonuclease, whose recognition site is 6 bases or greater, preferably MmeI. Preferably, the second nucleic acid cleavage enzyme is one which produces overhangs (i.e., is not a "blunt cutter").

In preferred embodiments, the linked nucleic acid comprising the first nucleic acid sequence and the linker sequence has the arrangement 5'—second recognition site-first recognition site-first nucleic acid-3'. In such embodiments, therefore, the first recognition site is located between the first nucleic acid and the second recognition site.

The linked nucleic acid is then subject to cleavage by the first restriction enzyme. This produces two products. The first product comprises the linker sequence linked to a terminal portion of the first nucleic acid sequence, and may be referred to as a "linked tag". Such a terminal portion comprises the nucleotide sequence tag, and is representative of the first nucleic acid sequence. Preferably, the first nucleic acid cleavage enzyme is one which generates an overhang, preferably a 3' overhang, and preferably therefore the nucleotide sequence tag comprises a 3' overhang at its 3' end.

The second product of the cleavage of the linked nucleic acid with the first nucleic acid cleavage enzyme comprises the remainder of the first nucleic acid, lacking the terminal portion (see below for a use of this in generating further tags).

It will be apparent that detecting the nucleotide sequence tag enables the determination of the identity of the first nucleic acid sequence. Thus, in the preferred embodiment where the first nucleic acid sequence comprises a cDNA, the nucleotide sequence tag comprises a terminal transcribed portion of the cDNA, and hence is representative of the terminal transcribed sequence of the expressed gene.

The nucleotide sequence tags generated may be identified, and in addition may have their sequences determined.

Detection of the nucleotide sequence tag may be undertaken by any means, for example, by hybridisation, pull down, gel analysis, fragment length analysis, antibody binding, Single Strand Conformation Polymorphism (SSCP) analysis, mass spectrometry, MALDI, etc. Clonal analysis, as described in further detail below, may also be carried out. Quantitation of the amount of sequence tag may be done by any means known in the art, for example, hybridisation using a suitably labelled probe and quantitation of signal emitted by bound probe. Radioactive and non-radioactive methods are envisaged for this.

For example, the tags may be used to screen an appropriate library to obtain further sequence information. The tag itself may be used as a probe, or a oligonucleotide probe produced which comprises or corresponds to the tag sequence. The probe is used to screen for example a cDNA library, and a cDNA clone obtained. The cDNA may be sequenced and compared to databases to determine its identity.

The term "oligonucleotide" as used herein refers to primers or oligomer fragments comprised of two or more deoxyribonucleotides or ribonucleotides, preferably more than three. The exact size will depend on many factors, which in turn depend on the ultimate function or use of the oligonucleotide.

In preferred embodiments, however, the nucleotide sequence tag is detected or quantitated, preferably both, by determining its sequence. This may be achieved by isolating the various nucleotide sequence tags obtained by the procedure, cloning or subcloning them into suitable vectors, and sequencing the cloned tags.

As noted above, the nucleotide sequence tags resulting from a reaction may be analysed or sequenced individually.

For example, clonal sequencing may be carried out to identify the tags produced. Clonal sequencing is similar to limiting dilution techniques used in the cloning of cell lines, and involves dilution of linked tags, ditags or concatamers thereof, and placement into individual receptacles, such that each receptacle contains about one DNA molecule per receptacle. The DNA in each receptacle may then be amplified and sequenced by standard methods known in the art, including mass spectroscopy.

An oligonucleotide composition is provided having at least two defined nucleotide sequence tags, wherein at least one of the sequence tags corresponds to at least one expressed gene, and in which at least one of the nucleotide sequence tags is generated by a Terminal SAGE method as described here. The composition may comprise about 1 to 200 ditags, and preferably about 8 to 20 ditags. Such compositions are useful for the analysis of gene expression by identifying the defined nucleotide sequence tag corresponding to an expressed gene in a cell, tissue or cell extract, for example.

However, in addition to, or as an alternative to, such individual analysis, the tags may be combined or linked into multimeric structures, and the multimeric structures themselves analysed to determine the identity and/or quantity of the component tags, and hence the expressed genes in preferred embodiments.

The term "multimeric" includes anything that comprises more than one monomer. Hence, multimeric includes dimers, trimers, tetramers, etc.

A method of detecting gene expression is provided, the method comprising the steps of: (a) providing a first linked tag and a second linked tag, each independently produced by a Terminal SAGE method as described; (b) linking the first linked tag and the second linked tag such that the nucleotide sequence tag portion of one linked tag is linked to the nucleotide sequence tag of the other linked tag to form a ditag, the ditag comprising terminal sequences from first and second genes; and (c) detecting the presence or identity of the ditag, or at least one nucleotide sequence tag comprised therein, to detect gene expression.

Thus, in such preferred embodiments, the tags which result from the methods as described above are dimerised to form ditags. A "ditag" relates to a nucleic acid sequence which comprises two linked tags joined in any fashion. The ditag may comprise only sequences from the relevant genes, or it may further include one or more linker sequences, preferably at the ends.

Each ditag therefore represents two defined nucleotide sequences of at least one transcript, representative of at least one gene. Typically, a ditag represents two transcripts from two distinct genes. The presence of a defined nucleotide sequence tag within the ditag is indicative of expression of a gene having a sequence of that tag. As described below, ditags may be amplified before analysis. However, the analysis of ditags, formed prior to any amplification step, provides a means to eliminate potential distortions introduced by amplification, e.g., PCR.

The pairing of tags for the formation of ditags is a random event. The number of different tags is expected to be large, therefore, the probability of any two tags being coupled in the same ditag is small, even for abundant transcripts. Therefore, repeated ditags potentially produced by biased standard amplification and/or cloning methods are readily excluded from analysis.

The dimerisation of the tags into ditags is preferably done in a "tail to tail" fashion, with the portion of the nucleotide sequence tag furthest from the linker sequence being referred to as the "tail". That is to say, two linked tags are linked to each other via their nucleotide sequence tag portions. The "linker" portions are therefore at the termini of the ditags, with the two nucleotide sequence tags in the middle sandwiched therebetween. Accordingly, the ditag preferably has a structure 5'-linker sequence (I)-nucleotide sequence tag (I)-nucleotide sequence tag (II)-linker sequence (II)-3'.

Cleavage of the linked nucleic acid may give rise to blunt ends or overhanging ends—e.g., 5' or 3' overhangs. In the latter case, the two linked tags are conveniently linked via their overhangs (see FIG. 3 for an example of such linking by overhangs). Overhangs enable efficient linkage or ligation. Linkage via blunt ends is also possible, where the cleavage reaction produces such blunt ends. Preferential linkage at such blunt ends may be achieved by using linkers which are dephosphorylated at their 5' ends. Of course, it will be appreciated that overhanging ends may be "polished", or made blunt, if needed. This may be achieved by exposing the nucleic acid to any suitable enzyme which removes the overhangs, such as an enzyme comprising the appropriate exonuclease activity. Thus, an enzyme comprising 3'-5' exonuclease activity may be used to remove 3' overhangs, and an enzyme comprising 5'-3' exonuclease activity may be used to remove 5' overhangs. For example, the 3'-5' exonuclease activity of Klenow fragment may be used to generate blunt ends from a 3' overhang (as described in Maniatis).

However, it will be appreciated that conversion from overhangs to blunt ends results in loss of sequence information. For example, where 20 base tags are produced with 2 base overhangs, ligation or linkage of such tags will produce 38 base ditags comprising 20 bases of useful information in each tag. In contrast, removal of the overhangs will result in the loss of information (2 bases) at the 3' end of each tag.

Linkage of the two linked tags may be by any means, but is preferably through DNA or RNA ligases. Such ligases, for example, T4 RNA ligase and T4 DNA ligase, are known in the art.

The ditags once generated may be detected by hybridisation, etc, or sequenced directly. Alternatively, and preferably, a number of ditags are linked to each other to form concatamers, and the concatamers sequenced. Such an embodiment is suitable for high throughput analysis of gene expression.

The ditags may be amplified prior to their being detected, sequenced or concatermerised. Amplification of the ditags increases their number, and hence increases the sensitivity of the detection or sequencing of the tags or ditags.

Amplification may be by any means, but is preferably by means of the polymerase chain reaction (PCR). Polymerase chain reaction technologies are described in detail in Dieffenbach C W and G S Dveksler (1995, PCR Primer, a Laboratory Manual, Cold Spring Harbor Press, Plainview N.Y.) and U.S. Pat. No. 4,683,195.

The ditag can be amplified by utilizing primers which specifically hybridize to one strand of each linker. For this purpose, the linker sequence may comprise a suitable amplification primer sequence.

The term "primer" as used herein refers to an oligonucleotide, whether occurring naturally or produced synthetically, which is capable of acting as a point of initiation of synthesis when placed under conditions in which synthesis of primer extension product which is complementary to a nucleic acid strand is induced, i.e., in the presence of nucleotides and an agent for polymerization such as DNA polymerase and at a suitable temperature and pH. The primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and source of primer.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. Preferably, the primers are substantially complementary to at least part of the linker sequences.

Figure 3:
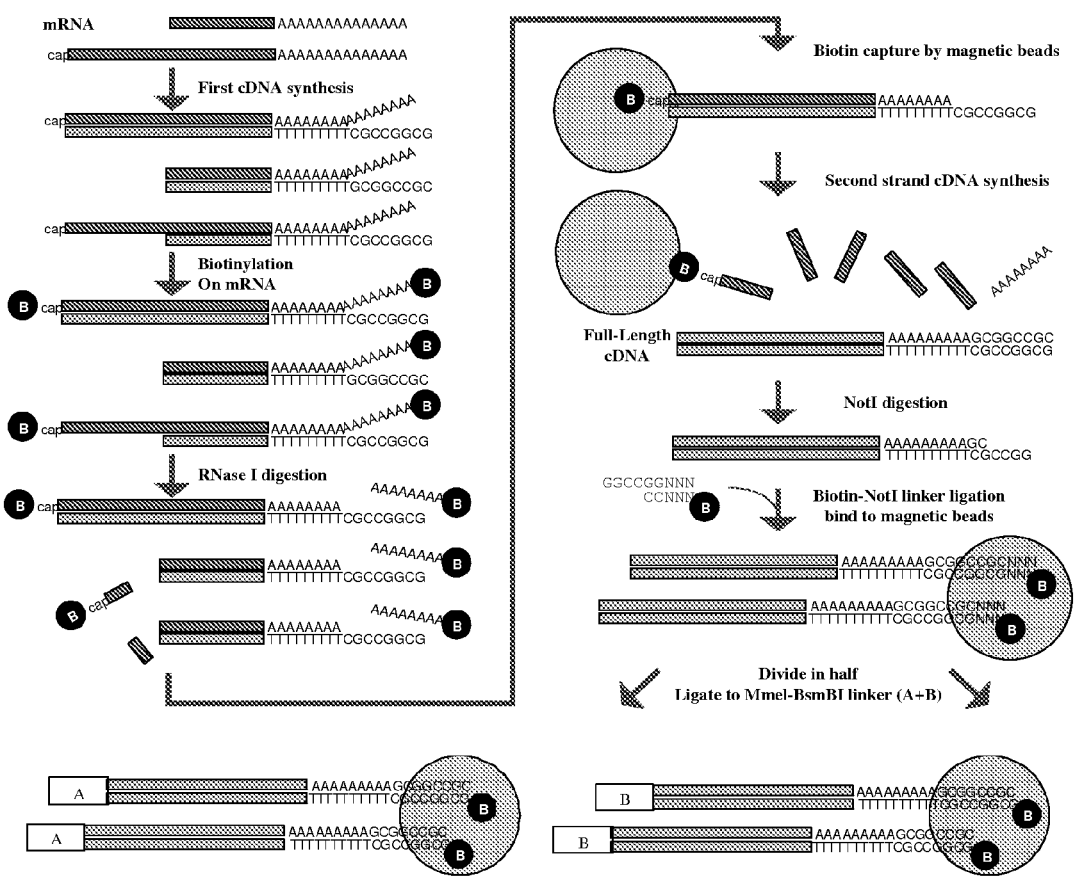
FIG. 3 is a schematic diagram showing the 5'Terminal SAGE and SAGE Walking techniques described in this document. See Detailed Description for details. Figure discloses SEQ ID NOS: 129-144 and 157-158.
Figure 3:
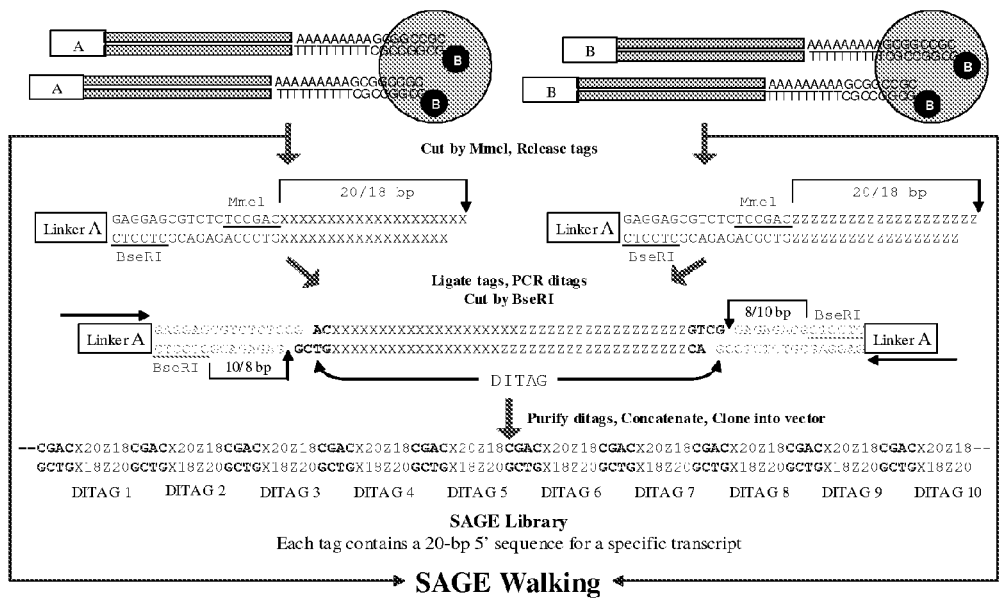
Figure 4:
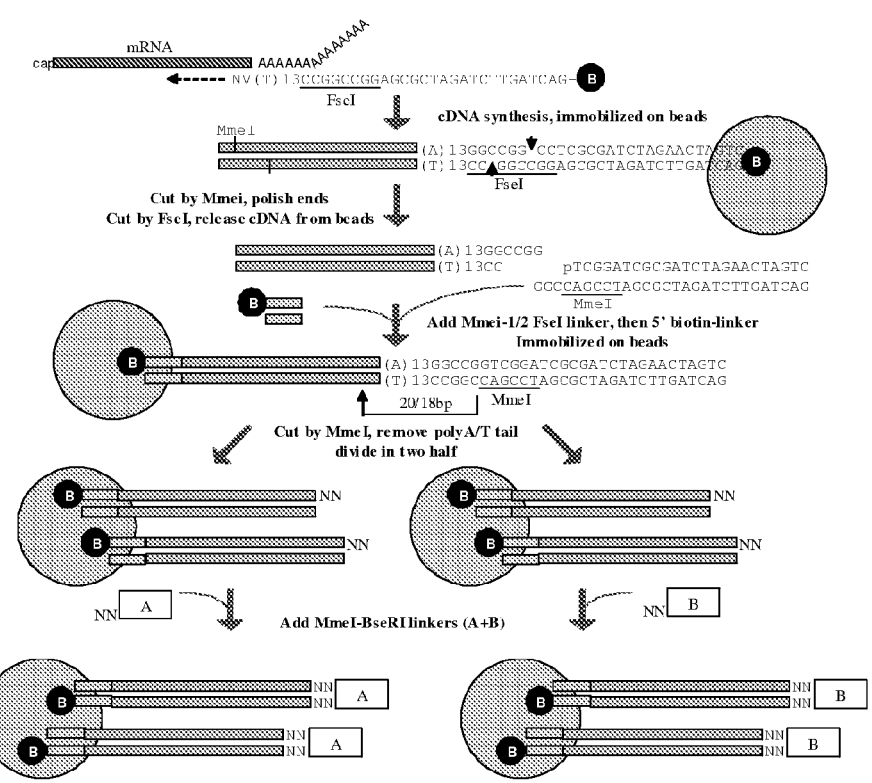
FIG. 4 is a schematic diagram showing the 3'Terminal SAGE and SAGE Walking techniques described in this document. See Detailed Description for details. Figure discloses SEQ ID NOS: 129, 145-156 and 159-161.
Figure 4:
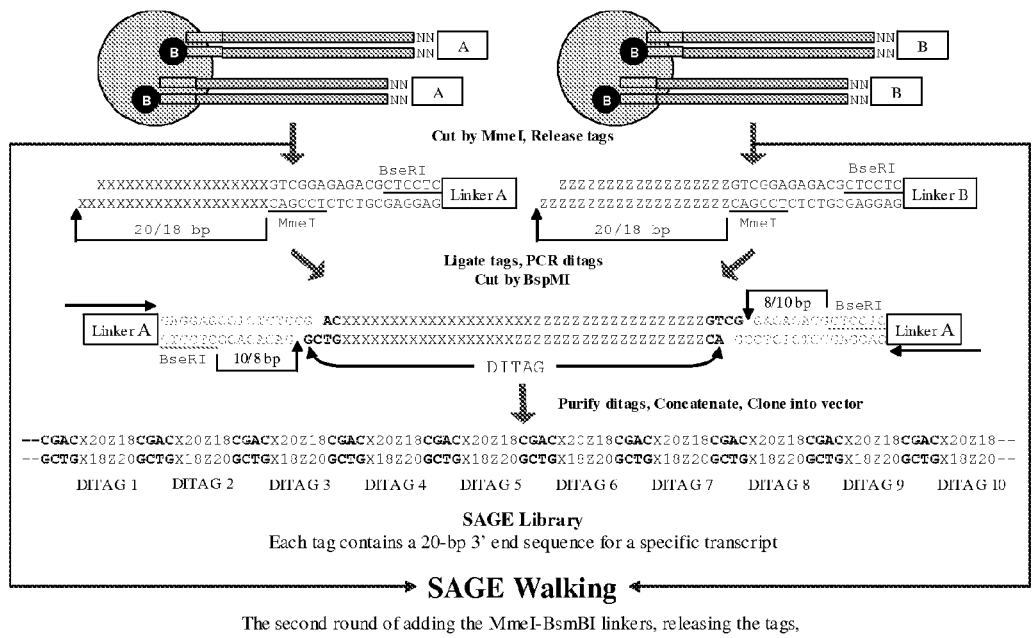

The amplification primer sequences in the two linked tags may be the same, or different. In preferred embodiments, therefore, the linked tags are generated by the methods described previously, and ligated to form ditags using DNA ligase, for example as shown in FIG. 3 or 4. Appropriate PCR primer sequences, dNTPs, polymerase, etc, and a suitable reaction buffer are then added to the ditags, and the mixture subjected to rounds of amplification as known in the art. Alternatively, the ditags can be amplified by cloning in prokaryotic-compatible vectors or by other amplification methods known to those of skill in the art.

As noted above, the ditags may be formed into higher order structures for processing and analysis. For example, concatamers or polymers of the ditags may be formed. Thus, in preferred embodiments, the identity of the nucleotide sequence tag is determined by producing and concatamerising ditags. This allows large scale nucleotide sequence tag analysis to be carried out.

In preferred embodiments, all, or most, of the ditags arising from a reaction are concatermerised. In such an embodiment, the concatamer may be sequenced to determine the sequence of the component tags and ditags, without the necessity of sequencing the tags and ditags individually. The ditags may be linked using ligase, in the same manner as for the ditags.

Appropriate "spacer" sequences may be introduced or incorporated into the concatamer to separate units of sequence which define the individual nucleotide sequence tags from which the concatamers are built up. The spacer sequences may be specifically introduced in the concatamerisation reaction, by the use of appropriate linkers or adaptors, or they may be carried over from previous reactions. In the latter case, the spacer sequences may comprise the linker sequences, or portions thereof. For example, and as illustrated in FIGS. 3 and 5, the ditags which are formed may be ligated end to end to form concatamers; in such a situation, two nucleotide sequence tags are separated by two linker sequences forming the spacer.

The concatamer may therefore have the structure 5'—linker sequence (I)-nucleotide sequence tag (1)-nucleotide sequence tag (II)-linker sequence (II)-linker sequence (III)-nucleotide sequence tag (IIII)-nucleotide sequence tag (IV)-linker sequence (IV)-etc-3' or 5'-LNNL-LNNL-LNNL-LNNL-LNNL-LNNL-LNNL-LNNL-LNNL-3', where L is a linker sequence, and N is a nucleotide sequence tag.

The presence of the "spacer" sequences enables the units comprising nucleotide sequence tags to be precisely defined. They may be ignored or stripped out during analysis of the sequence.

Alternatively, or in addition, the ditags may be treated or processed before being linked to form concatamers. Such treatment may comprise stripping or removing at least a portion of the linker sequence from the ditags. In preferred embodiments, the treatment comprises removing the bulk or the majority of the linker sequence from the ditag.

In preferred embodiments, the linker sequence comprises a second recognition site for a second nucleic acid cleavage enzyme as described above, and the linked tag or ditag is treated with the second nucleic acid cleavage enzyme, preferably BseRI. As explained above, the second recognition site is such that it directs nucleic acid cleavage by the second nucleic acid cleavage enzyme at a site remote from the recognition site. The separation between the first recognition site and the second recognition site is such that the second recognition site directs the second nucleic acid cleavage enzyme to cleave the linked tag at or about the first recognition site (see FIGS. 3 and 5 for illustrative examples).

In preferred embodiments, therefore, cleavage with the second nucleic acid cleavage enzyme removes all but 2-4 bases of the linker sequence from the ditag. Preferably, cleavage with the second nucleic acid cleavage enzyme produces a two base overhang linked to one strand of the nucleotide sequence tag. Preferably, the remnant of the linker sequence comprises a 4 base sequence comprising a 5' overhang of two bases. Thus, preferably, treatment with the second nucleic acid cleavage enzyme results in a "trimmed" ditag comprising the structure (SEQ ID NOS: 162-163):

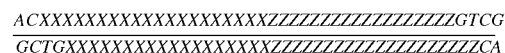

Where Xs and Zs represent sequences (the length of which may vary) from two nucleotide sequence tags.

In this preferred embodiment, the concatamer may be easily formed by joining the trimmed ditags by their CG/GC overhangs. The concatamer may be isolated and cloned into a suitable vector for handling, propagation and sequencing.

The trimmed ditag preferably comprises between 12 to 120 base pairs, preferably between 18 to 46 base pairs, preferably 40 base pairs.

The linked tags, ditags, or concatamers once generated may be detected by hybridisation, etc, or sequenced directly. They may then be sequenced.

Among the standard procedures for cloning the nucleotide sequence tags is insertion of the tags into vectors such as plasmids or phage. The linked tag, ditag or concatamers of ditags produced by the method may be cloned into recombinant vectors for further analysis, e.g., sequence analysis, plaque/plasmid hybridization using the tags as probes, by methods known to those of skill in the art.

The term "recombinant vector" refers to a plasmid, virus or other vehicle known in the art that has been manipulated by insertion or incorporation of the linked tag, ditag or concatamer genetic sequences. Such vectors contain a promoter sequence which facilitates the efficient transcription of the a marker genetic sequence for example. The vector typically contains an origin of replication, a promoter, as well as specific genes which allow phenotypic selection of the transformed cells. Vectors suitable for use include for example, pBlueScript (Stratagene, La Jolla, Calif.); pBC, pSL301 (Invitrogen) and other similar vectors known to those of skill in the art. Preferably, the linked tags, ditags or concatamers thereof are ligated into a vector for sequencing purposes.

Vectors in which the linked tags, ditags or concatamers are cloned can be transferred into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

Transformation of a host cell with a vector containing ditag(s) may be carried out by conventional techniques as are well known to those skilled in the art. Where the host is prokaryotic, such as *E. Coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed by electroporation or other commonly used methods in the art.

The linked tags, ditags etc present in a particular clone can be sequenced by standard methods (see for example, Current Protocols in Molecular Biology, supra, Unit 7) either manually or using automated methods.

One of the differences between the 5' and 3' Terminal SAGE methods described here, as compared to the prior art methods, is that the tags are extracted from the terminal 5' ends and 3' ends. In contrast, the prior art methods extract tags which are internal to the sequence; these tags are those that flank anchoring sites such as NlaIII or DpnII.

Accordingly, the methods described here are particularly useful for genome analysis. Such genome analysis is advantageously undertaken through database comparisons. The generation of 5' terminal tags using the methods described here enable the generation of sequence information which represents the starting of genes or transcripts. Likewise, generation of 3' terminal tags provide sequence information representing the end point of genes or transcripts. Such terminal tags may be compared against databases of known genes, expressed sequence tags, genomic databases, etc, to identify the nature of the gene which is expressed. With this direct mapping, expression frequency of known genes located on genome sequences can be measured by the number of appearances of the corresponding 5' and 3' tags. Thus, the higher the number of tags corresponding to a particular gene is present, the higher its level of expression in the particular sample.

Hence, in a preferred embodiment, database comparison is carried out by: making the 5' and 3' tags pairs that most likely represent the staring points and end points of genes or transcripts and mapping the tag pairs directly to genome sequences. In addition, alternative transcription start sites and polyadenalytion sites can be identified and quantified. Furthermore, previously uncharacterised genes on chromosomal sequences can be readily identified and quantified by this direct mapping of tag pairs.

The sequences of the tags, ditags, and/or concatamers obtained may be compared with suitable sequence databases, such as GenBank, to determine their identity and/or relationships. Furthermore, it will be appreciated that comparison may be made to databases such as chromosomal DNA sequence databases and cDNA databases.

A method of identifying a first mRNA molecule or a first cDNA molecule reverse transcribed from the first mRNA molecule with a known sequence in a database is provided, which may comprise the step of: matching a first nucleotide sequence which is located at a defined position at the 5' or 3' terminus of a transcribed sequence within the first mRNA or first cDNA molecule to a second nucleotide sequence in a database consisting of mRNA and/or cDNA sequences which occur at the defined position in their respective mRNA or cDNA molecules, whereby the first nucleotide sequence is identified with the known sequence in the database.

A method of identifying a first mRNA molecule or a first cDNA molecule reverse transcribed from the first mRNA molecule with a known sequence in a database is also provided, which may comprise the step of: matching a first nucleotide sequence which is located at a defined position in a first mRNA or first cDNA molecule, wherein the defined position is at the 5' or 3 terminus of a transcribed sequence in the first mRNA or first cDNA molecule, to a second nucleotide sequence in a database; determining that the second nucleotide sequence in the database is located at the defined position in its respective mRNA or cDNA molecule, whereby the first nucleotide sequence is identified with the known sequence in the database.

A method of identifying a cDNA molecule which is not represented in a database is further provided, which may comprise the steps of: comparing a first nucleotide sequence which has a predefined position at the 5' or 3' terminus of a transcribed sequence within a messenger RNA, or a cDNA molecule reverse transcribed from the messenger RNA to a database of nucleotide sequences; if no nucleotide sequences are found in the database which both match the first nucleotide sequence and occur at the defined position in an mRNA or cDNA, then hybridizing an oligonucleotide comprising the first nucleotide sequence to a cDNA clone in a library; and determining that the first nucleotide sequence is located at the defined position in the cDNA clone, whereby the cDNA molecule is identified which was not present in the database.

It will be appreciated that it is not necessary to merely compare a single nucleotide sequence against the database, and that it is possible (and perhaps more efficient) to compare pairs of nucleotide sequences against the database. Such pairs preferably comprise a nucleotide sequence corresponding to the 5' terminus of a transcribed sequence (i.e., a "5' terminal tag"), and a nucleotide sequence corresponding to the 3' terminus of a transcribed sequence (i.e., a "3' terminal tag"). In preferred embodiments, the pair comprises a 5' terminal tag and a 3' terminal tag of the same transcribed sequence (e.g., the same gene). Where there is uncertainty, the pair comprises terminal tags which are most likely to represent the ends of the relevant sequence. Thus, the pair in such preferred embodiments contains the information from the starting point and the ending point of a gene, transcript, etc. The pair therefore is sufficient to represent a unit of transcription, a full-length mRNA, or a gene.

Comparison of such pairs against the database may confirm the presence of a known corresponding gene or cDNA having the corresponding termini within the database, indicating that that known sequence within the database is expressed "in real life" in the sample (i.e., tissue, cell, etc) in question. However, it may be the case that a match is not found in the database; this would indicate that a sequence having the relevant termini was not previously known to have existed or be expressed. Such sequences may represent new genes, or previously unknown transcripts of known genes (having for example different transcription starting sites or different polyadenalytion sites, or both).

Identification of such unknown genes or novel transcripts will aid in genomic mapping and annotation. It will be appreciated that database comparisons using the nucleotide sequence tags generated by the herein-described methods, particularly in pairs as described above, will (in cases of new genes or new transcripts) immediately provide boundary sequences of the particular new genes or transcripts, as their 5' termini and 3' termini will be known. Full-length cDNA sequences of the newly identified genes can be cloned by using conventional means. Full-length sequences of the new transcripts may similarly be isolated. It will be appreciated that primers designed from the tag sequences would enable the cloning of the full length sequence from PCR of a genomic or cDNA library or RT-PCR from mRNA.

A method to verify computationally predicted genes based on genome sequences is also provided, which may comprise the steps of: mapping the pair of 5' and 3' terminal tag sequences directly to the genome sequences; identifying the tag sequences that are mapped to the predicted regions. The match of the tag sequences to the predicted gene sequences will provide evidence of the existence of the genes.

In general, the nucleotide sequence tags, linked tags, ditags and concatamers may be compared against sequence databases in the same manner as described in the prior art SAGE and LongSAGE techniques. Reference is therefore made to descriptions of these techniques, in particular, U.S. Pat. Nos. 695,937, 5,866,330 and 6,383,743 as well sa WO 02/10438, hereby incorporated by reference. The following paragraphs in this section are adapted from U.S. Pat. No. 6,383,743.

It is envisioned that the identification of differentially expressed genes using the Terminal SAGE method as described here can be used in combination with other genomics techniques. For example, individual nucleotide sequence tags or linked tags, and preferably ditags, can be hybridized with oligonucleotides immobilized on a solid support (e.g., nitrocellulose filter, glass slide, silicon chip). Such techniques include "parallel sequence analysis" as described below.

Briefly, parallel sequence analysis is performed after ditag preparation, wherein the oligonucleotide sequences to which the ditags are hybridized are preferably unlabeled and the ditag is preferably detectably labeled. Alternatively, the oligonucleotide can be labeled rather than the ditag. The ditags can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the ditag, or will be able to ascertain such, using routine experimentation. For example, PCR can be performed with labeled (e.g., fluorescein tagged) primers. Preferably, the ditag contains a fluorescent end label.

The labeled or unlabeled ditags are separated into single-stranded molecules which are preferably serially diluted and added to a solid support (e.g., a silicon chip as described by Fodor, et al., Science, 251:767, 1991) containing oligonucleotides representing, for example, every possible permutation of a 10-mer (e.g., in each grid of a chip). The solid support is then used to determine differential expression of the tags contained within that support (e.g., on a grid on a chip) by hybridization of the oligonucleotides on the solid support with tags produced from cells under different conditions (e.g., different stage of development, growth of cells in the absence and presence of a growth factor, normal versus transformed cells, comparison of different tissue expression, etc). In the case of fluoresceinated end labeled ditags, analysis of fluorescence is indicative of hybridization to a particular 10-mer. When the immobilized oligonucleotide is fluoresceinated for example, a loss of fluorescence due to quenching (by the proximity of the hybridized ditag to the labeled oligo) is observed and is analyzed for the pattern of gene expression.

The concept of deriving a defined tag from a sequence is useful in matching tags of samples to a sequence database. In the preferred embodiment, a computer method may be used to match a sample sequence with known sequences.

In one embodiment, a sequence tag for a sample is compared to corresponding information in a sequence database to identify known sequences that match the sample sequence. One or more tags can be determined for each sequence in the sequence database as the N base pairs adjacent to each anchoring enzyme site within the sequence. However, in the preferred embodiment, only the first anchoring enzyme site from the 3' end is used to determine a tag. In the preferred embodiment, the adjacent base pairs defining a tag are on the 3' side of the anchoring enzyme site, and N is preferably 9.

A linear search through such a database may be used. However, in the preferred embodiment, a sequence tag from a sample is converted to a unique numeric representation by converting each base pair (A, C, G, or T) of an N-base tag to a number or "tag code" (e.g., A=0, C=1, G=2, T=3, or any other suitable mapping). A tag is determined for each sequence of a sequence database as described above, and the tag is converted to a tag code in a similar manner. In the preferred embodiment, a set of tag codes for a sequence database is stored in a pointer file. The tag code for a sample sequence is compared to the tag codes in the pointer file to determine the location in the sequence database of the sequence corresponding to the sample tag code. (Multiple corresponding sequences may exist if the sequence database has redundancies).

FIG. 6 of U.S. Pat. No. 6,383,743 is a block diagram of a tag code database access system. A sequence database 10 (e.g., the Human Genome Sequence Database) is processed as described above, such that each sequence has a tag code determined and stored in a pointer file 12. A sample tag code X for a sample is determined as described above, and stored within a memory location 14 of a computer. The sample tag code X is compared to the pointer file 12 for a matching sequence tag code. If a match is found, a pointer associated with the matching sequence tag code is used to access the corresponding sequence in the sequence database 10.

The pointer file 12 may be in any of several formats. In one format, each entry of the pointer file 12 comprises a tag code and a pointer to a corresponding record in the sequence database 12. The sample tag code X can be compared to sequence tag codes in a linear search. Alternatively, the sequence tag codes can be sorted and a binary search used. As another alternative, the sequence tag codes can be structured in a hierarchical tree structure (e.g., a B-tree), or as a singly or doubly linked list, or in any other conveniently searchable data structure or format.

In the preferred embodiment, each entry of the pointer file 12 comprises only a pointer to a corresponding record in the sequence database 10. In building the pointer file 12, each sequence tag code is assigned to an entry position in the pointer file 12 corresponding to the value of the tag code. For example, if a sequence tag code was "1043", a pointer to the corresponding record in the sequence database 10 would be stored in entry #1043 of the pointer file 12. The value of a sample tag code X can be used to directly address the location in the pointer file 12 that corresponds to the sample tag code X, and thus rapidly access the pointer stored in that location in order to address the sequence database 10.

Because only four values are needed to represent all possible base pairs, using binary coded decimal (BCD) numbers for tag codes in conjunction with the preferred pointer file 12 structure leads to a "sparse" pointer file 12 that wastes memory or storage space. Accordingly, preferably each tag code is transformed to number base 4 (i.e., 2 bits per code digit), in known fashion, resulting in a compact pointer file 12 structure. For example, for tag sequence "AGCT", with $A=00_2$, $C=01_2$, $G=10_2$, $T=11_2$, the base four representation in binary would be "00011011".

In contrast, the BCD representation would be "00000000 00000001 00000010 000000011". Of course, it should be understood that other mappings of base pairs to codes would provide equivalent function.

The concept of deriving a defined tag from a sample sequence is also useful in comparing different samples for similarity. In the preferred embodiment, a computer method is used to match sequence tags from different samples. For example, in comparing materials having a large number of sequences (e.g., tissue), the frequency of occurrence of the various tags in a first sample can be mapped out as tag codes stored in a distribution or histogram-type data structure. For example, a table structured similar to pointer file 12 in FIG. 4 of U.S. Pat. No. 6,383,743 may be used where each entry comprises a frequency of occurrence valve. Thereafter, the various tags in a second sample can be generated, converted to tag codes, and compared to the table by directly addressing table entries with the tag code. A count can be kept of the number of matches found, as well as the location of the matches, for output in text or graphic form on an output device, and/or for storage in a data storage system for later use.

The tag comparison aspects may be implemented in hardware or software, or a combination of both. Preferably, these aspects are implemented in computer programs executing on a programmable computer comprising a processor, a data storage system (including volatile and non-volatile memory and/or storage elements), at least one input device, and at least one output device. Data input through one or more input devices for temporary or permanent storage in the data storage system includes sequences, and may include previously generated tags and tag codes for known and/or unknown sequences. Program code is applied to the input data to perform the functions described above and generate output information. The output information is applied to one or more output devices, in known fashion.

Each such computer program is preferably stored on a storage media or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

As in the prior art SAGE techniques, the method described above enables the production of a single nucleotide sequence tag for each first nucleic acid. That is to say, in preferred embodiments, only a single "signature" is obtained from each cDNA. However, it is possible to provide a plurality of nucleotide sequence tags using further steps.

Accordingly, a method of generating a plurality of nucleic acid sequences is provided, wherein each nucleic acid sequence may comprise a nucleic acid sequence tag from a nucleic acid. The further nucleotide sequence tags may be derived from sequences internal to the nucleotide sequence tag produced initially. The method may be repeated as many times as desired, to produce as many different nucleotide sequence tags as needed from a particular nucleic acid sequence.

The method of generating multiple nucleotide sequence tags makes use of the second product of the cleavage of the linked nucleic acid with the first nucleic acid cleavage enzyme, i.e., a "second nucleic acid". It will be recalled that the second nucleic acid is derived from the first nucleic acid by cleavage to remove an initial nucleotide sequence tag. The second nucleic acid therefore may comprise a sequence of the first nucleic acid 3' of the first nucleotide sequence tag.

In order to obtain a further nucleotide sequence tag from the nucleic acid, a linker sequence may be attached to the second nucleic acid, and the resulting structure subjected to cleavage by the first nucleic acid cleavage enzyme to release a further nucleotide sequence tag. The linker sequence may comprise the same or similar structure as described previously. In short, the process of providing a further tag merely feeds the second nucleic acid produced by cleavage into the first step of the process already described. It will be appreciated that each round of this process produces an additional nucleotide sequence tag, and that as many rounds of this process may be carried out as necessary, to produce as many nucleotide sequence tags as necessary. Each further iteration of the method produces a further internal sequence tag, going deeper and deeper into the nucleic acid.

Accordingly, a method of generating a plurality of nucleic acid sequences is provided, which may comprise the Terminal SAGE method as described in this document, with one or more rounds of further steps (a) to (c) as set out in Claim 1.

An embodiment of technique of SAGE Walking is described below, without limitation, with reference to FIG. 5.

The Terminal SAGE technique has been described generally in the description above. The 5' Terminal SAGE technique described in general and in detail in this section enables the production of nucleotide sequence tags corresponding to the 5' terminal sequence of a relevant nucleic acid. In preferred embodiments, the method enables the production of a nucleotide sequence tag comprising sequence corresponding to a 5' terminal transcribed sequence of a gene, mRNA or cDNA.

A method of providing an indication of an instance of expression of a gene is therefore provided, the method which may comprise the steps of: (a) providing a complementary deoxyribonucleic acid (cDNA) having a terminus preferably comprising a 5' terminal transcribed sequence of a gene; (b) linking the cDNA to an linker sequence thereby forming a linked nucleic acid, in which the linker sequence comprises a first recognition site for a first nucleic acid cleavage enzyme, preferably a restriction endonuclease, that allows nucleic acid cleavage at a site distant from the first recognition site; and (c) cleaving the linked nucleic acid with the first nucleic acid cleavage enzyme to provide a linked tag, in which the linked tag comprises a nucleotide sequence tag representative of a 5' terminal transcribed sequence of the gene; and (d) detecting the presence or identity of the linked tag or the nucleotide sequence tag to provide an indication of an instance of gene expression.

Preferably, the cDNA is linked to an linker sequence at its 5' end relative to the coding strand, i.e., 5'—linker sequence-cDNA-3', to form the linked nucleic acid. Preferably, the first recognition site for the first nucleic acid cleavage enzyme, preferably a first restriction endonuclease, allows nucleic acid cleavage at a site 3' of the first recognition site, relative to the coding strand. Preferably, the nucleic acid cleavage site cleaves within the sequence of the cDNA.

To provide a first nucleic acid sequence which is a cDNA in preferred embodiments for 5' Terminal SAGE, it is necessary to provide cDNA with 5' terminal transcribed portions. In general, any method which is capable of producing "full length" cDNA is suitable for this purpose. Size fractionation may be used to filter out smaller non-full length species.

For example, full length cDNA may be synthesised by the oligo-capping method described in Maruyama and Sugano, Gene 138, 171-174, 1994, Suzuki et al., Gene 200, 149-156, 1997 using appropriate oligo-dT primers. The oligo capping method replaces the cap structure of a mRNA with an oligoribonucleotide (r-oligo) to label the 5' end of eukaryotic mRNAs. The cap is removed with tobacco acid pyrophosphatase (TAP) and r-oligos ligated to decapped mRNAs with T4 RNA ligase. This reaction is made cap-specific by removing 5'-phosphates of non-capped RNAs with alkaline phosphatase prior to TAP treatment. Unlike the conventional methods that label the 5' end of cDNAs, this method specifically labels the capped end of the mRNAs with a synthetic r-oligo prior to first-strand cDNA synthesis. The 5' end of the mRNA is identified quite simply by reverse transcription-polymerase chain reaction (RT-PCR).

Although the oligo-capping method is preferred, a number of other methods of making or enriching full length cDNA with 5' sequences are known in the art, and any of these may be employed for the purposes described here.

A number of libraries of full length cDNA are known in the art, and these may be used as well in the methods and compositions described here. Full length cDNA libraries from various organisms and tissue types may be obtained commercially from a number of manufacturers, such as ResGen (Invitrogen). Furthermore, a database of full length sequences may be found for example, at the Institute of Medical Science, University of Tokyo.

In the following detailed description, which should not be taken as limiting, reference is made to FIG. 3. Reference is also made to the detailed protocols set out in Examples 1 and 2.

To add the MmeI linkers to the starting point of transcripts, the cDNA fragments are 5' intact. To do so, the established cap-trapper method may be employed for full-length cDNA selection to ensure most of the substance cDNA fragments have the intact 5' end. The cap-trapper method is described in detail in Genomics 37 327-336., Biotechniques 32 (5): 984-985 and Biotechniques 30 (6): 1250-1254.

Other techniques to enable full length cDNA to be obtained are also suitable. For example, full length cDNA may be obtained by using eIF-4E cap-binding protein to identify and bind to the 5' mRNA cap (Mol. Cell. Biol. 15: 3363-3371). Furthermore, methods based on RNA terminal tagging with RNA ligase may also be used (Methods Enzymol. 65: 65-74).

As full-length cDNA is made, a NotI-dT15VN primer is used to initiate the cDNA synthesis so introduce a NotI site at the end of the polyA/T tail. After full-length cDNA are selected, the 3' end will be digested by NotI followed by a ligation of the biotin-NotI linker, so the 3'end biotinylated cDNA are able immobilized on streptavidin coated magnetic beads. Since NotI is an 8-bp cuter, the possibility of internal cDNA digestion is rare.

The immobilized cDNA population is then divided in half for the addition of MmeI-BseRI linker A and MmeI-BseRI linker B. These linkers contain the same sequence for MmeI and BseRI sites, but have different sequences for PCR priming sites. Here MmeI is a IIS type enzyme that cut DNA 20-bp down stream from its recognition site (TCCGACN20/18; SEQ ID NO: 164). MmeI is used for releasing tags, called the "Tag Enzyme" (TE). BseRI is another IIS type enzyme that cut DNA 10-bp apart from its recognition site (GAG-GAGN10/8; SEQ ID NO: 165). BseRI will be used for removing the PCR arms and leave a minimal anchor sequences with the tags, called the "Anchor Enzyme" (AE).

MmeI digestion releases linked tags comprising a unique sequence signature corresponding to the 5' portion of the transcribed gene.

After MmeI digestion, the released tags from the two populations may be combined and ligated. Every two tags are joined together face to face (tail to tail) with two base pairs overlapping to form a ditag flanked with linkers at both ends. The ditags are subsequently purified and amplified by PCR with biotinylated primer A and B. Ditags with different linkers will be more efficiently amplified in PCR reaction than the one with same linker sequences.

The next technical trick is how to remove the long arms from the amplified ditags, keep the anchor sequence minimal, and make the tags with cohesive ends and ligatable to each other. A BseRI site is placed next to the MmeI site apart by 6 base pairs in the linker sequences. That will allow BseRI cut into the MmeI site (GAGGAGNNNNNNTC▲CG▼AC; SEQ ID NO: 1) and create a CG-3' overhang. The probability of having a BseRI site within the 20-bp tag sequences of all transcripts is very rare (P=0.00488). After purification, the trimmed ditags are ligated to each other resulting concatenated ditags separated each other with an anchor sequence CGAC. Because each 20-bp tag has two base pairs overlapping in a ditag unit and a 4-bp anchor sequence per ditag in concatenated clones that means information of every 21 bp sequence in the concatenated clones contains one tag representing one transcript molecule. To tag one million transcript molecules, only 21000 concatenated clones (≈1000 bp) need to be generated for sequencing at both ends of the clones (42000 seq. reads) assuming an average 500 bp quality sequences per read.

The 3' Terminal SAGE technique described in general and in detail in this section enables the production of nucleotide sequence tags corresponding to the 5' terminal sequence of a relevant nucleic acid. In preferred embodiments, the method enables the production of a nucleotide sequence tag comprising sequence corresponding to a 3' transcribed sequence of a gene, mRNA or cDNA.

A method of providing an indication of an instance of expression of a gene is provided, the method which may comprise the steps of: (a) providing a complementary deoxyribonucleic acid (cDNA) having a terminus comprising a 3' terminal transcribed sequence of a gene; (b) linking the cDNA to an linker sequence thereby forming a linked nucleic acid, in which the linker sequence comprises a first recognition site for a first nucleic acid cleavage enzyme, preferably a restriction endonuclease, that allows nucleic acid cleavage at a site distant from the first recognition site; and (c) cleaving the linked nucleic acid with the first nucleic acid cleavage enzyme to provide a linked tag, in which the linked tag comprises a nucleotide sequence tag representative of a 3' terminal transcribed sequence of the gene; and (d) detecting the presence or identity of the linked tag or the nucleotide sequence tag to provide an indication of an instance of gene expression.

To provide a first nucleic acid sequence which is a cDNA in preferred embodiments for 3' Terminal SAGE, it is necessary to provide cDNA comprising a terminus with 3' terminal transcribed portions. Preferably, at least some of the polyA/T tail at the 3' terminus of the cDNA can be removed. However, it will be appreciated that it is not strictly necessary to remove the whole of the poly A/T tail from the cDNA, provided that at least some sequence from the transcribed portion is captured in the nucleotide sequence tag. Any polyT sequence which may be in the nucleotide sequence tag may be ignored for analysis. Provided the nucleotide sequence tag is long enough, it will capture some transcribed sequence from the cDNA sufficient to identify the relevant gene.

Where it is desired to remove at least some of the polyA/T portion, any method which is capable of producing a cDNA without (or substantially without) a poly dT tail may suitably be employed for this purpose. Such techniques are discussed in detail in Shibata et al (2001), Removal of polyA tails from full-length cDNA libraries for high efficiency sequencing, Biotechniques, 31(5), 1042-1049, 2001. As noted above, it is not necessary for the entirety of the polyA/T tail to be removed, so long as the nucleotide sequence tag is long enough to contain useful sequence information. Thus, for example, the Shibata technique may produce cDNA with an average polyA tail length of 4 or fewer, but this does not matter provided the nucleotide sequence tag is long enough to capture 3' transcribed sequence of the gene.

In a particularly preferred embodiment, however, all of the polyA/T tail removed from the cDNA. Thus, in such embodiments, a cDNA having a terminus comprising a 3' terminal transcribed sequence of a gene may in particular be provided by the following steps: (i) deriving a cDNA from an mRNA by reverse transcription with an primer comprising a sequence 5'-NV(T)$^{13}$CCGGCCGG-3' (SEQ ID NO: 4), in which N=A, C, G or T and V=A, C or G; (ii) producing a double stranded cDNA therefrom and digesting the double stranded cDNA with FseI to produce a cleaved cDNA comprising

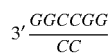

overhang; (iii) linking the cleaved cDNA to a linker comprising

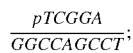

and (iv) cleaving the resulting molecule with MmeI to produce a cDNA lacking a polyA/T tail.

In the following detailed description of 3' Terminal SAGE, reference is made to FIG. 4. This detailed description should not be taken as limiting. Reference is also made to the detailed protocols set out in Examples 3 and 4.

To add the MmeI linkers to the 3'end of cDNA fragments, the polyA/T tails must be first removed precisely at their starting point. To do so, the biotin-FseI-dT13VN primer is used to initiate cDNA synthesis. The two anchor nucleotides (V=A, C, G; and N=A, C, G, T) will guide the primer to anneal at the first 13 As in the polyA tail of mRNA. Thus all cDNA fragments will have a 13-bp polyA/T tail followed by an FseI site and a biotin at the end. Double strand cDNA will be first immobilized on magnetic beads, and then digested by MmeI enzyme to clean up any possible internal MmeI sites in cDNA. After polishing the ends, cDNA fragments are released from the beads by FseI digestion and create a cohesive 3'end. FseI is an 8-bp cuter like NotI, so the internal FseI sites in cDNA are rare. A 1/2FseI-MmeI linker is first ligated to the cohesive 3' end, and then a biotin linker is added to the 5'end of cDNA. After adding the biotin-linker, the cDNA fragments are once again immobilized on magnetic beads, but this time are by the 5'ends, and with an external MmeI site located 18 base pairs (6 residuals from the FseI site after digestion and ligation and a 13-polyA/T tail) apart from the 3' extremity. A MmeI digestion will precisely remove the polyA/T tail and create a two base pair overhang 3'end.

The polyA/T-less cDNA is then divided by half into two populations, one half is to add the MmeI-BseRI linker A, and the other half is to add the MmeI-BseRI linker B. At this point, an external MmeI site is precisely introduced at the 3' termini of transcripts. All steps in the rest of the procedure including releasing SAGE tags, ligating ditags, amplifying, and concatenating are all exactly the same as in the 5' Terminal SAGE procedure.

The techniques described here generally utilise nucleic acid cleaving or nicking enzymes, such as DNA cleavage enzymes, which recognise and cleave specific nucleic acid sequences. Such enzymes are preferably restriction enzymes (restriction endonucleases). As used in this document, the terms "restriction endonucleases" and "restriction enzymes" refer to bacterial enzymes which bind to a specific double-stranded DNA sequence termed a recognition site or recognition nucleotide sequence, and cut double-stranded DNA at or near the specific recognition site.

Preferably, the nucleic acid cleavage enzymes cleave the nucleic acid at a position outside of the recognition sequence. The cleavage position is therefore "offset" from the recognition position, and the enzymes may for convenience be referred to as "offset cleavage enzymes". In particular, use of "Type IIS restriction enzymes" (described in further detail below) are preferred.

As described elsewhere, a linker comprising a recognition sequence for such an offset cleavage enzyme is joined to a cDNA molecule as a first step in providing a tag.

Although the use of Type IIS restriction enzymes is preferred in the methods and compositions described here, it will be appreciated that derivitised or modified or engineered versions of such enzymes may equally be used, provided they have the properties of sequence recognition and nucleic acid cleavage (or nicking) at sites distant from the cognate recognition sequences. Thus, the methods and compositions described here employ enzymes which cleave nucleic acids at offset positions. All that is required for the 5' and 3' Terminal SAGE techniques is that the linker comprise a recognition site for an enzyme that allows nucleic cleavage at a site in the nucleic acid distant from the recognition site for the enzyme. Engineering methods, for example those described in Kim Y G, Shi Y, Berg J M, Chandrasegaran S. (1997) Gene Dec. 5, 1997; 203(1):43-9, Smith J, Berg J M, Chandrasegaran S. (1999) Nucleic Acids Res Jan. 15, 1999; 27(2):674-81 and Kim Y G, Smith J, Durgesha M, Chandrasegaran S. (1998) Biol Chem 1998 April-May; 379(4-5):489-95, may be used to enhance the cleavage efficiency, modify the recognition sequence, or to increase, decrease, or otherwise modify the offset between the recognition site and the cleavage site. Zinc finger binding domains may be used for engineering chimeric restriction enzymes, as described in Kim, Y.-G., Cha, J. and Chandrasegaran, S. (1996) *Proc. Natl. Acad. Sci. USA,* 93, 1156-1160, Huang, B., Schaeffer, C. J., Li, Q. and Tsai, M.-D. (1996) *J. Prot. Chem.,* 15, 481-489 and Kim, Y.-G., Shi, Y., Berg, J. M. and Chandrasegaran, S. (1997) *Gene,* 203, 43-49.

In particular, the use of chimeric enzymes comprising sequence recognition domains and nucleic acid cleavage domains is envisioned. The recognition domains and the nucleic acid cleavage domains may be linked and separated by a linker of variable length, to allow cleavage to occur remotely from the recognition sequence.

The recognition domains are capable of recognising and binding to specific nucleic acid sequences, and may comprise, for example, zinc finger domains designed according to the rules established in WO 98/53057, WO 98/53060, WO 98/53058, WO 98/53059. Methods of engineering, as well as rational and rule based design of zinc fingers, are also generally known in the art. The nucleic acid cleavage domains are capable of nicking or cleaving single or double stranded nucleic acids, and may be derived from known or existing cleavage domains found, for example, in restriction nucleases, DNAses or RNAses. The recognition domain and the cleavage domain in the chimeric enzyme may be separated by a linker to allow cleavage remote from the recognition site. Such linkers may comprise structured or flexible linkers as known in the art, and described for example in WO 00/44568, which is hereby incorporated by reference. The length of the linkers may be modified according to the offset desired, i.e., a longer linker will be predicated where a longer tag is required.

Indeed, it may be possible to employ completely artificial enzymes not derived from restriction enzymes which have this property. Such derivitised, modified or engineered restriction enzymes, as well as artificial enzymes, having these properties, should be understood to be encompassed for use in the methods and compositions described here.

Specifically, the methods and compositions described here employ restriction enzymes which do not cleave within their recognition sites, but instead cleave at sequences of defined distance from their recognition sequence. Such restriction enzymes are typically referred to as "Type IIS" restriction enzymes.

Type IIS restriction endonucleases cleave at a defined distance up to 20 bp away from their asymmetric recognition sites (Szybalski, W., Gene, 40:169, 1985). Examples of type IIS restriction endonucleases include BsmFI and FokI. Other similar enzymes will be known to those of skill in the art (see, Current Protocols in Molecular Biology, supra).

Type IIS restrictions suitable for use in the methods and compositions described here are shown in Table 2 below. Sequence representations in the table use the standard abbreviations (*Eur. J. Biochem.* 150: 1-5, 1985) to represent ambiguity. Recognition sequences are written from 5' to 3', only one strand being given. If the point of cleavage has been determined, the precise site is marked with ^. The character _ is sometimes used to mark the cut site on the complementary strand. Accordingly, it can be seen that the choice of the specific Type IIS restriction endonuclease will determine the offset, and hence the length of the specific sequence tag generated by the methods and compositions described here. It will be apparent that that the longer the offset and hence the tag, the more specific the sequence tag generated will be.

In preferred embodiments, the restriction endonuclease used is MmeI, which has a recognition sequence of TCCRACNNNNNNNNNNNNNNNNNN_NN^ (SEQ ID NO: 5), and cuts at a position 20/18 bases from its recognition sequence, resulting a 3' protruding overhang of 2 nucleotides (2 nt). Accordingly, use of a linker comprising a TCCRAC sequence is envisioned, more preferably a TCCGAC sequence. Cleavage of such a linker joined at its 3' end to a nucleic acid sequence, for example a full length cDNA, will produce a tag comprising 20 bases on one strand, and 18 bases on the other. The strand comprising 20 bases may be referred to as the "top" strand, while the strand comprising 18 bases may be referred to as the "bottom" strand.

Type IIS enzymes are of special interest in molecular biology. These enzymes recognize asymmetric base sequences and cleave DNA at a specified position up to 20 base pairs outside of the recognition site. Blunting the ends of their digestion products, followed by ligation, does not destroy their recognition sites. This property is useful in several applications, including the generation of deletions of increasing length (Hasan, N., et al., A novel multistep method for generating precise unidirectional deletions using BspMI, a class-IIS restriction enzyme, Gene, 50, 55-62, 1986) and mapping the sequence specificity of DNA modification (Posfai, G. and Szybalski, W., A simple method for locating methylated bases in DNA, as applied to detect asymmetric methylation by M. FokIA, Gene, 69, 147-151, 1988) and PCR product cloning. Due to the asymmetric nature of their recognition sequences, type IIS R-M systems comprise two methylases, one for each strand, sometimes each methylating a different base (Bitinaite, J., et al., Alw26I, Eco31I and Esp3I-type IIS methyltransferases modifying cytosine and adenine in complementary strands of the target DNA, Nucleic Acids Res., 20, 4981-4985, 1992).

Exemplary Type IIS restriction enzymes are described in the restriction enzyme database REBASE (Roberts R J, Macelis D. (2001) REBASE—restriction enzymes and methylases. Nucleic Acids Res. Jan. 1, 2001; 29(1):268-9 and Roberts, R. J. and Macelis, D. (1999) *Nucleic Acids Res.,* 27, 312-313), which may be accessed at rebase.neb.com.

REBASE is a comprehensive database of information about restriction enzymes and related proteins. It contains published and unpublished references, recognition and cleavage sites, isoschizomers, commercial availability, methylation sensitivity, crystal and sequence data. DNA methyltransferases, homing endonucleases, nicking enzymes, specificity subunits and control proteins are also included. Most recently, putative DNA methyltransferases and restriction enzymes, as predicted from analysis of genomic sequences, are also listed. The data is distributed via Email, ftp (ftp.neb.com), and the Web (http://rebase.neb.com).

TABLE 2

Type II restriction enzymes cleaving outside their recognition sequences (Type IIS restriction enzymes).

| Enzymes | Recognition Sequence | Isoschizomers | SEQ ID NO |
|---|---|---|---|
| AarI | CACCTGCNNNN^NNNN_ | — | 6 |
| AceIII | CAGCTCNNNNNNN^NNNN_— | — | 7 |
| AloI | _NNNNN^NNNNNNNGAACNNNNNNTCC NNNNNNN_NNNNN^ | — | 8 |

TABLE 2-continued

Type II restriction enzymes cleaving outside
their recognition sequences
(Type IIS restriction enzymes).

| Enzymes | Recognition Sequence | Isoschizomers | SEQ ID NO |
|---|---|---|---|
| BaeI | _NNNNN^NNNNNNNNNNACNNNNGTAY CNNNNNNN_NNNNN^ | — | 9 |
| Bbr7I | GAAGACNNNNNNNN^NNNN_ | — | 10 |
| BbvI | GCAGCNNNNNNNN^NNNN_ | AlwXI BseKI BseXI Bsp423I Bst12I Bst71I BstV1I | 11 |
| BbvII | GAAGACNN^NNNN_ | BbsI Bbv16II BpiI BpuAI Bsc91I BspBS31I BspIS4I BspTS514I BstBS32I BstTS5I BstV2I | 12 |
| BccI | CCATCNNNN^N_ | — | 13 |
| Bce83I | CTTGAGNNNNNNNNNNNNNNNN_NN^ | BpuEI | 14 |
| BceAI | ACGGCNNNNNNNNNNNN^NN_ | — | 15 |
| BcefI | ACGGCNNNNNNNNNNNN^N_ | — | 16 |
| BcgI | _NN^ANNNNNNNNNNCGANNNNNNTGCN NNNNNNNNN_NN^ | — | 17 |
| BciVI | GTATCCNNNNN_N^ | BfuI | 18 |
| BfiI | ACTGGGNNNN_N^ | BmrI | 19 |
| BinI | GGATCNNNN^N_ | Ac1WI AlwI BspPI BstH9I Bst31TI EacI | 20 |
| BplI | _NNNNN^NNNNNNNNGAGNNNNCTCN NNNNNNN_NNN^ | — | 21 |
| BsaXI | _NNN^NNNNNNNNNACNNNNNCTCCNN NNNNN_NNN^ | — | 22 |
| BscAI | GCATCNNNNN^NN_ | Bst19I | 23 |
| BseMII | CTCAGNNNNNNNN_NN^ | — | 24 |
| BseRI | GAGGAGNNNNNNNN_NN^ | — | 25 |
| BsgI | GTGCAGNNNNNNNNNNNNNNNN_NN^ | — | 26 |
| BsmI | GAATG_CN^ | Asp26HI Asp27HI Asp35HI Asp36HI Asp40HI Asp50HI BsaMI BscCI Mva1269I PctI | |
| BsmAI | GTCTCN^NNNN_ | Alw26I BsoMAI | 27 |
| BsmFI | GGGACNNNNNNNNNN^NNNN_ | BspLU11III BstOZ616I | 28 |
| Bsp24I | _NNNNN^NNNNNNNNGACNNNNNNNTGG NNNNNNN_NNNNN^ | — | 29 |
| BspCNI | CTCAGNNNNNNNN_NN^ | — | 30 |

TABLE 2-continued

Type II restriction enzymes cleaving outside
their recognition sequences
(Type IIS restriction enzymes).

| Enzymes | Recognition Sequence | Isoschizomers | SEQ ID NO |
|---|---|---|---|
| BspMI | ACCTGCNNNN^NNNN_ | Acc36I BfuAI BveI | 31 |
| BsrI | ACTG_GN^ | Bse1I BseM BsrSI Bst11I Tsp1I | |
| BsrDI | GCAATG_NN^ | Bse3DI BseMI | |
| BstF5I | GGATG_NN^ | BseGI | |
| BtsI | GCAGTG_NN^ | — | |
| CjeI | _NNNNNN^NNNNNNNNCCANNNNNNNGT NNNNNNNNN_NNNNNN^ | — | 32 |
| CjePI | _NNNNNN^NNNNNNNCCANNNNNNNTC NNNNNNNN_NNNNNN^ | — | 33 |
| EciI | GGCGGANNNNNNNNNN_NN^ | — | 34 |
| Eco31I | GGTCTCN^NNNN_ | Bli736I BsaI Bso31I BspTNI EcoA4I EcoO44I | 35 |
| Eco57I | CTGAAGNNNNNNNNNNNNNNNN_NN^ | AcuI BspKT5I | 36 |
| Eco57MI | CTGRAGNNNNNNNNNNNNNNNN_NN^ | — | 37 |
| Esp3I | CGTCTCN^NNNN_ | BsmBI BstGZ53I | 38 |
| FalI | _NNNNN^NNNNNNNNNAAGNNNNNCTTN NNNNNNN_NNNNN^ | — | 39 |
| FauI | CCCGCNNNN^NN_ | Bme585I BstFZ438I SmuI | 40 |
| FokI | GGATGNNNNNNNNN^NNNN | BstPZ418I | 41 |
| GsuI | CTGGAGNNNNNNNNNNNNNNNN_NN^ | BpmI | 42 |
| HaeIV | _NNNNNN^NNNNNNNGAYNNNNNRTCN NNNNNNNN_NNNNN^ | — | 43 |
| HgaI | GACGCNNNNN^NNNNN_ | — | 44 |
| Hin4I | _NNNNN^NNNNNNNNGAYNNNNNVTCN NNNNNNNN_NNNNN^ | — | 45 |
| HphI | GGTGANNNNNNN_N^ | AsuHPI | 46 |
| HpyAV | CCTTCNNNNN_N^ | — | 47 |
| Ksp632I | CTCTTCN^NNN_ | Bco5I Bco116I BcoKI BseZI Bst6I Bsu6I Eam1104I EarI | 48 |
| MboII | GAAGANNNNNNN_N^ | NcuI | 49 |
| MlyI | GAGTCNNNNN^ | SchI | 50 |
| MmeI | TCCRACNNNNNNNNNNNNNNNNNNNN_NN^ | — | 51 |
| MnlI | CCTCNNNNNN_N^ | — | 52 |
| PleI | GAGTCNNNN^N_ | PpsI | 53 |
| PpiI | _NNNNN^NNNNNNNGAACNNNNNCTCN NNNNNNN_NNNNN^ | — | 54 |

TABLE 2-continued

Type II restriction enzymes cleaving outside
their recognition sequences
(Type IIS restriction enzymes).

| Enzymes | Recognition Sequence | Isoschizomers | SEQ ID NO |
|---|---|---|---|
| PsrI | _NNNNN^NNNNNNNGAACNNNNNNNTAC NNNNNNN_NNNNN^ | – | 55 |
| RleAI | CCCACANNNNNNNNN_NNN^ | – | 56 |
| SapI | GCTCTTCN^NNN_ | VpaK32I | 57 |
| SfaNI | GCATCNNNNN^NNNN_ | BspST5I LweI PhaI | 58 |
| SspD5I | GGTGANNNNNNNN^ | – | 59 |
| Sth132I | CCCGNNNN^NNNN_ | – | 60 |
| StsI | GGATGNNNNNNNNNN^NNNN_ | – | 61 |
| TaqII | GACCGANNNNNNNNN_NN^, CACCCANNNNNNNNN_NN^ | – | 62 63 |
| TspDTI | ATGAANNNNNNNNN_NN^ | – | 64 |
| TspGWI | ACGGANNNNNNNNN_NN^ | – | 65 |
| TspRI | _NNCASTGNN^ | – | |
| Tth111II | CAARCANNNNNNNNN_NN^ | – | 66 |

The invention is described further, for the purpose of illustration only, in the following examples.

The methods described herein have specific advantages over prior art techniques as they enable the generation of terminal transcribed sequences from cDNAs. Knowledge of such terminal transcribed sequences enables the discrimination between genes which are similar over their internal regions. In addition, the 5' and 3' terminal transcribed sequences may be used as "launch pads" for the identification of upstream or downstream (as the case may be) non-coding, untranscribed, untranslated or control regions. For example, the promoters or other control regions (such as enhancers) of a particular gene may be obtained easily once its 5' terminal transcribed sequence is known, by means of "walking" techniques, or by searching sequence databases.

Promoters may be identified by a number of methods. For example, it is known that eukaryotic gene promoters are usually locates upstream of the transcription starting site and possess a consensus sequence such as CAAT box or TATA box. The 5' Terminal SAGE method described here essentially identifies the 5' transcription start site; sequences upstream of the transcription start site may be obtained by chromosomal walking, or preferably by examining a genomic database using standard bioinformatics tools to search for promoter consensus regions based on the presence of consensus sequences. The identity of putative promoters may be confirmed by making constructs with suitable reporters and examining expression of reporter, by means well known in the art.

Furthermore, once the 5' and the 3' terminal transcribed sequences are determined, it is a simple matter to obtain a full length clone (a cDNA clone or a genomic clone) from an mRNA or cDNA or genomic library. Appropriate primers corresponding to these sequences may be synthesised and used as PCR primers in a polymerase chain reaction to amplify the full length clone.

Specific uses of the terminal tags produced according to the methods and compositions described here are described. In particular, specific uses of the methods described herein for transcriptome characterisation, genome annotation, novel gene discoveries, and promoter identification are described.

It will be apparent that the terminal transcribed sequences derived from cDNAs may be used for many other purposes, and that the skilled person will be aware of such uses. Accordingly, the following uses should not be taken to be limiting.

Due to the current limitations, the original SAGE technique has not been applied broadly and deeply comparing to other competing technologies such as microarrays. Many SAGE experiments done in the prior art are simply not deep enough to be statistically significant, particularly to rare transcripts. The Terminal SAGE techniques, on the other hand, may be used to collect a large number of tag pairs of 5' and 3' Terminal SAGE for various genomes such as human and zebrafish.

The 5' and 3' Terminal SAGE methods may be used in conjunction with large scale sequencing efforts, for example, zebrafish full-length cDNA cloning and sequencing from a mixed adult fish library and an embryonic library, to obtain a comprehensive picture of zebrafish transcriptomes at embryonic and adult stages. The combination of these two approaches has the potential to provide a comprehensive disclosure of zebrafish transcriptomes and large number of full-length transcript clones and sequences.

The experimental data will be invaluable for thorough annotation of the upcoming zebrafish genome sequences.

Using the Terminal SAGE techniques, and obtaining one million 5' and 3'tag-pairs from zebrafish, it will only be necessary to process fewer than 40,000 Terminal SAGE clones (i.e., clones of concatamers) with fewer than 70,000 sequence reads on the assumption that each SAGE concatamer clone is about 2 kp; each clone will be sequenced from both ends; and each sequence read will provide 800 bp in average.

This approach may be readily applied to other organisms, such as mouse, humans, etc.

More importantly, the new Terminal SAGE methods may be applied to stem cell research projects.

A deep and comprehensive characterization of stem cell transcriptomes has never been done, though some limited attempts have been reported using the original SAGE techniques. However, the data for novel genes involved in stem cell constitution is not convincing.

Use of the Terminal SAGE methods as described here to collect large number of tags will allow for the first time a complete characterization of stem cell transcriptomes, and will make huge contribution to human genome annotation. Comparisons may be made between embryonic stem cells (ES cells) and a committed type of stem cell for deep 5' and 3' sequence analyses.

It is believed possible to obtain a near complete list of genes expressed and their activities in stem cells by generating one million tag-pairs of 5' and 3' Terminal SAGE for each of the ES cell and the other cell. Compared to microarray analysis, this new approach will have a much better chance to convincingly identify key genes that are differentially expressed at low levels between these cells.

Any new transcript identified by this method may be easily isolated in full-length by RT-PCR using the 5' and 3' tag information.

Applying the 5' Terminal SAGE techniques to cells such as zebrafish and human stem cell will allow the identification of the vast majority of genes at their transcript initiation sites.

The experimental data will enable the identification and extraction of promoter sequences for all of the 5' Terminal SAGE identified genes, and establish a large promoter database for human and zebrafish. These large set of expression-based promoter databases will provide a solid knowledge base for mining promoter functions, training computational programs for promoter predictions, and extending the understanding of comprehensive gene regulatory networking mechanisms.

The invention will now be further described by way of the following non-limiting examples.

EXAMPLES

Example 1

5' Terminal SAGE Operational Protocol 1.1 Full Length cDNA Synthesis

NotI-oligo dT primers (14 µg) and 20 µg of polyA+ RNA are ethanol precipitated and resuspended into 10 µl of ddH$_2$O. Heat up at 65° C. for 10 min and left at 42° C. for 1 min.

In a separate tube, mix the following components: 5× first strand synthesis buffer 30 µl, 0.1M DTT 11 µl, 10 mM dNTP 9 µl, saturated trehalose 15 µl, 4.9M sorbitol 50 µl and Superscript II reverse transcriptase 15 µl. Mix with RNA from above and incubate at 40° C. for 4 min, 50° C. for 2 min and 56° C. for 60 min. 2 µl of proteinase K (20 mg/ml) is added and the reaction is incubated at 45° C. for 15 min followed by phenol/chloroform extraction and ethanol precipitation.

The RNA/cDNA heter-duplex is resuspended into 44.5 µl of ddH$_2$O. 3 µl of 1.1 M NaOAc pH 4.5 and 2.5 µl of 100 mM NaIO$_4$ are added to oxidize the diol structures of the mRNA. The 50 µl reaction is incubated on ice in the dark for 45 min followed by adding 0.5 µl of 10% SDS, 11 µl of 5 M NaCl and 61 µl of isopropanol.

The precipitated RNA/DNA is biotinylated in 50 µl of ddH$_2$O by added the 5 µL 1M NaOAc (pH6.1), 5 µL 10% (w/v) SDS and 150 µL 10 mM long-arm biotin hydrazide. Leave at RT/dark/O/N. Add: 5 µL 5M NaCl, 75 µL 1M RNase-free NaOAc (pH6.1), 750 µL 100% EtOH or 200 µL of 100% Isopropanol. −80° C./30'+*. Centrifuge at 14 krpm/ 4° C./30'. Wash pellet w/70% (v/v) EtOH/30%, DEPC-treated ddH$_2$O, centrifuge at 14 krpm/4° C./10'. Remove XS liquid, air-dry pellet. Resuspend pellet in 70 µL DEPC-ddH$_2$O, then add: 10 µL 10× RNaseI buffer, 25 U RNaseI/ug of starting mRNA. 37° C./30'. Add 2.5 µL of 40 mg/mL Yeast tRNA and ½ volume of 5M NaCl to stop the reaction.

While the biotinylated RNA-DNA heteroduplex is ppting, prepare the Streptavidin-labelled Dynabeads:

Pipet 500 µL of M-280 Streptavidin beads into an RNase-free Eppendorf tube. Place on magnet, wait at least 30", and remove sup. Resuspend beads in 500 µL 1.times. binding buffer (2M NaCl, 50 mM EDTA, pH 8.0). Place on magnet, wait at least 30", and remove sup. Repeat the 1.times. binding buffer wash for 3 times. Resuspend beads in 500 µL 1.times. binding buffer w/100 µg of Yeast tRNA. 30'+/4.degree. C./mix occasionally. Place on magnet, wait at least 30", and remove sup. Wash with 1.times. binding buffer for 3 times. Resuspend in 100 µL 1.times. binding buffer. Mix beads and DNA-RNA heteroduplex (V.sub.t=200 µL), binding at 2 M NaCl. 30'/RT/rotating. Place on magnet, wait at least 30", and remove sup. Wash 2.times. w/400 µL of 1.times. binding buffer. Place on magnet, wait at least 30", and remove sup. Wash w/400 µL of 0.4% (w/v) SDS plus 50 µg/mL Yeast tRNA. Place on magnet, wait at least 30", and remove sup. Wash w/400 µL of 1.times. wash buffer (10 mM Tris-HCl pH7.5, 0.2 mM EDTA, 10 mM NaCl & 20% (v/v) Glycerol, 40 µg/mL Yeast tRNA). Place on magnet, wait at least 30", and remove sup. Wash w/400 µL of 50 µg/mL Yeast tRNA. Place on magnet, wait at least 30", and remove sup.

Release the first strand cDNA by alkali hydrolysis of RNA. Add: 50 µL 50 mM NaOH and 5 mM EDTA (pH8.0) 10'/RT/ rotating. Transfer the sup. to another tube containing 50 µL 1M Tris-Cl (pH7.5). Repeat the lysis procedure for 2 more times. The final volume is 300 µL.

1.2 Single Strand Linker A & B Ligation

Precipitate the single strand first cDNA with glycogen and divide the cDNA into 2 tubes, A and B. Add the following reagents to the each corresponding tube on ice.

| Contents | Tube A | Tube B |
| --- | --- | --- |
| cDNA | 5 µL | 5 µL |
| Linker A (N5) | 1.6 µg | — |
| Linker A (N6) | 0.4 µg | — |
| Linker B (N5) | 1.6 µg | |
| Linker B (N6) | — | 0.4 µg |
| Soln II (Takara kit) | 10 µl | 10 µl |
| Soln I (Takara ligation kit) | 20 µl | 20 µl |
| Total volume | 40 µl | |

16° C./o/n. and then 70° C. 10' to inactivate the ligase. Increase the volume to 200 µl and phenol/chloroform extraction. Sephacryl-300 to remove the excess linkers and precipitate the cDNA with EtOH and glycogen.

Resuspend the pellet with 60 µl of ddH$_2$O, add 8 µl 10× Extaq buffer, 8 µl 2.5 mM dNTP 4 µl ExTaq enzymes. 65° C. 5'→68° C. 30'→72° C. 10'.

Precipitate the cDNA with EtOH and glycogen. Resuspended with ddH$_2$O.

1.3 Binding cDNA to Magnetic Beads

The double strand cDNAs are digested with NotI at 37° C. for 1 hour in a volume of 50 µl. The enzyme is then inactivated with proteinase K and extracted with phenol/chloroform and then ethanol precipitated.

The samples are mixed with 200 ng of NotI linker adaptor. Ligation is carried out in total volume of 10 μl at 16° C. for overnight followed by 70° C. for 10' to inactivate enzyme. The excess adaptor is removed by Sephacryl-300.

Dynabeads M280 streptavidin beads are used to bind the Biotinylated cDNA fragments according to the manufacturer's recommendation.

1.4 Digesting the cDNA with Tagging Enzyme MmeI

Place the two tubes (A and B) on magnetic stand, remove the supernatant (wash buffer from Dynabeads).

Add the following reagents to each tube.

| | |
|---|---|
| ddH$_2$0 | 86 μl |
| MmeI | 2 μl |
| 10X buffer | 10 μl |
| (1:10) SAM | 2 μl |
| Total volume | 100 μl. |

Incubate at 37° C. for 1 hour with mixing.

Remove the supernatant which contains the tags. Phenol/chloroform and precipitate.

Optionally, a Klenow fill-in reaction may be carried out to produce blunt ends. If carried out, the pellet is resuspended and the following carried out.

Add the following components to each tube containing 10 μl of sample from the above.

| | |
|---|---|
| 10X Klenow buffer | 5 μl |
| 100XBSA | 1 μl |
| dNTP (10 mM each) | 2.5 μl |
| ddH$_2$0 | 30.5 μl |
| Klenow polymerase | 1 μl |
| Total volume | 50 μl |

Mix well and incubate for 30' at 37° C.

Pool the ditags and phenol/chloroform followed by EtOH precipitation.

The Klenow fill in step is optional, and may result in less sequence information being obtained (see elsewhere in this document for a detailed discussion).

Example 2

Ligating Tags to Create Ditags

Resuspend the precipitated pellet from the above in 1.5 μl and add 1.5 μl of the following reagents to form the ditags.

| | |
|---|---|
| 3 mM Tris-HCl, pH 7.5 | 1.25 μl |
| 10X Ligation buffer | 0.75 μl |
| ddH$_2$0 | 0.75 μl |
| T4 ligase | 1 μl |

Incubate at 16° C. for overnight.

2.1 PCR Amplifying and Gel Purifying the 138 bp Ditags

Set up 200 to 300 reactions as following (in 96 PCR plates).

| | |
|---|---|
| 10XBV buffer | 5 μl |
| DMSO | 3 μl |
| dNTPmix | 7.5 μl |

-continued

| | |
|---|---|
| PCR primer A (175 ng/μl) | 2 μl |
| PCR primer B (175 ng/μl) | 2 μl |
| ddH$_2$0 | 29 μl |
| Platinum Taq enzyme | 0.5 μl |
| Template (1:230 dilution) | 1 μl |
| Total volume | 50 μl |

Cycling condition: 95° C. 2' 1 cycle. 95° C. 30", 55° C. 1', 70° C. 1'. 27 cycles. 70° C. 5'.

Run a diagnostic 4% agarose gel to analyze the PCR product and purify the 138 bp ditags by 12% polyacrylamide gel electrophoresis.

2.2 Digesting the Ditags with Anchoring Enzyme BseRI and Purifying the 46 Bp Ditag Digest the 138 bp ditags with BseRI to yield 46 bp ditag.

| | |
|---|---|
| 138 bp ditags | 42 μl |
| 10X NEB buffer II | 15 μl |
| BseRI | 12 μl |
| ddH$_2$0 | 81 μl |
| Total volume | 150 μl |

And incubate at 37° C. for 2 to 3 hours. Phenol/chloroform and EtOH precipitate. Run a diagnostic 4% agarose gel to check the efficiency of the digestion and purify the 46 bp ditags by 12% polyacrylamide gel electrophoresis.

2.3 Ligating the 46 bp Ditag to Form Concatamers

Set up the ligation reaction using the gel purified ditag in a total volume of 10 μl and incubate 16 C for 2 to 3 hours. Gel purify the concatamers from 8% polyacrylamide, select the DNA size range around 2 kbp.

2.4 Cloning Concatamers into Vector

In a separate reaction, digest the plasmid vector with HhaI and ligate the purified concatamers into the linearized vector following standard molecular biology protocol. Transform the ligation into high efficiency competent cells.

The concatamers of 5' Terminal SAGE tags may then be sequenced using conventional means.

Example 3

3' Terminal SAGE Operational Protocol 3.1 cDNA Synthesis

GsuI-dT16 primers (1 μg) and 5 μg of polyA$^+$ RNA are mixed in final volume of 7 μl. Heat up at 70° C. for 10 min and leave on ice.

Synthesize the cDNA according to the manufacturer's recommendation (Invitrogen superscript cDNA synthesis system) but using the Biotinylated SalI adaptor. The excess adaptor is removed by Sephacryl-300.

3.2 Binding cDNA to Magnetic Beads

Dynabeads M280 streptavidin beads are used to bind the Biotinylated cDNA fragments according to the manufacturer's recommendation.

3.3 Digesting the cDNA with GsuI to Remove PolyA Tail

The double strand cDNA on beads are digested with GsuI at 30° C. for 1 hour. After the digestion is completed, inactivating the enzyme by washing the tube twice with buffer containing 1% SDS. Four more wash with wash buffer (5 mM Tris-HCl pH 7.5, 0.5 mM EDTA. 1 mM NaCl and 200 μg/μl BSA). The last wash use 1× ligation buffer.

3.4 Ligating MmeI-BseRI Adaptors to cDNA

Place the tube on magnetic stand to remove the supernatant (the ligation buffer). Add the following reagents to the beads on ice.

|  | Tube A | Tube B |
|---|---|---|
| cDNA beads | beads | beads |
| MmeI-BseRI adaptor A (20 ng/μl) | 1.5 μl | — |
| MmeI-BseRI adaptor B (20 ng/μl) | −1.5 μl |  |
| TE | 14 μl | 14 μl |
| 10X ligation buffer | 2 μl | 2 μl |

Heat the tubes for 2' at 50° C. and cool to room temp. for 15' and chill the samples on ice. Add 2.5 μl T4 DNA ligase and mix. Incubate at 16° C. for 2 hours. Mix occasionally. Wash the tubes with wash buffer to remove the excess adaptors.

3.5 Cleaving with Tagging Enzyme MmeI

Place the two tubes (A and B) on magnetic stand, remove the supernatant (wash buffer). Add the following reagents to each tube.

| ddH₂0 | 86 μl |
|---|---|
| MmeI | 2 μl |
| 10X buffer | 10 μl |
| (1:10) SAM | 2 μl |
| Total volume | 100 μl. |

Incubate at 37° C. for 1 hour with mixing. Remove the supernatant which contains the tags. Phenol/chloroform and precipitate.

Optionally, a Klenow fill-in reaction may be carried out to produce blunt ends. If carried out, the pellet is resuspended and the following carried out.

Add the following components to each tube containing 10 μl of sample from the above section.

| 10X Klenow buffer | 5 μl |
|---|---|
| 100XBSA | 1 μl |
| dNTP (10 mM each) | 2.5 μl |
| ddH₂0 | 30.5 μl |
| Klenow polymerase | 1 μl |
| Total volume | 50 μl |

Mix well and incubate for 30' at 37° C. Pool the ditags and phenol/chloroform followed by EtOH precipitation.

The Klenow fill in step is optional, and may result in less sequence information being obtained (see elsewhere in this document for a detailed discussion).

Example 4

Ligating Tags to Create Ditags

Resuspend the pellet from the above in 1.5 μl water and add 1.5 μl of the following reagents to form the ditags.

| 3 mM Tris-HCl, pH 7.5 | 1.25 μl |
|---|---|
| 10X Ligation buffer | 0.75 μl |

-continued

| ddH₂0 | 0.75 μl |
|---|---|
| T4 ligase | 1 μl |

Incubate at 16° C. for overnight.

4.1 PCR Amplifying and Gel Purifying the 138 Bp Ditags

Set up 200 to 300 reactions as following (in 96 PCR plates).

| 10XBV buffer | 5 μl |
|---|---|
| DMSO | 3 μl |
| DNTPmix | 7.5 μl |
| PCR primer A (175 ng/μl) | 2 μl |
| PCR primer B (175 ng/μl) | 2 μl |
| ddH₂0 | 29 μl |
| Platinum Taq enzyme | 0.5 μl |
| Template (1:230 dilution) | 1 μl |
| Total volume | 50 μl |

Cycling condition: 95° C. 2' 1 cycle. 95° C. 30", 55° C. 1', 70° C. 1'. 27 cycles. 70° C. 5'.

Run a diagnostic 4% agarose gel to analyze the PCR product and purify the 138 bp ditags by 12% polyacrylamide gel electrophoresis.

4.2 Digesting the Ditags with Anchoring Enzyme BseRIi and Purifying the 46 Bp Ditag Digest the 138 bp ditags with BseRI to yield 46 bp ditag.

| 138 bp ditags | 42 μl |
|---|---|
| 10X NEB buffer II | 15 μl |
| BseRI | 12 μl |
| Total volume | 150 μl |

And incubate at 37° C. for 2 to 3 hours. Phenol/chloroform and EtoH precipitate. Run a diagnostic 4% agarose gel to check the efficiency of the digestion and purify the 46 bp ditags by 12% polyacrylamide gel electrophoresis.

4.3 Ligating the 46 Bp Ditag to Form Concatamers

Set up the ligation reaction using the gel purified ditag in a total volume of 10 μl and incubate 16 C for 2 to 3 hours. Gel purify the concatamers from 8% polyacrylamide, select the DNA size range from 1 to 1.5 kbp, or.

4.4 Cloning Concatamers Into Vector

In a separate reaction, digest the plasmid vector with HhaI and ligate the purified concatamers into the linearized vector following standard molecular biology protocol. Transform the ligation into high efficiency competent cells.

Example 5

SAGE Walking Operational Protocol

Even 20-bp tags may still seem to be not long enough to be specific for mapping on chromosomes. Sequence variations in tags caused by sequencing errors or point mutations can make the mapping to genome sequence ambiguous. Longer tags can certainly add more confidence to include certain level of mismatches. However, the longest cleavage distance of IIS enzyme is 20-bp by MmeI. To overcome this constraint, one can actually walk along the transcript sequence by reintroducing the MmeI site to the same cDNA that already released the first tag, and perform another round of SAGE tag extraction, amplification, and concatenation. The second SAGE will have 2-bp overlap with the first tags on the same transcripts. These tiled two tags of one transcript add up total 38-bp tag information that will be sufficient to tolerate variations due to SNP on either transcript sequence or on the chromosome sequence in genome sequence database, or simply sequence errors. Third or further rounds of SAGE walk may be added if necessary.

5' SAGE Walk Operational Protocol

Follow the 5' terminal tag protocol to step: Digesting the cDNA with tagging enzyme MmeI. After the digestion is completed, inactivate the enzyme by washing the tube twice with buffer containing 1% SDS. Four more washes with wash buffer (5 mM Tris-HCl pH 7.5, 0.5 mM EDTA. 1 mM NaCl and 200 µg/µl BSA). For the last wash use 1× ligation buffer.

Ligating MmeI-BseRI Adaptors to cDNA.

Place the tube on magnetic stand to remove the supernatant (the ligation buffer). Add the following reagents to the beads on ice.

| Contents | Tube A | Tube B |
|---|---|---|
| cDNA beads | beads | beads |
| MmeI-BseRI adaptor A (20 ng/µl) | 1.5 µl | — |
| MmeI-BseRI adaptor B (20 ng/µl) | — | 1.5 µl |
| TE | 14 µl | 14 µl |
| 10X ligation buffer | 2 µl | 2 µl |

Heat the tubes for 2' at 50° C. and cool to room temp. for 15' and chill the samples on ice. Add 2.5 µl T4 DNA ligase and mix. Incubate at 16° C. for 2 hours. Mix occasionally. Wash the tubes with wash buffer to remove the excess adaptors.

Cleaving with Tagging Enzyme MmeI

Place the two tubes (A and B) on magnetic stand, remove the supernatant (wash buffer). Add the following reagents to each tube: ddH20 86 µl, MmeI 2 µl, 10× buffer 10 µl (1:10) SAM 2 µl. Total volume 100 µl. Incubate at 37° C. for 1 hour with mixing.

Remove the supernatant which contains the tags. Phenol/chloroform and precipitate.

Ligating Tags to Create Ditags

Resuspend the pellet in 1.5 µl, mix both A and B tubes and add 1.5 µl of the following reagents to form the ditags: 3 mM Tris-HCl, pH 7.5 1.25 µl, 10× Ligation buffer 0.75 µl, ddH$_2$O 0.75 µl, T4 ligase 1 µl. Incubate at 16° C. for overnight.

PCR Amplifying and Gel Purifying the 138 Bp Ditags

Set up 200 to 300 reactions as following (in 96 PCR plates):

| 10XBV buffer | 5 µl |
|---|---|
| DMSO | 3 µl |
| dNTPmix | 7.5 µl |
| PCR primer A (175 ng/µl) | 2 µl |
| PCR primer B (175 ng/µl) | 2 µl |
| ddH$_2$O | 29 µl |
| Platinum Taq enzyme | 0.5 µl |
| Template (1:230 dilution) | 1 µl |
| Total volume | 50 µl |

Cycling condition: 95° C. 2' 1 cycle. 95° C. 30", 55° C. 1', 70° C. 1'. 27 cycles. 70° C. 5'. Run a diagnostic 4% agarose gel to analyze the PCR product and purify the 138 bp ditags by 12% polyacrylamide gel electrophoresis.

Digesting the Ditags with Anchoring Enzyme Bseri and Purifying the 48 Bp Ditag

Digest the 138 bp ditags with BseRI to yield 48 bp ditag.

| 138 bp ditags | 42 µl |
|---|---|
| 10X NEB buffer II | 15 µl |
| BseRI | 12 µl |
| ddH$_2$0 | 81 µl |
| Total volume | 150 µl |

And incubate at 37° C. for 2 to 3 hours. Phenol/chloroform and EtoH precipitate. Run a diagnostic 4% agarose gel to check the efficiency of the digestion and purify the 48 bp ditags by 12% polyacrylamide gel electrophoresis. Ligate the 48 bp ditag to form concatamers.

Ligating the 48 Bp Ditag to Form Concatamers

Set up the ligation reaction using the gel purified ditag in a total volume of 10 µl and incubate 16 C for 2 to 3 hours. Gel purify the concatamers from 8% polyacrylamide, select the DNA size range from 1 to 1.5 kbp.

Cloning Concatamers into Vector

In a separate reaction, digest the plasmid vector with HhaI and ligate the purified concatamers into the linearized vector following standard molecular biology protocol. Transform the ligation into high efficiency competent cells.

To keep on walking into the 3' end of the cDNA, just take the beads from step: Cleavage the cDNA with tagging enzyme MmeI and repeat the whole process again.

3' SAGE Walk Operational Protocol

Follow the 3' terminal tag protocol to step: Cleaving with Tagging enzyme MmeI.

After the digestion is completed, inactivate the enzyme by washing the tube twice with buffer containing 1% SDS. Four more washes with wash buffer (5 mM Tris-HCl pH 7.5, 0.5mM EDTA. 1 mM NaCl and 200 µg/µl BSA). For the last wash use 1× ligation buffer.

Ligating MmeI-BseRI Adaptors to cDNA

Place the tube on magnetic stand to remove the supernatant (the ligation buffer). Add the following reagents to the beads on ice.

| Contents | Tube A | Tube B |
|---|---|---|
| cDNA beads | beads | beads |
| MmeI-BseRI adaptor A (20 ng/µl) | 1.5 µl | — |
| MmeI-BseRI adaptor B (20 ng/µl) | — | 1.5 µl |
| TE | 14 µl | 14 µl |
| 10X ligation buffer | 2 µl | 2 µl |

Heat the tubes for 2' at 50° C. and cool to room temp. for 15' and chill the samples on ice. Add 2.5 µl T4 DNA ligase and mix. Incubate at 16° C. for 2 hours. Mix occasionally. Wash the tubes with wash buffer to remove the excess adaptors.

Cleaving with Tagging Enzyme MmeI

Place the two tubes (A and B) on magnetic stand, remove the supernatant (wash buffer). Add the following reagents to each tube.

| ddH$_2$O | 86 µl |
|---|---|
| MmeI | 2 µl |
| 10X buffer | 10 µl |
| (1:10) SAM | 2 µl |
| Total volume | 100 µl. |

Incubate at 37° C. for 1 hour with mixing. Remove the supernatant which contains the tags. Phenol/chloroform and precipitate. Resuspend the pellet.

Ligating Tags to Create Ditags

Pool the A and B tubes. Resuspend the pellet in 1.51 μl and add 1.5 μl of the following reagents to form the ditags.

| | |
|---|---|
| 3 mM Tris-HCl, pH 7.5 | 1.25 μl |
| 10X Ligation buffer | 0.75 μl |
| ddH$_2$0 | 0.75 μl |
| T4 ligase | 1 μl |

Incubate at 16° C. for overnight.

PCR Amplifying and Gel Purifying the 138 Bp Ditags

Set up 200 to 300 reactions as following (in 96 PCR plates).

| | |
|---|---|
| 10XBV buffer | 5 μl |
| DMSO | 3 μl |
| dNTPmix | 7.5 μl |
| PCR primer A (175 ng/μl) | 2 μl |
| PCR primer B (175 ng/μl) | 2 μl |
| ddH$_2$0 | 29 μl |
| Platinum Taq enzyme | 0.5 μl |
| Template (1:230 dilution) | 1 μl |
| Total volume | 50 μl |

Cycling condition: 95° C. 2' 1 cycle. 95° C. 30", 55° C. 1', 70° C. 1'. 27 cycles. 70° C. 5'. Run a diagnostic 4% agarose gel to analyze the PCR product and purify the 138 bp ditags by 12% polyacrylamide gel electrophoresis.

Digesting the Ditags with Anchoring Enzyme Bseri and Purifying the 48 Bp Ditag

Digest the 138 bp ditags with BseRI to yield 48 bp ditag.

| | |
|---|---|
| 138 bp ditags | 42 μl |
| 10X NEB buffer II | 15 μl |
| BseRI | 12 μl |
| ddH$_2$0 | 81 μl |
| Total volume | 150 μl |

And incubate at 37° C. for 2 to 3 hours. Phenol/chloroform and EtoH precipitate. Run a diagnostic 4% agarose gel to check the efficiency of the digestion and purify the 48 bp ditags by 12% polyacrylamide gel electrophoresis.

Ligating the 48 Bp Ditag to Form Concatamers

Set up the ligation reaction using the gel purified ditag in a total volume of 10 μl and incubate 16 C for 2 to 3 hours. Gel purify the concatamers from 8% polyacrylamide, select the DNA size range from 1 to 1.5 kbp.

Cloning Concatamers into Vector

In a separate reaction, digest the plasmid vector with HhaI and ligate the purified concatamers into the linearized vector following standard molecular biology protocol. Transform the ligation into high efficiency competent cells.

To keep on walking toward the 5' end of the cDNA, just take the beads from step: Cleavage the cDNA with tagging enzyme MmeI and repeat the whole process again.

Example 6

DNA Sequencing and Data Analysis

DNA templates of the concatamer clones are prepared and subject for standard sequencing analysis. A typical DNA sequence provides about 800 bp nucleotide sequences and contains about 17-18 ditags, or 30-40 tags.

With a concatamer clone of larger than 2000 bp of insert, sequencing analysis is performed from both ends to generate up to 80 tags per run. Therefore, a modest sequencing effort of 12,500 clones generates over one million tags, and 25,000 clones sequences (50,000 reads) generates one million pairs of 5' and 3' LongSAGE tags.

After sequencing of generating the draw sequence data, the ditag sequences are first extracted then the single tags. Both 5' and 3' tags are compared together to the corresponding genome sequence database using BLAST. Pairs of 5' and 3' tags of known genes and putative genes are clustered based on genome and cDNA sequences.

APPENDIX A

Sequences

```
5' TERMINAL SAGE LINKERS AND PRIMERS                              (SEQ ID NO: 67)
NotI-dT15 primer for cDNA synthesis
     5' GACTAGTTCTAGATCGCGAGCGGCCGCCC (T)15VN
                              NotI
Biotin-NotI linker
     5'-biotin-GACTAGTTCTAGATCGCGAGC                               (SEQ ID NO: 68)
               CTGATCAAGATCTAGCGCTCGCCGGp-3                        (SEQ ID NO: 69)
MmeI-BseRI Linker A (48nt)                                         (SEQ ID NO: 70-71, respectively,
                                 BseRI        MmeI                 in order of appearance.)
5'-TTT GGA TTT GCT GGT GCA GTA CAA CTA GGC GAGGAGCGTCTCTCCGAC
    a-CCT AAA CGA CCA CGT CAT GTT GAT CCG CTCCTCGCAGAGAGGCTG-P
                                              BsmBI
MmeI-BseRI Linker B (48nt)                                         (SEQ ID NO: 72-73, respectively,
                                 BseRI        MmeI                 in order of appearance.)
5'-TTT CTG CTC GAA TTC AAG CTT CTA ACG TAC GAGGAGCGTCTCTCCGAC
    a-GAC GAG CTT AAG TTC GAA GAT TGC ATG CTCCTCGCAGAGAGGCTG-P
                                              BsmBI
Second round MmeI-BseRI Linker A (50nt)                            (SEQ ID NO: 74-75, respectively,
                                 BseRI        MmeI                 in order of appearance.)
5'-TTT GGA TTT GCT GGT GCA GTA CAA CTA GGC GAGGAGCGTCTCTCCGACNN
    a-CCT AAA CGA CCA CGT CAT GTT GAT CCG CTCCTCGCAGAGAGGCTG-P
                                              BsmBI
Second round MmeI-BseRI Linker B (50nt)                            (SEQ ID NO: 76-77, respectively,
                                 BseRI        MmeI                 in order of appearance.)
5'-TTT CTG CTC GAA TTC AAG CTT CTA ACG TAC GAGGAGCGTCTCTCCGACNN
```

```
              a-GAC GAG CTT AAG TTC GAA GAT TGC ATG CTCCTCGCAGAGAGGCTG-P
                                                        BsmBI
PCR primer A (29nt, 20nt)
       biotin-5'-GTG CTC GTG GGA TTT GCT GGT GCA GTA CA               (SEQ ID NO: 78)
PCR primer B (29nt, 20nt)
       biotin-5'-GAG CTC GTG CTG CTC GAA TTC AAG CTT CT               (SEQ ID NO: 79)
3' TERMINAL SAGE LINKERS AND PRIMERS
FseI-dT15 primer (for cDNA synthesis)
       biotin-GACTAGTTCTAGATCGCGAGGCCGGCC (T)13VN                     (SEQ ID NO: 80)
                                 FseI
5' biotin linker
       (The biotin oligo is same as the PCR primer A)
              5'-biotin-GTGCTCGTGGGATTTGCTGGTGCAGTACA                 (SEQ ID NO: 81)
                       CACGAGCACCCTAAAGCACCACGTCATGT-p-3'             (SEQ ID NO: 82)
1/2FseI-MmeI linker (to introduce MmeI site and remove polyA)
              pTCGGATCGCGATCTAGAACTAGTC                               (SEQ ID NO: 83)
              3'-GGCCAGCCTAGCGCTAGATCTTGATCAGTTT-5'                   (SEQ ID NO: 84)
                    MmeI
Second round MmeI-BseRI Linker A (50nt)                               (SEQ ID NO: 85-86, respectively,
                          BseRI          MmeI                         in order of appearance.)
5'-TTT GGA TTT GCT GGT GCA GTA CAA CTA GGC GAGGAGCGTCTCTCCGACNN
       a-CCT AAA CGA CCA CGT CAT GTT GAT CCG CTCCTCGCAGAGAGGCTG-P
                                                    BsmBI
Second round MmeI-BseRI Linker B (50nt)                               (SEQ ID NO: 87-88, respectively,
                          BseRI          MmeI                         in order of appearance.)
5'-TTT CTG CTC GAA TTC AAG CTT CTA ACG TAC GAGGAGCGTCTCTCCGACNN
       a-GAC GAG CTT AAG TTC GAA GAT TGC ATG CTCCTCGCAGAGAGGCTG-P
                                                    BsmBI
PCR primer A (29nt, 20nt)
       biotin-5-GTG CTC GTG GGA TTT GCT GGT GCA GTA CA                (SEQ ID NO: 89)
PCR primer B (29nt, 20nt)
       biotin-5'-GAG CTC GTG CTG CTC GAA TTC AAG CTT CT               (SEQ ID NO: 90)
EXAMPLES 1 & 2 PRIMER/LINKER SEQUENCES
NotI-dT20 primer           40 mers
GAGAGAGAGAGCGGCCGCTTTTTTTTTTTTTTTTTTTTVN                              (SEQ ID NO: 91)
NotI Linker top                     25 mers
5'phosphate-GGCCGCTCGCGATCTAGAACTAGTC                                 (SEQ ID NO: 92)
NotI Linker bottom         21mers
5' biotin-GACTAGTTCTAGATCGCGAGC                                       (SEQ ID NO: 93)
Linker A top (N5)          54mers
TTTGGATTTGCTGGTGCAGTACAACTAGGCGAGGAGCGTCTCTCCGACGNNNNN                (SEQ ID NO: 94)
Linker A top (N6)          54mers
TTTGGATTTGCTGGTGCAGTACAACTAGGCGAGGAGCGTCTCTCCGACNNNNNN                (SEQ ID NO: 95)
Linker A bottom            45mers
5'phosphate-GTCGGAGAGACGCTCCTCGCCTAGTTGTACTGCACCAGCAAATCC             (SEQ ID NO: 96)
Linker B top (N5)          54mers
TTTCTGCTCGAATTCAAGCTTCTAACGTACGAGGAGCGTCTCTCCGACGNNNNN                (SEQ ID NO: 97)
Linker B top (N6)          54mers
TTTCTGCTCGAATTCAAGCTTCTAACGTACGAGGAGCGTCTCTCCGACNNNNNN                (SEQ ID NO: 98)
Linker B bottom            45mers
5'phosphate-GTCGGAGAGACGCTCCTCGTACGTTAGAAGCTTGAATTCGAGCAG             (SEQ ID NO: 99)
PCR primer A               29mers
GTGCTCGTGGGATTTGCTGGTGCAGTACA                                         (SEQ ID NO: 100)
PCR primer B               29mers
GAGCTCGTGCTGCTCGAATTCAAGCTTCT                                         (SEQ ID NO: 101)
EXAMPLES 3 & 4 PRIMER/LINKER SEQUENCES
GsuI-dT16 primer           34 mers
GAGAGAGAGAGACTGGAGTTTTTTTTTTTTTTTTVN                                  (SEQ ID NO: 102)
MmeI-BseRI Linker A top              50 mers
5'-TTTGGATTTGCTGGTGCAGTACAACTAGGCGAGGAGCGTCTCTCCGACTT                 (SEQ ID NO: 103)
MmeI-BseRI Linker A bottom           45 mers
5'phosphate-GTCGGAGAGACGCTCCTCGCCTAGTTGTACTGCACCAGCAAATCC             (SEQ ID NO: 104)
MmeI-BseRI Linker B top              50 mers
5'-TTTCTGCTCGAATTCAAGCTTCTAACGTACGAGGAGCGTCTCTCCGACTT                 (SEQ ID NO: 105)
MmeI-BseRI Linker B bottom           45mers
5'phosphate-GTCGGAGAGACGCTCCTCGTACGTTAGAAGCTTGAATTCGAGCAG             (SEQ ID NO: 106)
SalI adaptor top           16mers
5'biotin-TCGACCCACGCGTCCG                                             (SEQ ID NO: 107)
SalI adaptor bottom                  16mers
5'phosphate-CGGACGCGTGGGTCGA                                          (SEQ ID NO: 108)
PCR primer A               29mers
GTGCTCGTGGGATTTGCTGGTGCAGTACA                                         (SEQ ID NO: 109)
PCR primer B               29mers
GAGCTCGTGCTGCTCGAATTCAAGCTTCT                                         (SEQ ID NO: 110)
EXAMPLE 5 SAGE WALKING PRIMER/LINKER SEQUENCES
5' SAGE Walking Primer/Linker sequences
Linker A top     50mers
TTTGGATTTGCTGGTGCAGTACAACTAGGCGAGGAGCGTCTCTCCGACNN                    (SEQ ID NO: 111)
Linker A bottom    45mers
5'phosphate-GTCGGAGAGACGCTCCTCGCCTAGTTGTACTGCACCAGCAAATCC             (SEQ ID NO: 112)
```

```
Linker B top      50mers
TTTCTGCTCGAATTCAAGCTTCTAACGTACGAGGAGCGTCTCTCCGACNN                (SEQ ID NO: 113)
Linker B bottom       45mers
5'phosphate-GTCGGAGAGACGCTCCTCGTACGTTAGAAGCTTGAATTCGAGCAG          (SEQ ID NO: 114)
PCR primer A      29mers
GTGCTCGTGGGATTTGCTGGTGCAGTACA                                     (SEQ ID NO: 115)
PCR primer B      29mers
GAGCTCGTGCTGCTCGAATTCAAGCTTCT                                     (SEQ ID NO: 116)
3' SAGE Walking Primer/Linker sequences
MmeI-BseRI Linker A top       50 mers
5'-TTTGGATTTGCTGGTGCAGTACAACTAGGCGAGGAGCGTCTCTCCGACNN              (SEQ ID NO: 117)
MmeI-BseRI Linker A bottom        45 mers
5'phosphate-GTCGGAGAGACGCTCCTCGCCTAGTTGTACTGCACCAGCAAATCC          (SEQ ID NO: 118)
MmeI-BseRI Linker B top         50 mers
5'-TTTCTGCTCGAATTCAAGCTTCTAACGTACGAGGAGCGTCTCTCCGACNN              (SEQ ID NO: 119)
MmeI-BseRI Linker B bottom        45mers
5'phosphate-GTCGGAGAGACGCTCCTCGTACGTTAGAAGCTTGAATTCGAGCAG          (SEQ ID NO: 120)
PCR primer A      29mers
GTGCTCGTGGGATTTGCTGGTGCAGTACA                                     (SEQ ID NO: 121)
PCR primer B      29mers
GAGCTCGTGCTGCTCGAATTCAAGCTTCT                                     (SEQ ID NO: 122)
```

APPENDIX B

TABLE 1

Table 1: Theoretical 5'tag complexity and uniqueness probability of matching to transcriptome and genome

| Tag length n | Tag Complexity, C | Tag uniqueness to transcriptome, Ut | Tag uniqueness to human genome, Ug |
|---|---|---|---|
| 4 | 256 | 1562 | 11718750 |
| 6 | 4096 | 146 | 732422 |
| 10 | 1048576 | 0.95 | 2861 |
| 14 | 268435456 | 0.0052 | 11 |
| 16 | 4294967296 | 0.00037 | 0.7 |
| 18 | 68719476736 | 0.000026 | 0.04 |
| 20 | 1099511627776 | 0.0000018 | 0.003 |

C, the complexity of tags. $C=4^n$, where n is the tag length. Short tags have less complexity and, therefore, are more frequent in a genome. The numbers indicate, in average, the size of sequence base pairs for a specific tag to occur once. For example a 6-bp tag will occur once in a genome every 4096 bp, while a 10-bp tag will appear only once in a one million bp sequence.

Ut, tag uniqueness to transcripts of a genome, is determined under the assumption that there are 100,000 distinct transcripts in a complex genome like human, mouse, or Zebrafish, and the 5' sequences of transcripts are random. Ut=n*100,000/C, indicates the number of transcripts that might share a same unique 5'tag.

Ug, the tag uniqueness to human genome. Ug is determined as the genome size (3,000,000,000 bp) divided by tag complexity. Ug=Gs/C, Gs is the genome size in bp. The numbers indicate the potential matches of a particular tag in the genome.

The invention is further described by the following numbered paragraphs:

1. A method of obtaining a nucleotide sequence tag from a terminus of a nucleic acid, the method comprising the steps of:
    (a) providing a first nucleic acid sequence;
    (b) linking the first nucleic acid sequence to an linker sequence to form a linked nucleic acid, in which the linker sequence comprises:
        (i) a first recognition site for a first nucleic acid cleavage enzyme that allows cleavage of the first nucleic acid sequence at a site distant from the first recognition site, and
        (ii) a second recognition site for a second nucleic acid cleavage enzyme that allows nucleic acid cleavage at a site distant from the second recognition site, said cleavage site located at a position within or about the first recognition site;
    in which the linked nucleic acid has the structure: 5'-second recognition site-first recognition site-first nucleic acid-3'
    (c) cleaving the linked nucleic acid with the first nucleic acid cleavage enzyme to provide:
        (i) a linked tag comprising the linker sequence linked to a nucleotide sequence tag representative of the first nucleic acid sequence and comprising a terminal portion thereof; and
        (ii) a second nucleic acid sequence comprising a remainder portion of the first nucleic acid.

2. A method according to Paragraph 1, in which the first nucleic acid comprises a complementary deoxyribonucleic acid (cDNA) having a terminus comprising a 5' terminal transcribed sequence of a gene, and in which the linker sequence is linked to said terminus.

3. A method according to Paragraph 1, in which the first nucleic acid comprises a complementary deoxyribonucleic acid (cDNA) having a terminus comprising a 3' terminal transcribed sequence of a gene, and in which the linker sequence is linked to said terminus.

4. A method according to Paragraph 1, 2 or 3, in which the second nucleic acid cleavage enzyme comprises a restriction endonuclease, preferably a Type IIS restriction endonuclease, whose recognition site is 6 bases or greater, preferably MmeI.

5. A method according to any preceding paragraph, in which the first nucleic acid cleavage enzyme comprises a restriction endonuclease, preferably a Type IIS restriction endonuclease, preferably BseRI.

6. A method of sequentially generating a plurality of nucleic acid sequences each comprising a nucleotide sequence tag from a nucleic acid, the method comprising repeating steps (a) to (c) of any of Paragraphs 1 to 5 at least once, in which the first nucleic acid sequence of step (a) is provided by the second nucleic acid sequence of step (c)(ii).

7. A method of providing an indication of an instance of expression of a gene, the method comprising a method according to any preceding paragraph, and further comprising the step of detecting the presence, sequence or identity of the linked tag or the nucleotide sequence tag to provide an indication of an instance of gene expression.

8. A method of detecting gene expression, the method comprising the steps of:
   (a) providing a first linked tag and a second linked tag, each independently produced by a method according to any preceding paragraph;
   (b) linking the first linked tag and the second linked tag such that the nucleotide sequence tag portion of one linked tag is linked to the nucleotide sequence tag of the other linked tag to form a ditag, the ditag comprising terminal transcribed sequences from first and second genes; and
   (c) detecting the presence or identity of the ditag, or at least one nucleotide sequence tag comprised therein, to detect gene expression.

9. A method according to Paragraph 8, in which each of the first and second linker sequences comprised in the first and second linked tags comprises an amplification primer sequence, and in which the method further comprises a step of amplifying the ditag, preferably by means of the polymerase chain reaction (PCR).

10. A method according to Paragraph 8 or 9, further comprising the steps of:
   (d) cleaving the ditag with the or each second nucleic acid cleavage enzyme;
   (e) linking a plurality of the resultant trimmed ditags to form a concatamer; and
   (f) obtaining the nucleic acid sequence of at least a portion of the concatamer.

11. A method of providing an indication of an instance of expression of a gene, the method comprising the steps of:
   (a) providing a complementary deoxyribonucleic acid (cDNA) having a terminus comprising a terminal transcribed sequence of a gene;
   (b) linking the cDNA to an linker sequence thereby forming a linked nucleic acid, in which the linker sequence comprises a first recognition site for a first nucleic acid cleavage enzyme, preferably a restriction endonuclease, that allows nucleic acid cleavage at a site distant from the first recognition site; and
   (c) cleaving the linked nucleic acid with the first nucleic acid cleavage enzyme to provide a linked tag, in which the linked tag comprises a nucleotide sequence tag representative of a terminal transcribed sequence of the gene; and
   (d) detecting the presence or identity of the linked tag or the nucleotide sequence tag to provide an indication of an instance of gene expression.

12. A method according to Paragraph 10, in which the 5' end of the cDNA comprises a sequence corresponding to the 5' terminal transcribed sequence of the gene, and in which the linker sequence is linked to the 5' end of the cDNA.

13. A method according to Paragraph 11 or 12, in which the nucleotide sequence tag comprises a 5' terminal transcribed sequence of the gene, preferably at least the first 16 bases of the transcribed portion of the gene, more preferably the first 20 bases of the transcribed portion of the gene.

14. A method according to Paragraph 11, in which the 3' end of the cDNA comprises a sequence corresponding to the 3' terminal transcribed sequence of the gene, and in which the linker sequence is linked to the 3' end of the cDNA.

15. A method according to Paragraph 11 or 14, in which the nucleotide sequence tag comprises a 3' terminal transcribed sequence of the gene, preferably at least the last 16 bases of the transcribed portion of the gene, more preferably the last 20 bases of the transcribed portion of the gene.

16. A method according to Paragraph 11, 14 or 15, in which step (a) comprises:
   (i) deriving a cDNA from an mRNA by reverse transcription with an primer comprising a sequence 5'-NV(T)$^{13}$CCGGCCGG-3' (SEQ ID NO: 4), in which N=A, C, G or T and V=A, C or G;
   (ii) producing a double stranded cDNA therefrom and digesting the double stranded cDNA with FseI to produce a cleaved cDNA comprising $$3'\frac{GGCCGG}{CC}$$

overhang;
   (iii) linking the cleaved cDNA to a linker comprising $$\frac{pTCGGA}{GGCCAGCCT};$$

and
   (iv) cleaving the resulting molecule with MmeI to produce a cDNA lacking a polyA/T tail.

17. A method according to any of Paragraphs 11 et seq, in which the cDNA comprises the 5' terminal transcribed sequence of the gene, or the 3' terminal transcribed sequence of the gene, or both.

18. A method according to any preceding of Paragraphs 11 et seq, in which the cDNA is full length cDNA, preferably comprising substantially all the coding sequence of the gene.

19. A method of obtaining sequential sequence information from a gene, the method comprising steps (a) to (c) of a method according to Paragraph 11, or any paragraph dependent thereon, the method further comprising:
   (d) providing a second nucleic acid from step (c) comprising 3' remaining sequences of the cDNA;
   (e) linking the second nucleic acid to an linker sequence, thereby forming a linked nucleic acid, in which the linker sequence comprises a recognition site for a nucleic acid cleavage enzyme, preferably a restriction endonuclease, that allows nucleic acid cleavage at a site distant from the recognition site;
   (f) cleaving the linked nucleic acid with the nucleic acid cleavage enzyme to provide: (i) a linked tag comprising the linker sequence linked to a nucleotide sequence tag comprising a 5' portion of the second nucleic acid; and (ii) a fourth nucleic acid sequence comprising a 3' remainder portion of third nucleic acid;
   (g) repeating steps (d) to (f) at least once, in which the second nucleic acid sequence of step (d) is provided by the fourth nucleic acid sequence of step (f)(ii); and
   (h) detecting the presence, identity or sequence of at least one linked tag or a nucleotide sequence tag comprised therein.

20. A method according to any of Paragraphs 11 et seq, in which the linker sequence further comprises a second recognition site for a second nucleic acid cleavage enzyme, preferably a second restriction endonuclease, that allows nucleic acid cleavage at a site distant from the second recognition site, and in which the second recognition site is located 5' of the first recognition site in the linker sequence.

21. A method according to Paragraph 20, in which the location of the second recognition site with respect to the first recognition site is such that, when the linked tag is exposed to the second nucleic acid cleavage enzyme, cleavage of the nucleic acid occurs at a position within or about the first recognition site.

22. A method according to any of Paragraphs 11 et seq, in which the first recognition site or the second recognition site, or both, comprises a Type IIS restriction enzyme recognition site.

23. A method according to any of Paragraphs 11 et seq, in which the first restriction enzyme comprises MmeI, or in which the first recognition site comprises a MmeI recognition site 5'-TCC RAC-3', preferably 5'-TCC GAC-3'.

24. A method according to Paragraph 22 or 23, in which the second restriction enzyme comprises a restriction enzyme capable of recognising a site which is 6 bases or longer, preferably BseRI, or in which the second recognition site comprises a BseRI recognition site 5'-GAGGAG-3'.

25. A method according to any of Paragraphs 11 et seq, in which the linker sequence comprises the sequence 5'-GAGGAGNNNNNNTC▲CG▼AC-3' (SEQ ID NO: 1), preferably 5'-GAGGAGCGTCTCTCCGAC-3' (SEQ ID NO: 2).

26. A method of detecting expression of a gene, the method comprising:
   (a) providing a first linked tag and a second linked tag, each independently produced by a method according to any preceding paragraph;
   (b) linking the first linked tag and the second linked tag such that the nucleotide sequence tag portion of one linked tag is linked to the nucleotide sequence tag of the other linked tag to form a ditag, the ditag comprising terminal transcribed sequences from first and second genes; and
   (c) detecting the presence or identity of the ditag, or at least one nucleotide sequence tag comprised therein, to detect gene expression.

27. A method according to Paragraph 26, in which each of the first linker sequence of the first linked tag and the second linker sequence of the second linked tag comprises an amplification primer hybridisation sequence.

28. A method according to Paragraph 27, in which the method further comprises a step of amplifying the ditag, preferably by means of the polymerase chain reaction (PCR).

29. A method according to any of Paragraphs 26 to 28 as dependent on any of Paragraphs 20 to 25, which further comprises the step of cleaving the ditag with the or each second nucleic acid cleavage enzyme to provide a trimmed ditag.

30. A method according to any of Paragraphs 26 to 29, in which the trimmed ditag comprises between 12 to 120 base pairs, preferably between 18 to 46 base pairs, preferably 40 base pairs.

31. A method according to any of Paragraphs 26 to 30, in which a plurality of ditags or trimmed ditags are linked to form a concatamer.

32. A method according to any of Paragraphs 26 to 31, in which the concatamer comprises between 2 to 200 ditags or trimmed ditags, preferably between 10 to 40 ditags or trimmed ditags, preferably between 8 to 20 ditags or trimmed ditags.

33. A method according to any of Paragraphs 11 et seq, further comprising the step of determining the sequence of a or each linked tag, nucleotide sequence tag, ditag, trimmed ditag or concatamer.

34. A method according to Paragraph 33, further comprising the step of determining the identity of the expressed gene by the comparing the sequence to a nucleotide sequence comprised in a database of nucleotide sequences.

35. A method according to Paragraph 33 or 34, in which the sequence is compared to a database of known genes, such that if the database does not comprise the sequence, the sequence comprises a new gene.

36. A method of providing an indication useful in the diagnosis of a disease in an individual, the method comprising:
   (a) providing a cell known to be affected by the disease;
   (b) determining if a gene is expressed in the cell of (b) by a method according to any preceding paragraph;
   (c) providing a cell of an individual suspected of suffering from the disease; and
   (d) determining whether the same gene is expressed in the cell of (c) by a method according to any preceding paragraph; and
   (e) comparing the expression, or lack thereof, of the gene between the cell of (b) and the cell of (c).

37. A method of producing determining the transcriptome of a cell, or obtaining a gene expression profile of a cell, the method comprising providing cDNA from the cell, subjecting said cDNA to a method according to any preceding paragraph, and determining whether a particular gene, or a particular set of genes, is expressed by the cell.

38. A method of providing an indication useful in the diagnosis of a disease in an individual, the method comprising comparing the gene expression profile of a cell known to be affected by the disease, with a cell of an individual suspected of suffering from the disease, in which either or both of the gene expression profiles are produced by a method according to Paragraph 37.

39. A method of determining the sequence of a control sequence of a gene, preferably a promoter or enhancer sequence, the method comprising:
   (a) obtaining a nucleotide sequence tag representative of the 5' terminal transcribed sequence of the gene by a method according to Paragraphs 1, 2, or 3, or any paragraph dependent thereon; and
   (b) obtaining a sequence of the gene 5' to the terminal transcribed sequence of (a), in which the sequence comprises a promoter or enhancer consensus sequence.

40. A method according to Paragraph 39, in which the sequence of the gene 5' to the terminal transcribed sequence of (a) is obtained by means of (a) chromosome walking, (b) SAGE walking, (c) nucleic acid hybridisation of a genomic library; or (d) querying a database of genomic sequences.

41. A database comprising a plurality of records, each record comprising an indication whether a gene is expressed by a particular cell, which indication is provided by a method according to any preceding paragraph.

42. A computer readable medium comprising a database according to Paragraph 41.

43. A nucleic acid sequence comprising a tag produced by a method according to any of Paragraphs 1 to 25.

44. A nucleic acid sequence comprising a ditag produced by a method according to any of Paragraphs 1 to 30.

45. A nucleic acid sequence comprising a concatamer comprising a plurality of tags according to Paragraph 43 or a plurality of ditags according to Paragraph 44.

46. A gene identified by a method according to Paragraph 35, or a protein encoded by the gene.

47. A control sequence, preferably a promoter sequence, identified by a method according to Paragraph 40.

48. A nucleic acid sequence comprising: (a) a recognition site for a nucleic acid cleavage enzyme, preferably a restriction endonuclease, that allows nucleic acid cleavage at a site distant from the first recognition site, and (b) a nucleotide sequence tag representative of a terminal transcribed sequence of a gene.

49. A nucleic acid sequence according to Paragraph 48, further comprising: (c) a second recognition site in which the second recognition site is for a second nucleic acid cleavage enzyme, preferably a second restriction endonuclease, that allows nucleic acid cleavage at a site distant from the second recognition site, and in which the cleavage site for the second nucleic acid cleavage enzyme is located within or about the first recognition site.

50. A linker sequence comprising:
(a) a first recognition site for a nucleic acid cleavage enzyme, preferably a restriction endonuclease, that allows nucleic acid cleavage at a site distant from the first recognition site;
(c) a second recognition site for a second nucleic acid cleavage enzyme, preferably a second restriction endonuclease, that allows nucleic acid cleavage at a site distant from the second recognition site;
in which in which the cleavage site for the second nucleic acid cleavage enzyme is located within or about the first recognition site.

51. A nucleic acid according to Paragraph 49, or a linker sequence according to Paragraph 50, in which the first recognition site and the second recognition site are spaced such that when the nucleic acid is exposed to the second nucleic acid cleavage enzyme, cleavage of the nucleic acid occurs at a position within the first recognition site.

52. A nucleic acid according to any of Paragraphs 48 to 51, in which the nucleic acid sequence comprises the sequence 5'-GAGGAGNNNNNNTC▲CG▼AC-3' (SEQ ID NO: 1), preferably 5'-GAGGAGCGTCTCTCCGAC-3' (SEQ ID NO: 2).

51. A method for detecting expression of a gene, the method comprising the steps of:
(a) providing a first complementary deoxyribonucleic acid (cDNA) having a terminus comprising a terminal transcribed sequence of a first gene;
(b) providing a second complementary deoxyribonucleic acid (cDNA) having a terminus comprising a terminal transcribed sequence of a second gene;
(c) linking the first cDNA so produced to a first linker sequence thereby forming a first linked nucleic acid, in which the first linker sequence comprises a first recognition site for a first nucleic acid cleavage enzyme, preferably a first restriction endonuclease, that allows nucleic acid cleavage at a site distant from the first recognition site;
(d) linking the second cDNA so produced to a second linker sequence thereby forming a second linked nucleic acid, in which the second linker sequence comprises a second recognition site for a second nucleic acid cleavage enzyme, preferably a second restriction endonuclease, that allows nucleic acid cleavage at a site distant from the second recognition site;
(e) cleaving the first linked nucleic acid with the first nucleic acid cleavage enzyme to provide a first linked tag, in which the first linked tag comprises a first nucleotide sequence tag representative of a terminal transcribed sequence of the first cDNA.
(f) cleaving the second linked nucleic acid with the second nucleic acid cleavage enzyme to provide a second linked tag, in which the second linked tag comprises a second nucleotide sequence tag representative of a terminal transcribed sequence of the second cDNA.
(g) ligating the first and second tags to form a ditag; and
(h) determining the nucleotide sequence of at least one tag of the ditag to detect gene expression.

52. A nucleotide sequence tag obtainable by a method according to any preceding paragraph.

Figure 2:
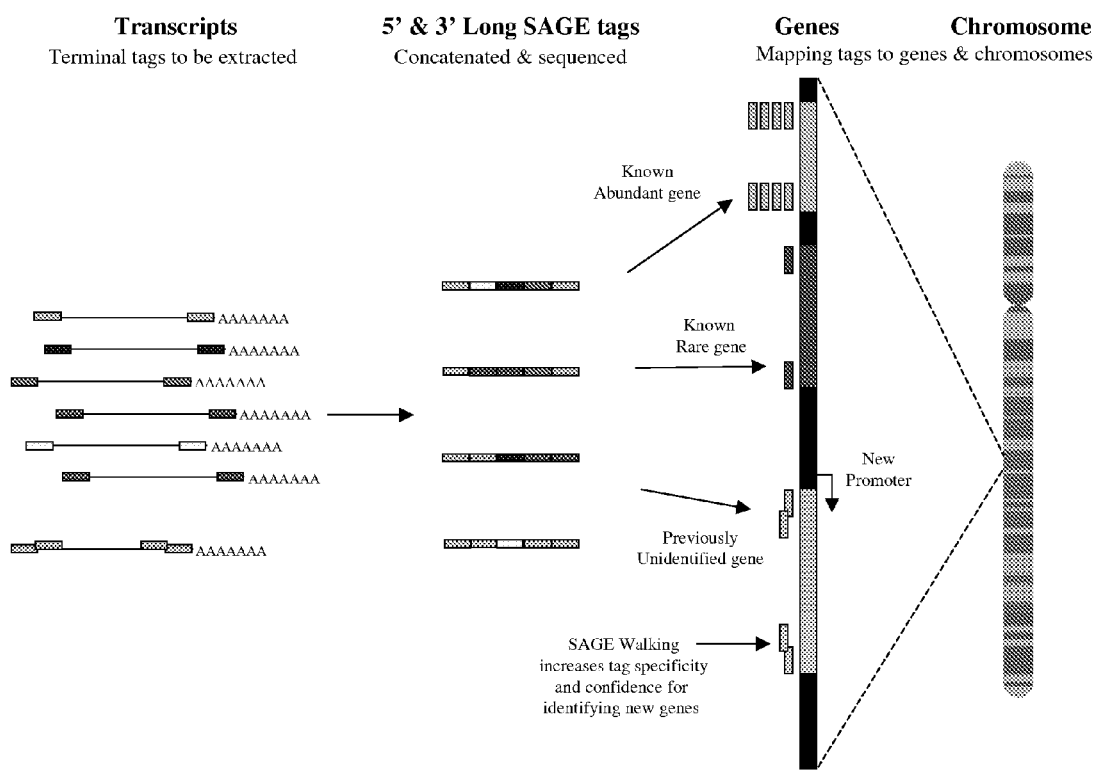
FIG. 2 is a schematic diagram of the 5' and 3'Terminal SAGE techniques described in this document and its application in genome annotation. 5' and 3'Terminal SAGE tags from full-length transcripts in a transcriptome are extracted using IIS type restriction enzymes. Tags are concatenated, cloned, sequenced, counted, and mapped to chromosome. Mapping of 5' and 3'tags to genome sequences allows precise localization and identification of genes as well as gene activities on chromosomes. Overlapping tags generated by serial rounds of SAGE Walking will immensely increase the tag specificity and confidence for identification of new gene and confirmation of predicted genes. The 5' tags also allow quick identification of large number of promoter sequences.

53. A method of obtaining a nucleotide sequence tag substantially as hereinbefore described with reference to and as shown in FIGS. 2 to 4 of the accompanying drawings.

54. A method of detecting gene expression substantially as hereinbefore described with reference to and as shown in FIGS. 2 to 4 of the accompanying drawings.

55. A method of 5' Terminal SAGE substantially as hereinbefore described with reference to and as shown in FIG. 3 of the accompanying drawings.

56. A method of 3' Terminal SAGE substantially as hereinbefore described with reference to and as shown in FIG. 4 of the accompanying drawings.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of obtaining a nucleotide sequence tag from a terminus of a nucleic acid, the method comprising the steps of:
   (a) providing a first nucleic acid sequence comprising a full-length first strand cDNA comprising a 5' untranslated region, a coding sequence, a 3' untranslated region and a poly A tail;
   (b) without prior cleavage of said first nucleic acid sequence, linking the 5' end of said full length first strand cDNA to a linker sequence to form a linked nucleic acid, in which the linker sequence comprises:
   (i) a first recognition site for a first nucleic acid cleavage enzyme that allows cleavage of the first nucleic acid sequence at a site distant from the first recognition site, and
   (ii) a second recognition site for a second nucleic acid cleavage enzyme that allows nucleic acid cleavage at a site distant from the second recognition site, said cleavage site located at a position within the first recognition site; in which the linked nucleic acid has the structure:
5'-second recognition site-first recognition site-first nucleic acid-3'

(c) cleaving the linked nucleic acid with the first nucleic acid cleavage enzyme to provide:

(i) a linked tag comprising the linker sequence linked to a nucleotide sequence tag representative of the first nucleic acid sequence, the nucleotide sequence tag comprising the 5' terminus of the full length first strand cDNA; and (ii) a second nucleic acid sequence comprising a remainder portion of the first nucleic acid.

2. The method according to claim 1, in which the second nucleic acid cleavage enzyme comprises a restriction endonuclease having a recognition site of 6 bases or greater.

3. The method according to claim 2, wherein the restriction endonuclease is MmeI.

4. The method according to claim 1, wherein the first nucleic acid cleavage enzyme is the restriction endonuclease BseRI.

5. A method of sequentially generating a plurality of nucleic acid sequences each comprising a nucleotide sequence tag from a nucleic acid, the method comprising performing the steps of the method of claim 1, followed by repeating at least once the steps of:

A) linking a linker sequence as described in step (b)(i) and (b)(ii) of claim 1 to said second nucleic acid sequence comprising a remainder portion of the first nucleic acid: and B) cleaving the linked second nucleic acid with the first nucleic acid cleavage enzyme to provide a linked tag comprising the linker sequence linked to a nucleotide sequence tag comprising the 5' terminus of said second nucleic acid, and a cleaved remainder portion of said second nucleic acid.

6. A method of providing an indication of an instance of expression of a gene, the method comprising the method according to claim 1, and further comprising the step of detecting the presence of the linked tag to provide an indication of an instance of gene expression.

7. A method of detecting gene expression, the method comprising the steps of:

(a) providing a first linked tag and a second linked tag, each independently produced by the method according to claim 1;

(b) linking the first linked tag and the second linked tag such that the nucleotide sequence tag portion of one linked tag is linked to the nucleotide sequence tag of the other linked tag to form a ditag, the ditag comprising terminal transcribed sequences from first and second genes; and (c) detecting the presence or identity of the ditag, or at least one nucleotide sequence tag comprised therein, to detect gene expression.

8. The method according to claim 7, in which each of the first and second linker sequences comprised in the first and second linked tags comprises an amplification primer sequence, and in which the method further comprises a step of amplifying the ditag.

9. The method according to claim 8, wherein the ditag is amplified by polymerase chain reaction (PCR).

10. The method according to claim 7, further comprising the steps of:

(d) cleaving the ditag with second nucleic acid cleavage enzyme;

(e) linking a plurality of the resultant trimmed ditags to form a concatamer; and (f) obtaining the nucleic acid sequence of at least a portion of the concatamer.

* * * * *